United States Patent
Matsuyama et al.

(10) Patent No.: US 9,638,849 B2
(45) Date of Patent: May 2, 2017

(54) LIQUID CRYSTAL COMPOUND, OPTICAL FILM, AND METHOD FOR PRODUCING OPTICAL FILM

(71) Applicant: FUJIFILM Corporation, Tokyo (JP)

(72) Inventors: Hiroshi Matsuyama, Kanagawa (JP); Shinichi Morishima, Kanagawa (JP); Yuki Nakazawa, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 0 days.

(21) Appl. No.: 14/672,888

(22) Filed: Mar. 30, 2015

(65) Prior Publication Data
US 2015/0277007 A1    Oct. 1, 2015

(30) Foreign Application Priority Data

Mar. 31, 2014  (JP) .................. 2014-071862
Mar. 10, 2015  (JP) .................. 2015-047028

(51) Int. Cl.
*C09K 19/00*    (2006.01)
*G02B 5/30*    (2006.01)
(Continued)

(52) U.S. Cl.
CPC .......... *G02B 5/3016* (2013.01); *C07D 277/64* (2013.01); *C07D 277/82* (2013.01);
(Continued)

(58) Field of Classification Search
CPC ...... G02B 5/3016; G02B 5/3083; G02B 5/32; C07D 277/64; C07D 277/82;
(Continued)

(56) References Cited

U.S. PATENT DOCUMENTS 8,257,611 B2    9/2012   Uehira et al.
2010/0045901 A1  2/2010  Uehira et al.
(Continued)

FOREIGN PATENT DOCUMENTS

JP    2008-273925 A    11/2008
JP    2009-274984 A    11/2009
(Continued)

OTHER PUBLICATIONS

Notification of Reasons for Refusal issued by the Japanese Patent Office on Feb. 16, 2016 in connection with corresponding Japanese Patent Application No. 2015-047028.
(Continued)

*Primary Examiner* — Ruiyun Zhang
(74) *Attorney, Agent, or Firm* — Jean C. Edwards, Esq.; Edwards Neils LLC

(57) ABSTRACT

An optical film of the present invention includes an optically anisotropic layer containing a compound represented by the following general formula (1) or an optically anisotropic layer formed by the curing of a polymerizable composition containing a compound represented by the following general formula (1):

General Formula (1)

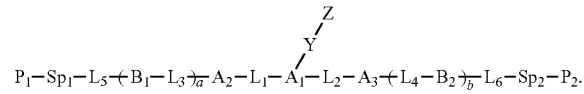

14 Claims, 1 Drawing Sheet

(51) Int. Cl.
*C07D 277/64* (2006.01)
*C07D 277/82* (2006.01)
*C08F 122/26* (2006.01)
*C08F 222/10* (2006.01)
*C08F 222/24* (2006.01)

(52) U.S. Cl.
CPC ...... *C08F 122/26* (2013.01); *C08F 222/1006* (2013.01); *C08F 222/24* (2013.01); *G02B 5/3083* (2013.01); *Y10T 428/10* (2015.01); *Y10T 428/1036* (2015.01); *Y10T 428/1041* (2015.01); *Y10T 428/31931* (2015.04)

(58) Field of Classification Search
CPC .. C07D 305/06; C07D 513/04; C07D 417/12; C08F 122/26; C08F 222/24; C08F 222/1006; C07C 2101/14; Y10T 428/10; Y10T 428/1036; Y10T 428/1041
USPC .......... 428/1.1, 1.3, 1.31, 1.33, 521; 349/96, 349/117; 548/161, 180; 546/114, 270.7; 560/127
See application file for complete search history.

(56) References Cited

U.S. PATENT DOCUMENTS

2014/0142266 A1   5/2014  Sakamoto et al.
2015/0175564 A1*  6/2015  Sakamoto ............ C07D 417/12
                                              526/257

FOREIGN PATENT DOCUMENTS

| JP | 2013-033248 A | | 2/2013 |
| JP | 2013033248 A | * | 2/2013 |
| WO | 2012/147904 A1 | | 11/2012 |
| WO | 2014/010325 A1 | | 1/2014 |

OTHER PUBLICATIONS

Notification of Reasons for Refusal issued by the Japanese Patent Office on Sep. 27, 2016 in connection with corresponding Japanese Patent Application No. 2015-047028.

* cited by examiner

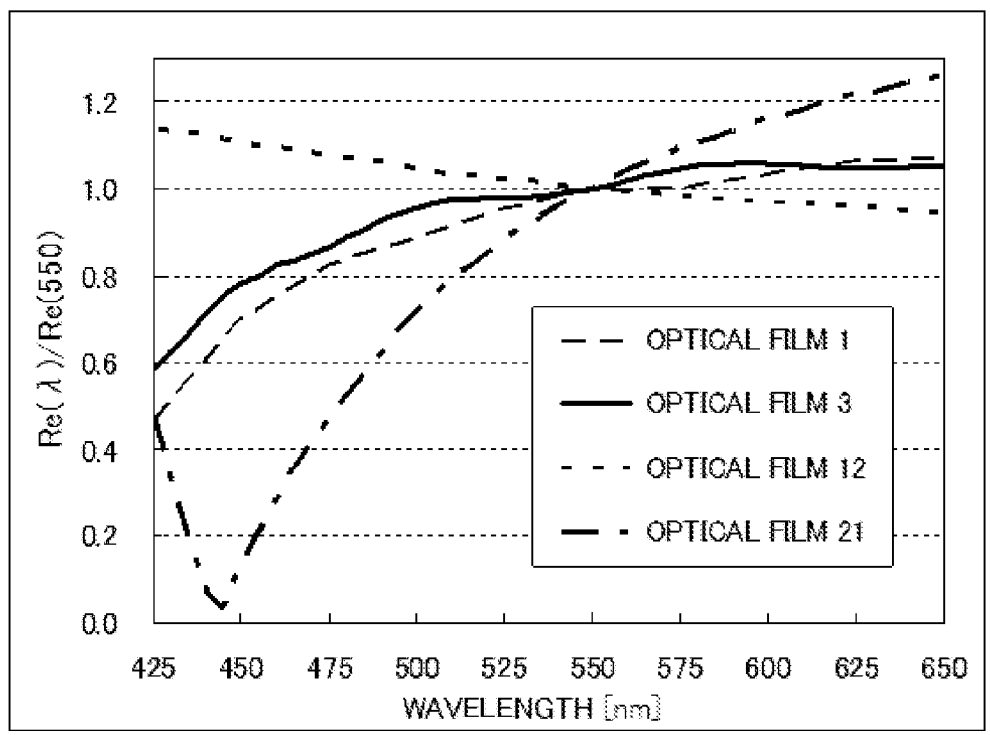

LIQUID CRYSTAL COMPOUND, OPTICAL FILM, AND METHOD FOR PRODUCING OPTICAL FILM

CROSS-REFERENCE TO RELATED APPLICATIONS

The present application claims priority under 35 U.S.C. §119 to Japanese Patent Application No. 2014-071862, filed on Mar. 31, 2014 and Japanese Patent Application No. 2015-047028, filed on Mar. 10, 2015. Each of the above applications is hereby expressly incorporated by reference, in its entirety, into the present application.

BACKGROUND OF THE INVENTION

1. Field of the Invention

The present invention relates to a liquid crystal compound, an optical film, and a method for producing an optical film.

2. Description of the Related Art

In the case where monochromatic light beam is transmitted through a λ/4 phase difference plate or a λ/2 phase difference plate, it is easy to convert the light into light having a wavelength with appropriate phase difference. However, in the case where white light having a plurality of monochromatic light beams therein is transmitted, it is difficult to convert all the light beams into ones having a wavelength with appropriate phase difference. The reason therefor is that materials constituting the phase difference plate have different phase difference with respect to the respective monochromatic light beams, and generally, a component having a shorter wavelength is more susceptible to phase difference. Thus, white light transmitted through the phase difference plate results in different phase difference with respect to the respective monochromatic light beams (a state of having different phase difference according to the wavelength is mentioned to have wavelength dispersion).

Accordingly, since white light obtained by light transmission through a phase difference plate has wavelength dispersion, there is a problem that polarized light converted by the phase difference plate due to a change in the polarization state at each wavelength would be colored.

In order to solve the aforementioned problems, broadband phase difference plates capable of providing uniform phase difference with respect to a wide-wavelength light have been investigated in various aspects. Specifically, compounds which exhibit reverse wavelength dispersion providing greater phase difference at a long wavelength have been investigated in various aspects (for example, JP2008-273925A, JP2009-274984A, and WO2012/147904A).

SUMMARY OF THE INVENTION

The present invention has an object to provide an optical film which exhibits excellent reverse wavelength dispersion. The present invention has another object to provide a novel liquid crystal compound which can be used for production of an optical film exhibiting excellent reverse wavelength dispersion and can be easily synthesized.

Means for solving the aforementioned problems are as described in <1> to <17> below.

<1> An optical film including an optically anisotropic layer containing a compound represented by the following general formula (1) or an optically anisotropic layer formed by the curing of a polymerizable composition containing a compound represented by the following general formula (1):

General Formula (1)

$$P_1-Sp_1-L_5\text{-}(B_1-L_3)_{\overline{a}}A_2-L_1-A_1\overset{\overset{\displaystyle Z}{\underset{\displaystyle |}{Y}}}{-}L_2-A_3\text{-}(L_4-B_2)_{\overline{b}}L_6-Sp_2-P_2$$

(in General Formula (1), $L_1$ to $L_6$ each independently represent a single bond or a linking group, $A_1$ represents an aromatic group which may have a substituent, $A_2$ and $A_3$ each independently represent a cyclic aliphatic group which may have a substituent, $B_1$ and $B_2$ each independently represent a cyclic aliphatic group which may have a substituent, or an aromatic group which may have a substituent, $Sp_1$ and $Sp_2$ each independently represent a spacer group, $P_1$ and $P_2$ each independently represent a polymerizable group, an alkyl group, or a hydrogen atom, Y represents a single bond or a linking group, Z represents an aromatic group which may have a substituent, and a and b each independently represent any one integer of 0 to 2).

<2> The optical film as described in <1>, in which Y is a single bond, $-R^1C=CR^{11}-$, $-R^2C=N-$, $-N=N-$, $-CO-NR^3-$, $-NR^4-CO-$, $-R^5C=N-NR^6-$, $-CO-NR^7-NR^8-$, $-R^9C=N-S-$, $-CO-NR^{10}-S-$, $-CO-S-$, $-R^{11}C=N-N=$, or $-R^{12}C=C-NR^{13}-$, $R^1$ to $R^{10}$, and $R^{12}$ and $R^{13}$ each independently represent a hydrogen atom or an alkyl group having 1 to 6 carbon atoms, and $R^{11}$ represents a hydrogen atom, an ester group, an acyl group, or a cyano group.

<3> The optical film as described in <1> or <2>, in which the aromatic group represented by Z is an aromatic group obtained by removing one or two hydrogen atoms from an aromatic cyclic compound represented by any one of the following Z-1 to Z-7, Q represents $-O-$, $-S-$, or $-NR^{17}-$, and $R^{17}$ represents a hydrogen atom or an alkyl group having 1 to 6 carbon atoms.

-continued

Z-5

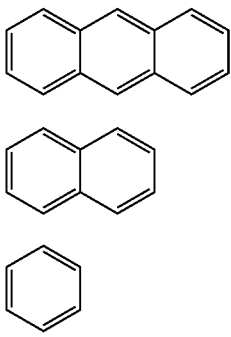

Z-6

Z-7

<4> The optical film as described in any one of <1> to <3>, in which the aromatic group represented by $A_1$ is a trivalent aromatic group represented by the following A1-1, A1-2, or A1-3, and *1, *2, and *Y each represent a bonding position with $L_1$, $L_2$, and Y:

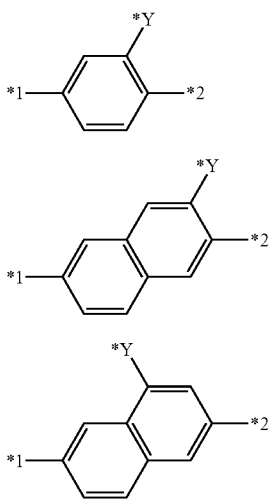

A1-1

A1-2

A1-3

<5> The optical film as described in any one of <1> to <4>, in which $A_2$, $A_3$, $B_1$, and $B_2$ are each a trans-1,4-cyclohexylene group.

<6> The optical film as described in any one of <1> to <5>, in which the spacer group is an alkylene group having 2 to 12 carbon atoms or an alkylene oxide group having 2 to 12 carbon atoms.

<7> The optical film as described in any one of <1> to <6>, in which $L_1$ and $L_2$ are each independently a single bond, —CO—, —CO—O—, or —O—CO—.

<8> The optical film as described in any one of <1> to <7>, in which $L_3$ and $L_4$ are each independently a single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, or —NR$^{25}$—CO—NR$^{26}$—, and $R^{21}$ to $R^{26}$ each represent a hydrogen atom or an alkyl group having 1 to 6 carbon atoms.

<9> The optical film as described in any one of <1> to <8>, including an optically anisotropic layer formed by the curing of a polymerizable composition containing the compound represented by General Formula (1), in which the polymerizable composition contains at least one or more asymmetric polymerizable compounds.

<10> The optical film as described in any one of <1> to <9>, comprising an optically anisotropic layer formed by the curing of a polymerizable composition containing the compound represented by General Formula (1),
wherein the polymerizable composition contains a compound where $B_1$ and $B_2$ in General Formula (1) each independently represent a divalent cyclic aliphatic group which may have a substituent and a compound where $B_1$ and $B_2$ in General Formula (1) each independently represent a divalent aromatic group which may have a substituent.

<11> The optical film as described in any one of <1> to <10>, including an optically anisotropic layer formed by the curing of a polymerizable composition containing the compound represented by General Formula (1), and further including a photo-alignment film, in which the optically anisotropic layer is directly in contact with the photo-alignment film.

<12> A polarizing plate including the optical film as described in any one of <1> to <11>.

<13> A circularly polarizing plate including the optical film as described in any one of <1> to <11>.

<14> A display apparatus including the optical film as described in any one of <1> to <11>.

<15> A compound represented by the following general formula (3):

General Formula (3)

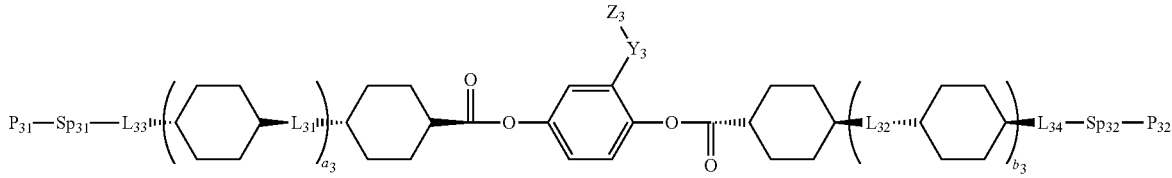

(in the formula,
$L_{31}$ and $L_{32}$ each independently represent a single bond, —CO—, —CO—O—, or —O—CO—,
$L_{33}$ and $L_{34}$ each independently represent a single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, or —NR$^{25}$—CO—NR$^{26}$—, and $R^{21}$ to $R^{26}$ each represent a hydrogen atom or an alkyl group having 1 to 6 carbon atoms, Sp$_{31}$ and Sp$_{32}$ each independently represent a spacer group, P$_1$ and P$_2$ each independently represent a polymerizable group, Y$_3$ represents a single bond or —R$^5$C=N—NR$^6$—, and R$^5$ and R$^6$ each independently represent a hydrogen atom or an alkyl group having 1 to 6 carbon atoms, Z$_3$ represents an aromatic group obtained by removing one hydrogen atom from an aromatic cyclic compound represented by any one of the following Z-1, Z-2, and Z-4, Q represents —O—, —S—, or —NR$^{17}$—, and R$^{17}$ represents a hydrogen atom or an alkyl group having 1 to 6 carbon atoms, and the aromatic cyclic compound represented by any one of the following Z-1, Z-2, and Z-4 may have a substituent, and a and b each independently represent an integer of 0 or 1.

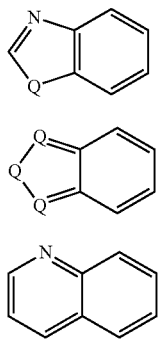

<16> The compound as described in <15>, in which a$_3$ and b$_3$ are 0, and the compound contains a hydrogen bond donating group and a hydrogen bond accepting group in the Y$_3$—Z$_3$ site.

<17> A method for producing the compound as described in <15> or <16>, including a step of monoesterifying 1,4-transcyclohexanedicarboxylic acid in accordance with a mixed acid anhydride process.

According to the present invention, an optical film exhibiting excellent reverse wavelength dispersion is provided. In addition, according to the present invention, a novel liquid crystal compound which can be used for production of a film exhibiting excellent reverse wavelength dispersion and can be easily synthesized is provided.

BRIEF DESCRIPTION OF THE DRAWING

FIG. 1 is a view illustrating a change in Re(λ)/Re(550) by each wavelength λ of optical films 1, 3, 12, and 21, prepared in Examples.

DESCRIPTION OF THE PREFERRED EMBODIMENTS

Hereinafter, the present invention will be described in detail. The description of the constituent elements that will be described below may be shown based on the representative embodiments of the present invention in some cases, but the present invention is not limited to such the embodiments. Further, in the present specification, a numerical range expressed by a wording "a number to another number" means a range that falls between the former number indicating the lowermost limit of the range and the latter number indicating the uppermost limit thereof. In addition, the terms "orthogonal" and "parallel" used herein with respect to angles are meant to include an error ranging from −10° to +10° from the exact angle, and the terms "the same" and "different" used herein with respect to angles can be judged depending on a difference that may or may not be less than 5°.

The "slow axis" as used in the present specification means a direction in which an in-plane refractive index is maximum, and the "polarizing plate" is meant to include both of a long polarizing plate and a polarizing plate cut to a size to be incorporated into a display apparatus, unless otherwise specifically noted. Further, "cut" as used herein is intended to include "punching-out", "cutting-out", and the like. In addition, in the present specification, a form including, in particular, a laminate of an optical film of the present invention or an ordinary λ/4 plate with a polarizing film is referred to as "circularly polarizing plate" in the "polarizing plate".

In addition, the organic EL display apparatus means an organic electroluminescent display apparatus.

In the present specification, the "inclination angle" (also referred to as a tilt angle) means an angle between an inclined liquid crystal and a layer plane, and also means a maximum angle of the angles between the direction of a maximum refractive index and a layer plane in a refractive-index ellipsoid of a liquid crystal compound. Accordingly, in the rod-shaped liquid crystal compound having positive optically anisotropy, a tilt angle means an angle between the long axis direction, that is, the director direction and the layer plane in a rod-shaped liquid crystal compound. Further, in the present invention, the "average tilt angle" means an average value of tilt angles from an angle on the upper interface to an angle on the lower interface of a phase difference layer.

The reverse wavelength dispersion in the present specification means a property that the absolute value of retardation further increases at a longer wavelength.

In the present specification, Re(λ) and Rth(λ) represent an in-plane retardation and a thickness-direction retardation, respectively, at a wavelength of λ. The Re(λ) is measured by making light having a wavelength of λ nm incident to a film in the normal direction of the film, using KOBRA 21ADH or WR (trade name, manufactured by Oji Scientific Instruments).

In the case where a film to be used for the measurement represents a uniaxial or biaxial refractive-index ellipsoid, the Rth(λ) of the film is calculated by the following method.

The Re(λ) of the film is measured around the in-plane slow axis (judged by KOBRA 21ADH or WR) as the inclination axis (rotational axis) (in the case where the film does not have a slow axis, then its rotational axis may be in any in-plane direction of the film), relative to the normal direction of the film up to +50 degrees from at intervals of 10 degrees, in 6 points in all with a light having a wavelength of λ nm applied in the inclined direction; and based on the retardation values thus measured, the estimated value of the mean refractive index, and the inputted film thickness value, the Rth(λ) is calculated by KOBRA 21ADH or WR.

In the above description, in the case where the film to be analyzed has a direction in which the retardation value is zero at a certain inclination angle, around the in-plane slow axis from the normal direction as the rotational axis, then the retardation value at the inclination angle larger than the inclination angle is changed to negative data, and then the Rth(λ) is calculated by KOBRA 21 ADH or WR.

Around the slow axis as the inclination angle (rotation angle) of the film (in the case where the film does not have a slow axis, then its rotational axis may be in any in-plane direction of the film), the retardation values are measured in any two inclined directions, and based on the retardation values thus measured, the estimated value of the mean refractive index, and the inputted film thickness value, the Rth also may be calculated according to the following equations (1) and (2):

[Equation 1]

$$Re(\theta) = \left[ nx - \frac{(ny \times nz)}{\left( \sqrt{\left\{ ny\sin\left(\sin^{-1}\left(\frac{\sin(-\theta)}{nx}\right)\right)\right\}^2 + \left\{ nz\cos\left(\sin^{-1}\left(\frac{\sin(-\theta)}{nx}\right)\right)\right\}^2} \right)} \right] \times \frac{d}{\cos\left\{\sin^{-1}\left\{\frac{\sin(-\theta)}{nx}\right\}\right\}}$$ Equation (1)

$$Rth = \left(\frac{nx + ny}{2} - nz\right) \times d$$ Equation (2)

In the equation, Re(θ) represents a retardation value in the direction inclined by an angle θ from the normal direction; nx represents a refractive index in the in-plane slow axis direction; ny represents a refractive index in the in-plane direction perpendicular to nx; and nz represents a refractive index in the direction perpendicular to nx and ny. d represents a thickness of the film.

In the case where the film to be analyzed is not expressed by a uniaxial or biaxial refractive-index ellipsoid, that is, the film does not have an optical axis, the Rth(λ) of the film is calculated by the following method.

The Re(λ) is measured around the in-plane slow axis (judged by KOBRA 21ADH or WR) as the inclination axis (rotational axis), relative to the normal direction of the film from −50 degrees up to +50 degrees at intervals of 10 degrees, in 11 points in all with a light having a wavelength of λ nm applied in the inclined direction; and based on the retardation values thus measured, the estimated value of the mean refractive index, and the inputted film thickness value, the Rth(λ) is calculated by KOBRA 21ADH or WR.

In the aforementioned measurement, the estimated value of the mean refractive index is available from values listed in catalogues of various optical films in Polymer Handbook (John Wiley & Sons, Inc.). Those having the mean refractive indices unknown can be measured using an Abbe refractometer. The values of mean refractive indices of the main optical films are listed below: cellulose acylate (1.48), cycloolefin polymer (1.52), polycarbonate (1.59), polymethyl methacrylate (1.49), and polystyrene (1.59). With KOBRA 21ADH or WR, nx, ny, and nz are calculated by the estimated value of these mean refractive indices and the film thickness. On the basis of nx, ny, and nz thus calculated, [Nz=(nx−nz)/(nx−ny)] is further calculated.

<<Optical Film>>

In the present specification, the optical film means a film that can be used for optical members, for example various optical elements such as various display apparatuses, light emitting devices, and polarizing plates. The optical film includes optically anisotropic layers. The optical film may further include, in addition to optically anisotropic layers, other functional layers such as a support, an alignment layer, and an adhesive layer.

The optical film preferably has a thickness of, for example, 200 μm or less, 100 μm or less, 60 μm or less, 40 μm or less, 25 μm or less, 10 μm or less, or 5 μm or less.

Further, the optical film may be any thickness of 0.1 μm or more, or 1 μm or more.

[Optically Anisotropic Layer]

The optical film includes an optically anisotropic layer. The optically anisotropic layer is a layer having one wavelength and incidence direction with a retardation not being 0 when the retardation is measured in the in-plane direction or thickness direction, that is, a layer having an optical property that is not isotropic. The thickness of the optically anisotropic layer varies depending on the materials used or the phase difference value to be set, but is preferably from 0.1 μm to 20 μm, more preferably from 0.5 μm to 15 μm, and still more preferably from 1.0 μm to 10 μm. In addition, the preferable range of the in-plane retardation Re(550) varies depending on the uses at a wavelength of 550 nm of the optically anisotropic layer.

The optically anisotropic layer in the optical film may be either a layer including an optically anisotropic layer containing the compound represented by the following general formula (1), or an optically anisotropic layer formed by the curing of a polymerizable composition containing a compound represented by the following general formula (1).

<<Compound Represented by General Formula (1)>>

General Formula (1)

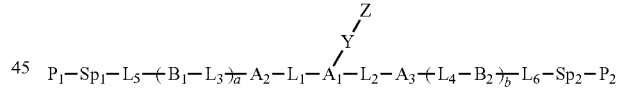

In General Formula (1), $L_1$ to $L_6$ each independently represent a single bond or a linking group, and $A_1$ represents an aromatic group which may have a substituent;

$A_2$ and $A_3$ each independently represent a cyclic aliphatic group which may have a substituent;

$B_1$ and $B_2$ each independently represent a cyclic aliphatic group which may have a substituent;

$Sp_1$ and $Sp_2$ each independently represent a spacer group;

$P_1$ and $P_2$ each independently represent a polymerizable group, an alkyl group, or a hydrogen atom;

Y represents a single bond or a linking group;

Z represents an aromatic group which may have a substituent; and a and b each independently represent any one integer of 0 to 2.

When it is described that a substituent may be contained in the present specification, the number and kind of the substituents, or the substitution position is not limited, and in the case where 2 or 3 substituents are present, the substituents may be the same as or different from each other.

The kind of the substituent is not particularly limited. Examples of the substituent include an alkyl group, an alkoxy group, an alkyl-substituted alkoxy group, a cyclic alkyl group, aryl groups such as a phenyl group and a naphthyl group, a cyano group, an amino group, a nitro group, an alkylcarbonyl group, a sulfo group, and a hydroxyl group. In particular, the substituent which may be contained in the aromatic group represented by Z may be a substituent obtained by removing Z from General Formula (1). Further, Z may also be a group obtained by removing Z—Y— from General Formula (1). That is, General Formula (1) may also correspond to a compound represented by the following general formula (11) or (12).

pound may be either a monocyclic compound or a fused ring compound containing 2 or more rings. Further, the cyclic compound may contain a ring constituted with carbon atoms alone or a ring constituted with atoms other than carbon atoms. Specific examples of the atoms other than carbon atoms include a nitrogen atom, a sulfur atom, and an oxygen atom, and may contain one or two atoms selected from the atoms. The total number of carbon atoms or atoms other than carbon atoms, constituting a ring, is not particularly limited, but may be about from 5 to 18, preferably from 5 to 14, and more preferably from 5 to 10.

The aromatic group represented by $A_1$ is preferably an aryl group, and specific examples of the aryl group include a phenyl group and a naphthyl group.

General Formula (11)

$$P_1-Sp_1-L_5-(B_1-L_3)_a-A_2-L_1-A_1-L_2-A_3-(L_4-B_2)_b-L_6-Sp_2-P_2$$
$$\quad\quad\quad\quad\quad\quad\quad\quad\quad\quad\quad\quad\quad\quad\quad\quad\quad Y$$
$$\quad\quad\quad\quad\quad\quad\quad\quad\quad\quad\quad\quad\quad\quad\quad\quad\quad Z$$
$$\quad\quad\quad\quad\quad\quad\quad\quad\quad\quad\quad\quad\quad\quad\quad\quad\quad Y$$
$$P_1-Sp_1-L_5-(B_1-L_3)_a-A_2-L_1-A_1-L_2-A_3-(L_4-B_2)_b-L_6-Sp_2-P_2$$

General Formula (12)

$$P_1-Sp_1-L_5-(B_1-L_3)_a-A_2-L_1-A_1-L_2-A_3-(L_4-B_2)_b-L_6-Sp_2-P_2$$
$$\quad\quad\quad\quad\quad\quad\quad\quad\quad\quad\quad\quad\quad\quad\quad\quad\quad Y$$
$$P_1-Sp_1-L_5-(B_1-L_3)_a-A_2-L_1-A_1-L_2-A_3-(L_4-B_2)_b-L_6-Sp_2-P_2$$

$L_1$ to $L_6$ each independently represent a single bond or a linking group.

The "linking group" represented by each of $L_1$ to $L_6$ represents a divalent group formed by a series of 1 to 5 atoms, or preferably 1 to 3 atoms selected from carbon atoms, oxygen atoms, nitrogen atoms, sulfur atoms, and the like. Examples of the "linking group" include —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, and —NR$^{25}$—CO—NR$^{26}$— (in which $R^{21}$ to $R^{26}$ all represent a hydrogen atom or an alkyl group having 1 to 6 carbon atoms), —R$^1$C=CR$^{11}$—, —R$^2$C=N—, —N=N—, —CO—NR$^3$—, —NR$^4$—CO—, —R$^5$C=N—NR$^6$—, —CO—NR$^7$—NR$^8$—, —R$^9$C=N—S—, —CO—NR$^{10}$—S—, —CO—S—, —R$^{11}$C=N—N=, and R$^{12}$C=C—NR$^{13}$— (in which $R^1$ to $R^{10}$, $R^{12}$, and $R^{13}$ each independently represent a hydrogen atom or an alkyl group having 1 to 6 carbon atoms, and $R^{11}$ represents a hydrogen atom, an ester group, an acyl group, or a cyano group).

The connection direction in the linking groups is such that an element described on the left side (for example, "O" in "—O—CO—") is bonded to an element on the $P_1$ side of General Formula (1).

$L_1$ and $L_2$ are preferably —CO—, —CO—O—, or —O—CO—.

$L_3$, $L_4$, $L_5$, and $L_6$ are each preferably —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, or —NR$^{25}$—CO—NR$^{26}$—.

$A_1$ represents an aromatic group which may have a substituent.

The aromatic group represented by $A_1$ may be a group formed by removing one, two, or three hydrogen atoms from an aromatic cyclic compound. The aromatic cyclic com- $A_1$ is preferably a group formed by removing three hydrogen atoms from an unsubstituted benzene ring or naphthalene ring, and specifically, it is preferably a trivalent aromatic group represented by the following A1-1, A1-2, or A1-3. *1, *2, and *Y each represent a bonding position with L1, L2, or Y. The trivalent aromatic group represented by the following A1-1, A1-2, or A1-3 may or may not have a substituent, but preferably, it does not have a substituent.

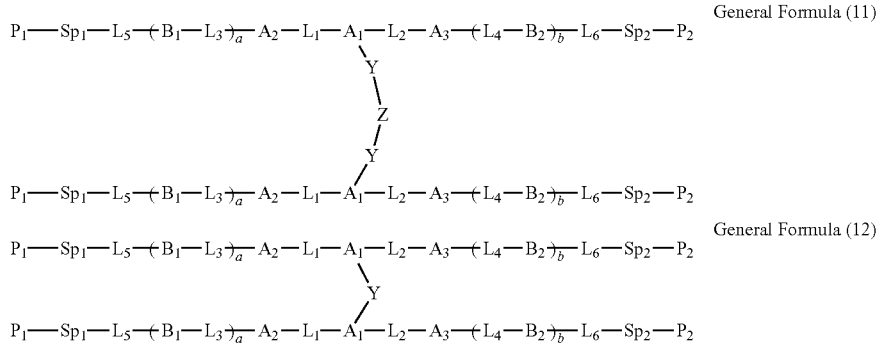

A1-1

A1-2

A1-3

$A_2$ and $A_3$ each independently represent a cyclic aliphatic group which may have a substituent.

The cyclic aliphatic group represented by $A_2$ or $A_3$ may be any divalent group obtained by removing two hydrogen atoms from cyclic alkane, and may have a part of carbon atoms substituted with atoms other carbon atoms as described above (for example, hetero atoms). The total number of carbon atoms or atoms other than carbon atoms, of the cyclic alkane forming the cyclic aliphatic group, is preferably from 3 to 10, and more preferably from 3 to 7. Examples of the cyclic alkane include cyclopropane, cyclobutane, cyclopentane, cyclohexane, and cycloheptane.

Specifically, the cyclic aliphatic group represented by $A_2$ or $A_3$ is preferably a cycloalkylene group having 3 to 7 carbon atoms, which may have a substituent; more preferably a divalent group which may have a substituent, obtained by removing two hydrogen atoms from cyclohexane; still more preferably a 1,4-cyclohexylene group which may have a substituent; particularly preferably a trans-1,4-cyclohexylene group which may have a substituent; and most preferably an unsubstituted trans-1,4-cyclohexylene group.

The cyclic aliphatic groups are each independently preferably a cycloalkylene group having 3 to 10 carbon atoms (in which a part of carbon atoms may be substituted with hetero atoms), which may have a substituent; more preferably a cycloalkylene group having 3 to 7 carbon atoms, which may have a substituent; still preferably a trans-1,4-cyclohexylene group; and particularly preferably an unsubstituted trans-1,4-cyclohexylene group.

$B_1$ and $B_2$ each independently represent a divalent cyclic aliphatic group which may have a substituent, or a divalent aromatic group which may have a substituent.

In the case where $B_1$ and $B_2$ are each a divalent cyclic aliphatic group which may have a substituent, the definition thereof has the same meanings as for the cyclic aliphatic group represented by $A_2$ and $A_3$, and the preferred ranges thereof are also the same as for the cyclic aliphatic groups represented by $A_2$ and $A_3$. $B_1$ and $B_2$ are each preferably a cycloalkylene group having 3 to 10 carbon atoms (in which a part of carbon atoms may be substituted with hetero atoms), which may have a substituent; more preferably a cycloalkylene group having 3 to 7 carbon atoms, which may have a substituent; still more preferably a trans-1,4-cyclohexylene group; and particularly preferably an unsubstituted trans-1,4-cyclohexylene group.

In the case where $B_1$ and $B_2$ are each an aromatic group which may have a substituent, the definition thereof has the same meanings as for the aromatic group represented by $A_1$. $B_1$ and $B_2$ are each preferably a divalent aromatic group formed by removing hydrogen atoms from benzene or naphthalene which may have a substituent; more preferably a 1,4-phenylene group which may have a substituent; and particularly preferably an unsubstituted 1,4-phenylene group. In the case where two or more types of the compound represented by General Formula (1) are used for forming an optical film, it is preferable that a compound where $B_1$ and $B_2$ in General Formula (1) each independently represent a divalent cyclic aliphatic group which may have a substituent and a compound where $B_1$ and $B_2$ in General Formula (1) each independently represent a divalent aromatic group which may have a substituent are used in combination.

$Sp_1$ and $Sp_2$ each independently represent a spacer group.

The "spacer group" means a group connecting a site linked with a cyclic group in the compound represented by General Formula (1) to an end part such as a polymerizable group. The spacer group is not particularly limited, but examples thereof include an alkylene group having 2 to 12 carbon atoms or an alkylene oxide group having 2 to 12 carbon atoms. The alkylene group or the alkylene moiety of alkylene oxide group may be linear or branched.

Specific examples of the spacer group include —$(CH_2)_n$—, —$(CH_2)_n$—O—, —$(CH_2$—O—$)_n$—, and —$(CH_2CH_2$—O—$)_m$. n represents an integer of 2 to 12, and m represents an integer of 2 to 6.

Specifically, $Sp_1$ and $Sp_2$ are each preferably —$(CH_2)_n$—O— as described above, and among these, a case where n represents an integer of 2 to 6 is more preferable.

$P_1$ and $P_2$ each independently represent a polymerizable group, an alkyl group, or a hydrogen atom.

The polymerizable group represented by $P_1$ and $P_2$ is not particularly limited, but is preferably a polymerizable group capable of radical polymerization or cationic polymerization. As the polymerizable group capable of radical polymerization, a generally known radically polymerizable group can be used, and suitable examples thereof include ethylenically unsaturated groups, and among these, a (meth)acryloyl group is preferable. It is known that an acryloyl group generally has a high polymerization speed, and from the viewpoint of improvement of productivity, an acryloyl group is preferable, but a methacryloyl group can be equivalently used as a polymerizable group of a high-birefringence liquid crystal. As the polymerizable group capable of cationic polymerization, a generally known cationically polymerizable group can be used, and suitable examples thereof include ring-opening polymerizable groups. The ring-opening polymerizable group is preferable since it has less contraction due to polymerization and can inhibit the layers from being closer to each other. Specific examples of the ring-opening polymerizable group include an alicyclic ether group, a cyclic acetal group, a cyclic lactone group, a cyclic thioether group, a spiro orthoester group, and a vinyl group. Among these, an alicyclic ether group and a vinyl group are suitable, and an epoxy group, an oxetanyl group, and a vinyl group are particularly preferable.

Particularly preferable examples of the polymerizable group represented by $P_1$ and $P_2$ include the following groups.

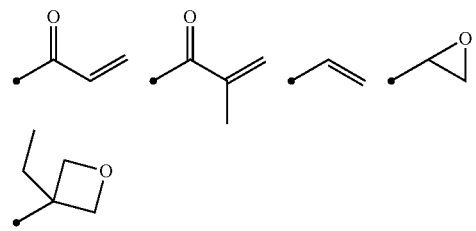

The alkyl group represented by $P_1$ and $P_2$ may be either linear or branched. The number of carbon atoms of the alkyl group is preferably from 1 to 30, more preferably from 1 to 10, and particularly preferably from 1 to 6. Examples of the alkyl group include a methyl group, an ethyl group, an n-propyl group, an isopropyl group, an n-butyl group, an isobutyl group, a sec-butyl group, a tert-butyl group, an n-pentyl group, an isopentyl group, a neopentyl group, a 1,1-dimethylpropyl group, an n-hexyl group, an isohexyl group, a linear or branched heptyl group, an octyl group, a nonyl group, a decyl group, an undecyl group, and a dodecyl group. The above description of the alkyl group shall apply to the alkyl group in the alkoxy group containing an alkyl group, an alkyl-substituted alkoxy group, or an alkylcarbonyl group.

$P_1$ and $P_2$ are all preferably polymerizable groups, and particularly preferably acryloyl groups.

Y represents a single bond or a linking group.

In the case where Y is a linking group, the definition thereof is the same as for the linking group represented by $L_1$ to $L_6$. Y is preferably a single bond or —$R^5C$=N—$NR^6$—.

Z represents an aromatic group which may have a substituent, and the definition thereof is the same as for the aromatic group represented by $A_1$. Z is preferably an aromatic group obtained by removing one or two hydrogen atoms from an aromatic cyclic compound represented by any one of the following Z-1 to Z-7. The number of the hydrogen atoms to be removed may be one in the case where the hydrogen atoms are bonded to Y through a single bond, but it may also be 2 in the case where the hydrogen atoms are bonded to Y through a double bond. In the following Z-1 to Z-7, Q represents —O—, —S—, or —$NR^{17}$—, $R^{17}$ represents a hydrogen atom or an alkyl group having 1 to 6 carbon atoms, and the aromatic group represented by any one of the following Z-1 to Z-7 may have a substituent. As the substituent, a methyl group, a methoxy group, and the like are preferable, but the aromatic groups having no substituent are more preferable.

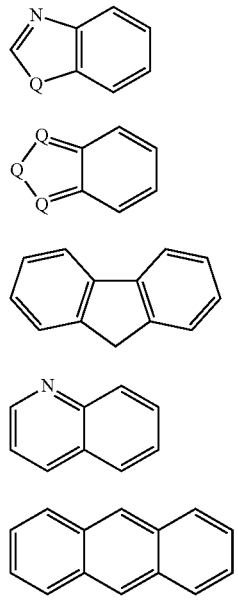

Z-1

Z-2

Z-3

Z-4

Z-5

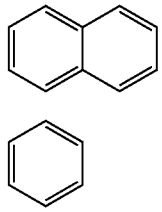

Z-6

Z-7

In the case where an aromatic group represented by any one of the following Z-1 to Z-7 has a substituent, it is preferably, for example, a substituent shown below.

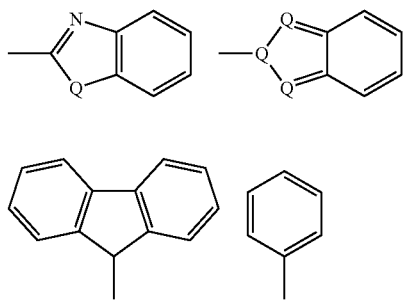

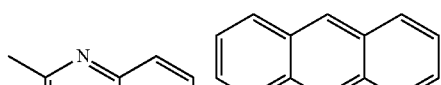

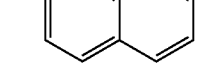

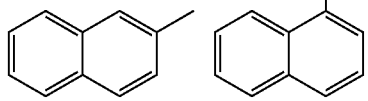

It is preferable that the Y—Z site has a hydrogen bonding substituent from the viewpoint of improving the liquid crystal expression. The hydrogen bonding substituent will be described later.

a and b are each independently preferably 0 or 1 from the viewpoints of solubility and convenience of synthesis.

A preferable example of the compound represented by General Formula (1) contains a compound where $A_2$, $A_3$, $B_1$, and $B_2$ are each a trans-1,4-cyclohexylene group.

The compound represented by General Formula (1) is particularly preferably a compound represented by General Formula (3).

General Formula (3)

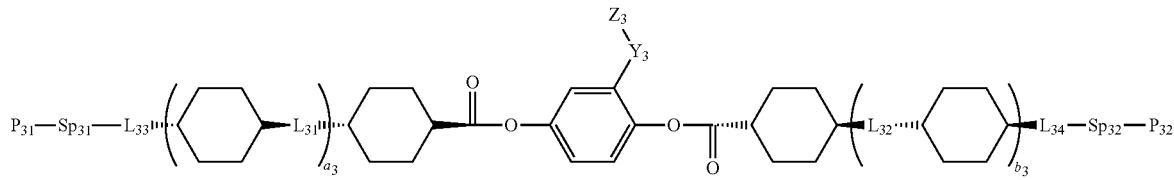

In General Formula (3), $L_{31}$ and $L_{32}$ each independently represent a single bond, —CO—, —CO—O—, or —O—CO—;

$L_{33}$ and $L_{34}$ each independently represent a single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, or —NR$^{25}$—CO—NR$^{26}$—, and $R^{21}$ to $R^{26}$ all represent a hydrogen atom or an alkyl group having 1 to 6 carbon atoms;

$Sp_{31}$ and $Sp_{32}$ each represent a spacer group;

$P_{31}$ and $P_{32}$ each independently represent a polymerizable group;

Y represents a single bond or —R$^5$C═N—NR$^6$—, and $R^5$ and $R^6$ each independently represent a hydrogen atom or an alkyl group having 1 to 6 carbon atoms;

$Z_3$ represents an aromatic group obtained by removing one hydrogen atom from an aromatic cyclic compound represented by any one of the following Z-1, Z-2, and Z-4, Q represents —O—, —S—, or —NR$^{17}$—, $R^{17}$ represents a hydrogen atom or an alkyl group having 1 to 6 carbon atoms, the aromatic cyclic compound represented by any one of the following Z-1, Z-2, and Z-4 may have a substituent, and a and b each independently represent an integer of 0 or 1.

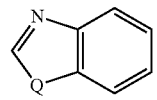

Z-1

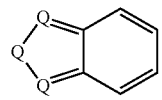

Z-2

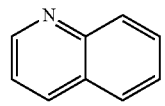

Z-4

Specific examples of the compound represented by General Formula (1) are as follows, but the compound represented by General Formula (1) is not limited to the following examples.

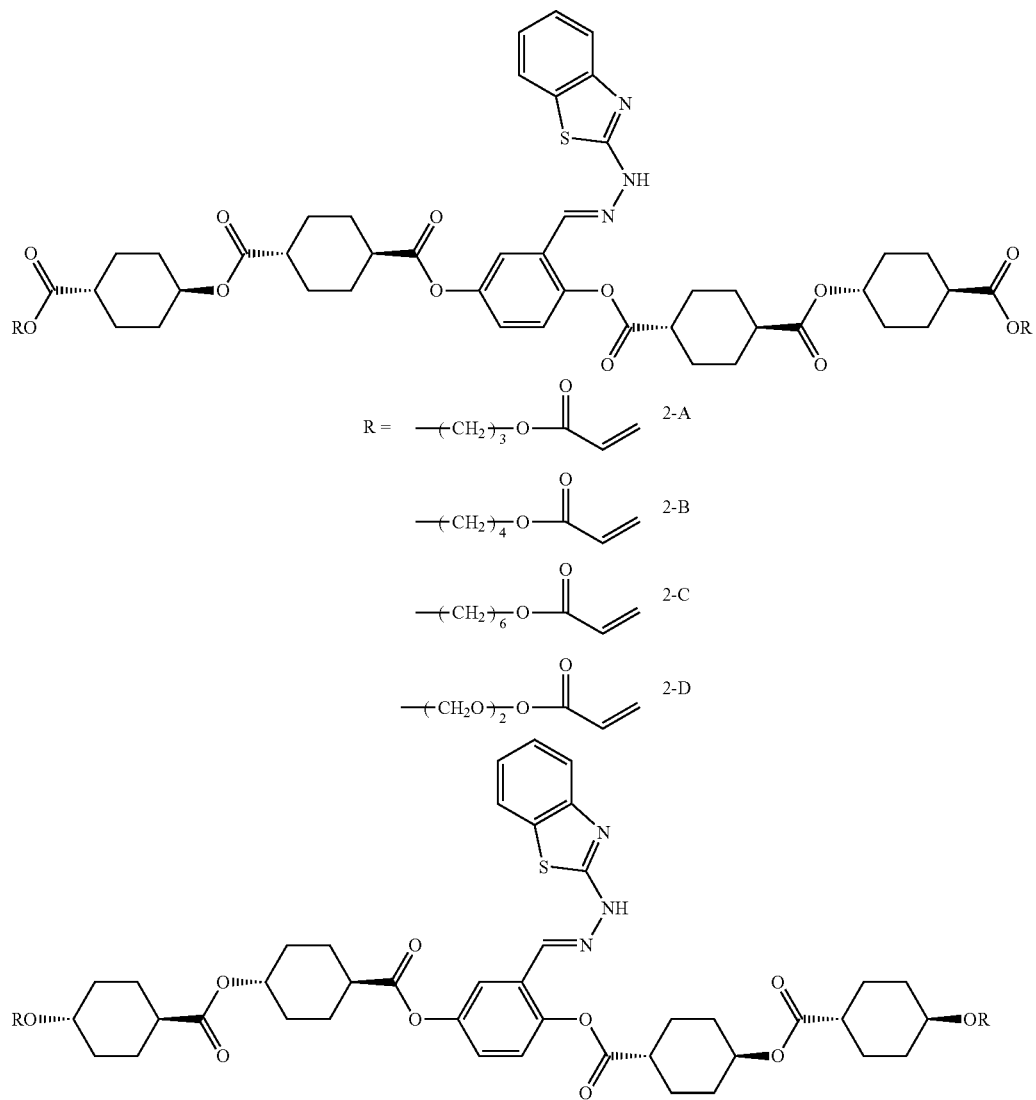

-continued
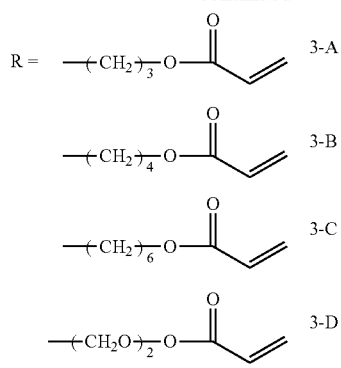
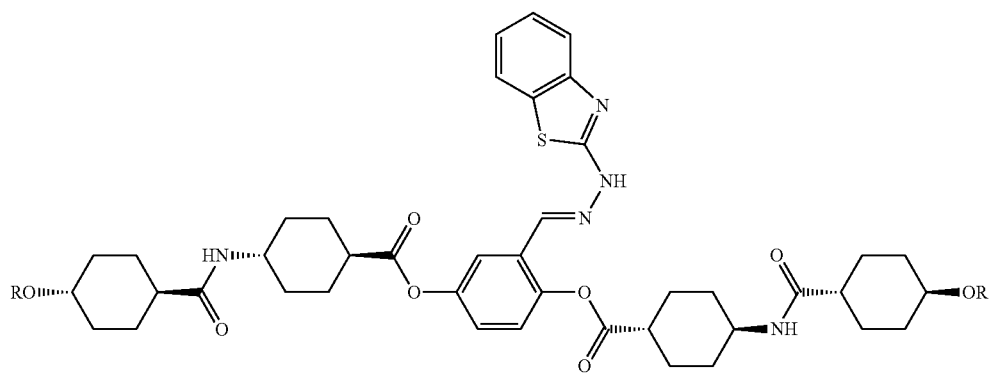
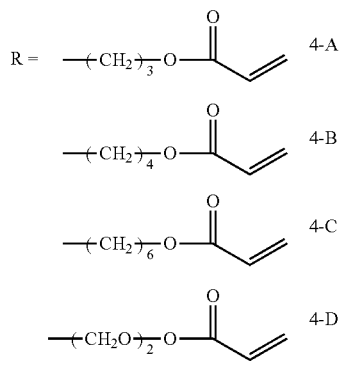
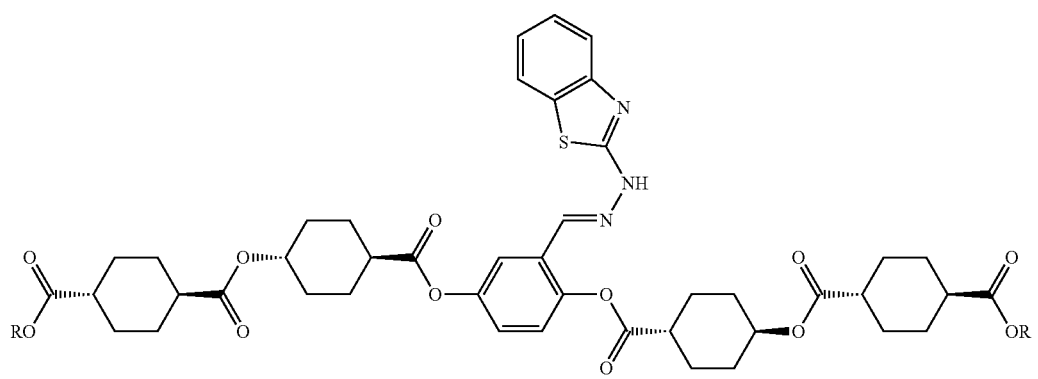

-continued
R = 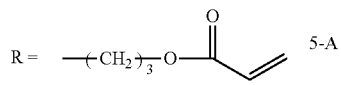 5-A
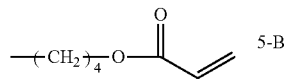 5-B
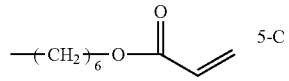 5-C
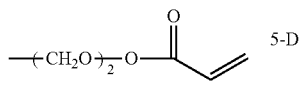 5-D
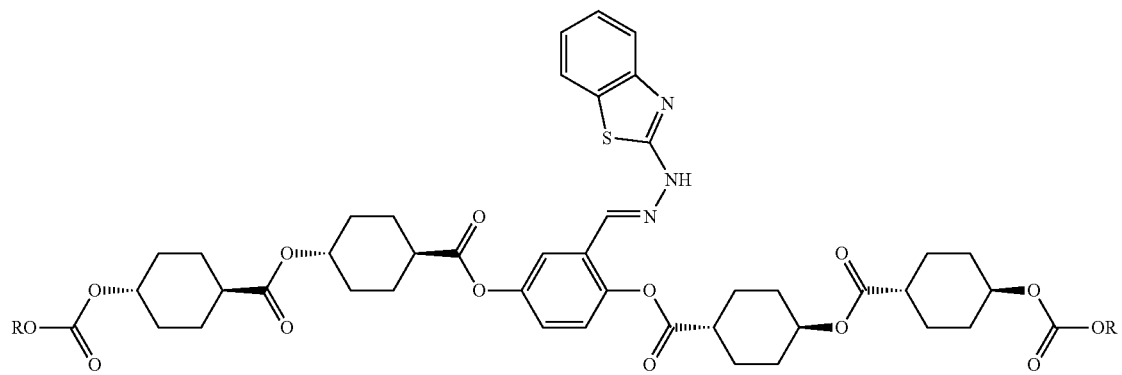
R = 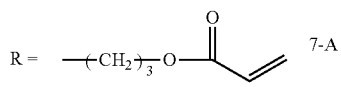 7-A
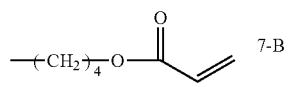 7-B
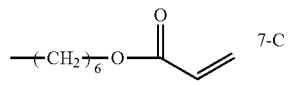 7-C
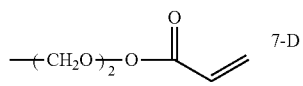 7-D
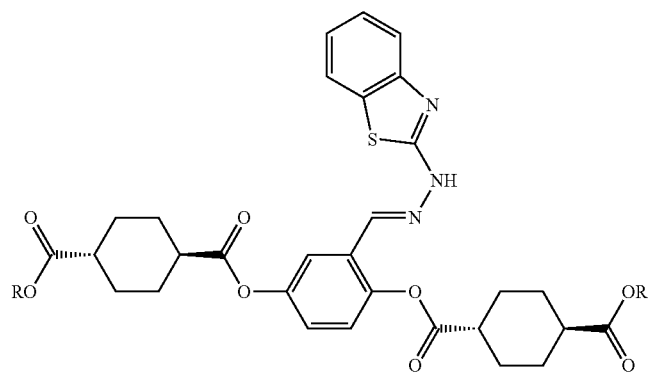

-continued
R = 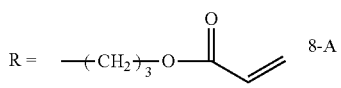 8-A
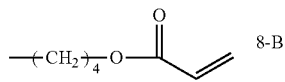 8-B
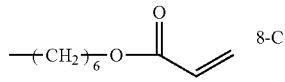 8-C
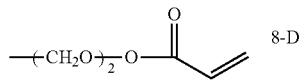 8-D
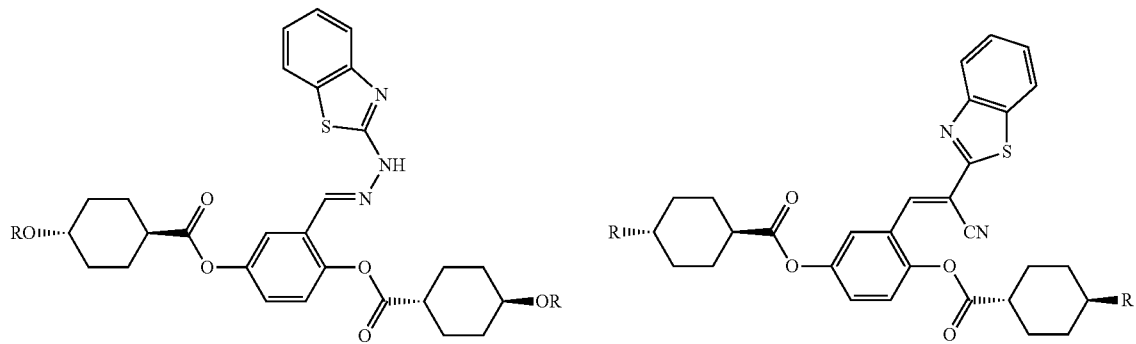
R = 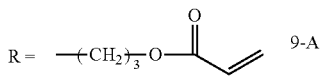 9-A
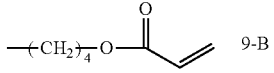 9-B
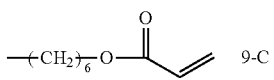 9-C
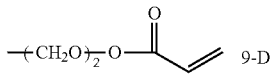 9-D
R = 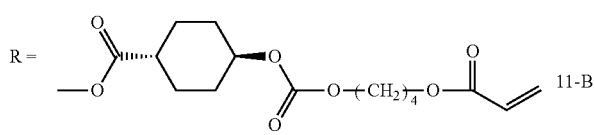 11-B
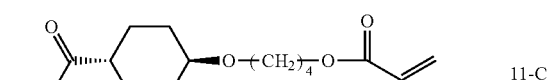 11-C
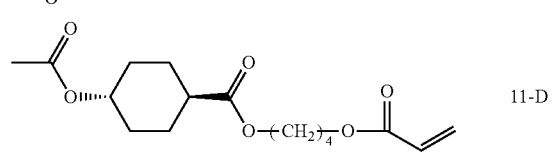 11-D
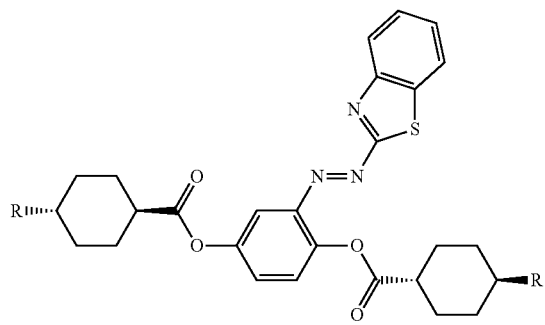
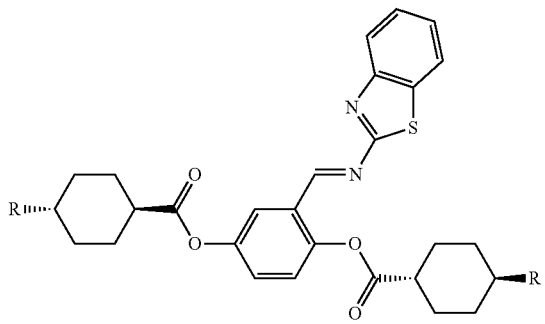

-continued
R = 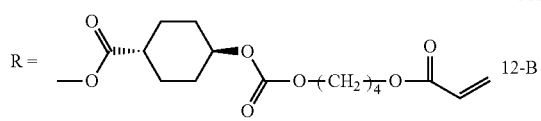 12-B
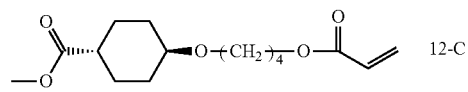 12-C
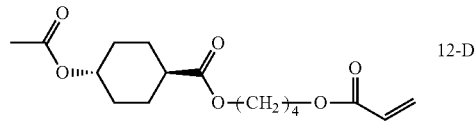 12-D
R = 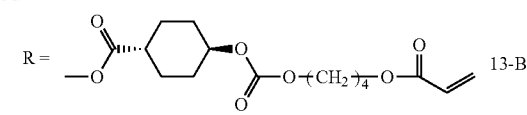 13-B
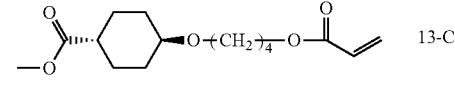 13-C
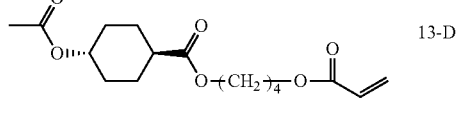 13-D
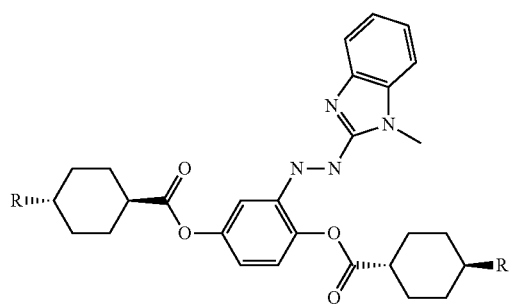
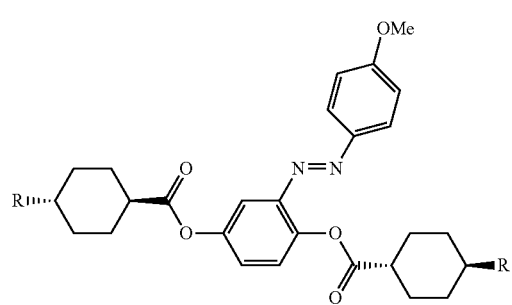
R = 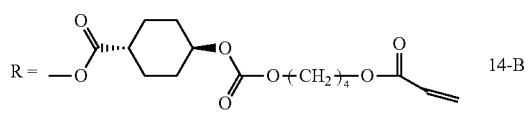 14-B
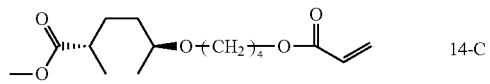 14-C
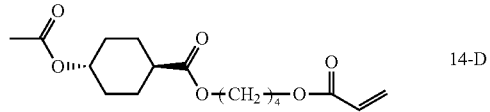 14-D
R = 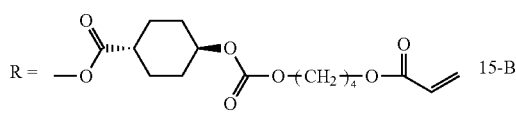 15-B
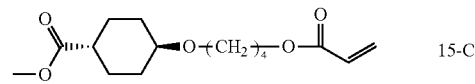 15-C
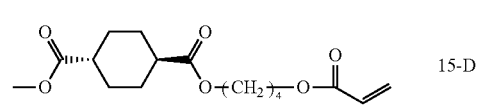 15-D
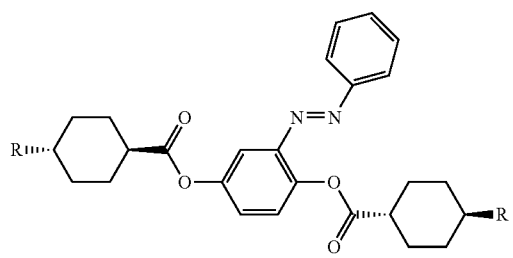
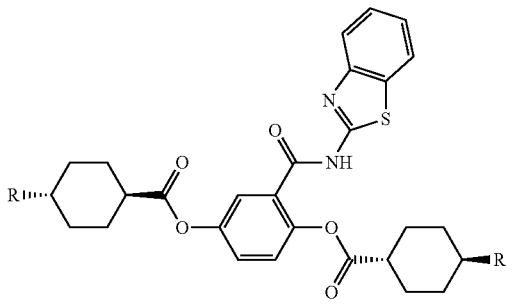
R = 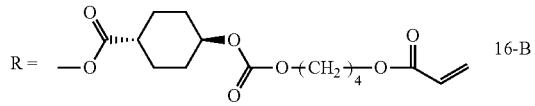 16-B
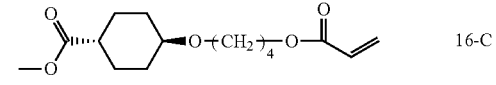 16-C
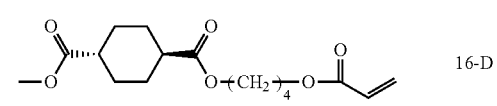 16-D
R = 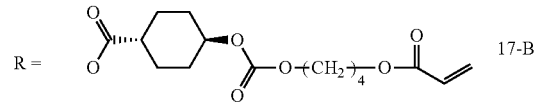 17-B
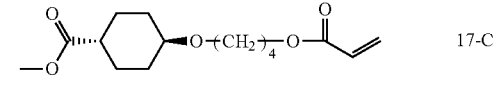 17-C
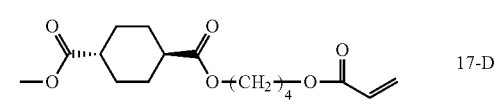 17-D -continued
| 25 | 26 |
|---|---|
| 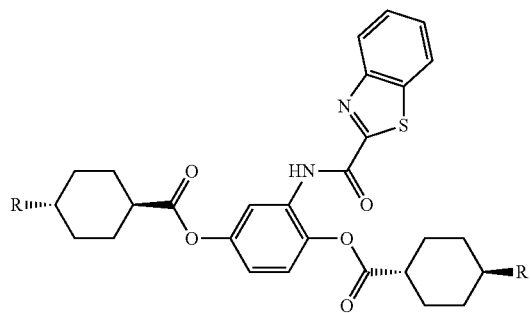 | 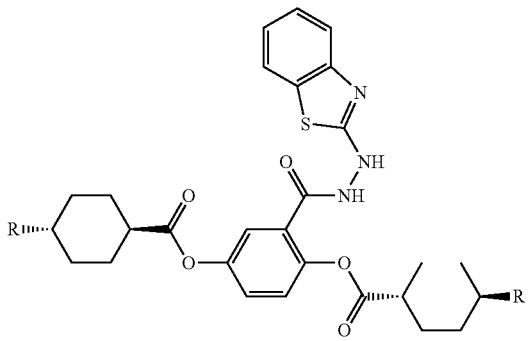 |
| R = 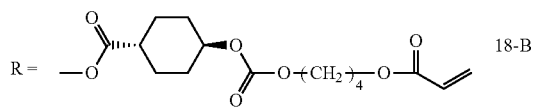 18-B | R = 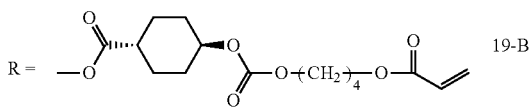 19-B |
| 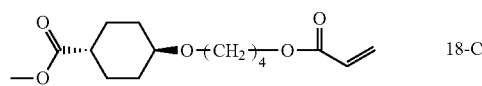 18-C | 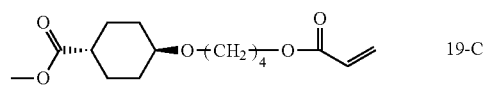 19-C |
| 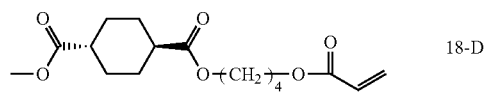 18-D | 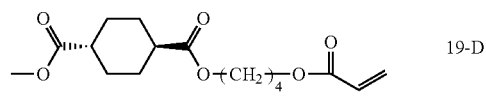 19-D |
| 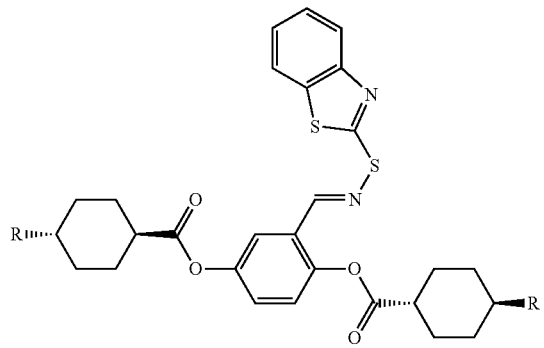 | 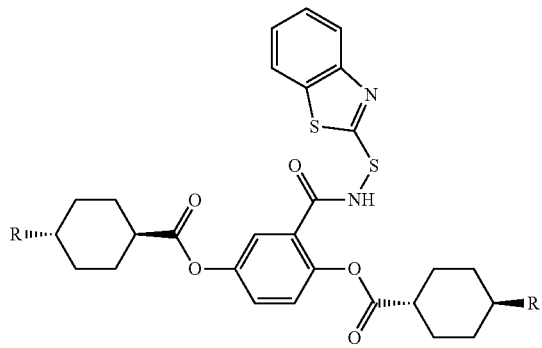 |
| R = 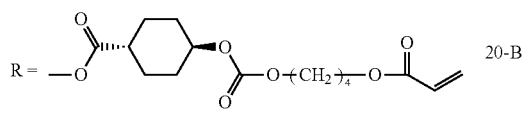 20-B | R = 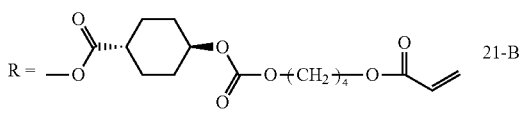 21-B |
| 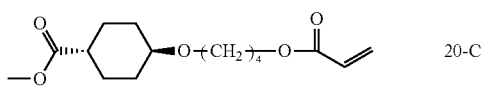 20-C | 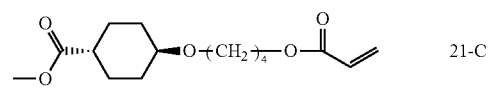 21-C |
| 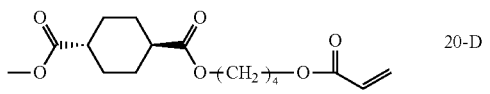 20-D | 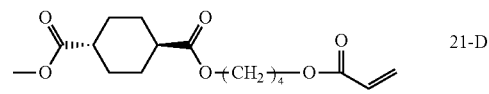 21-D |
| 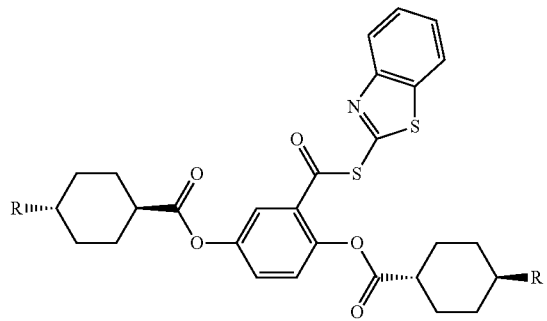 | 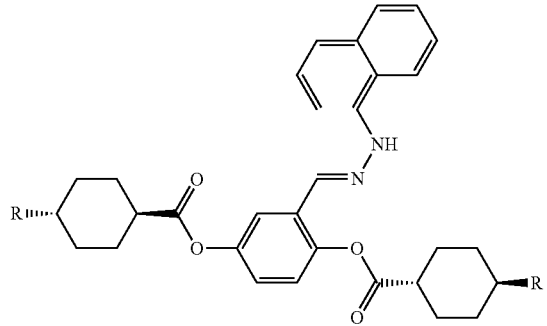 |

-continued
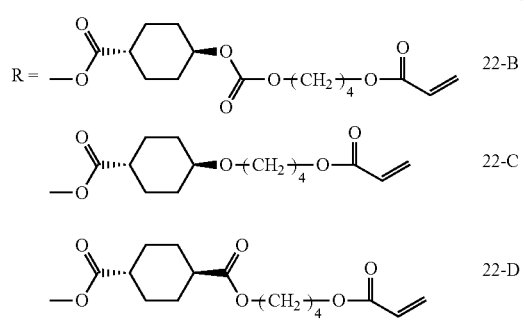
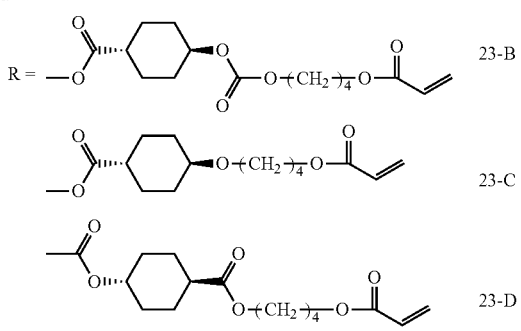
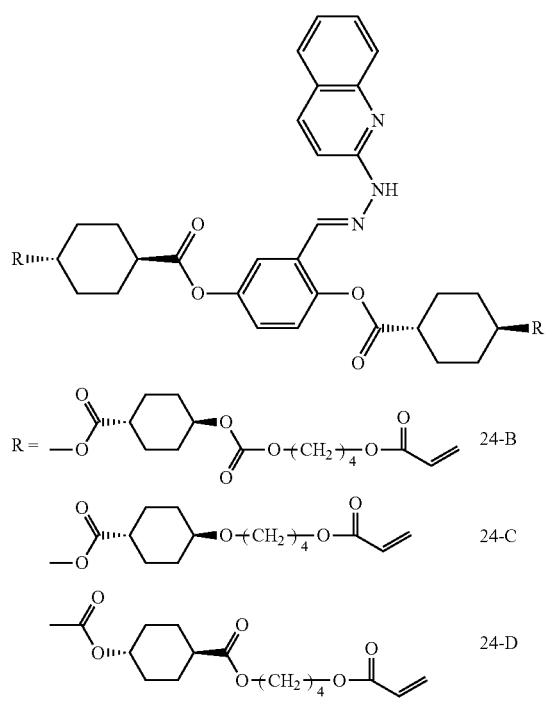
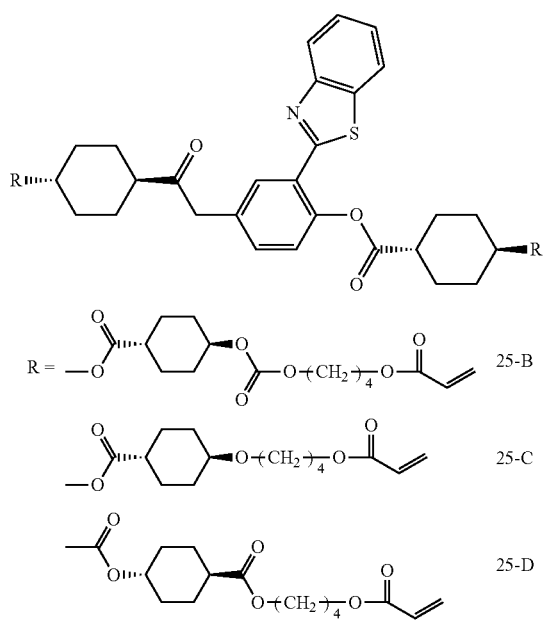
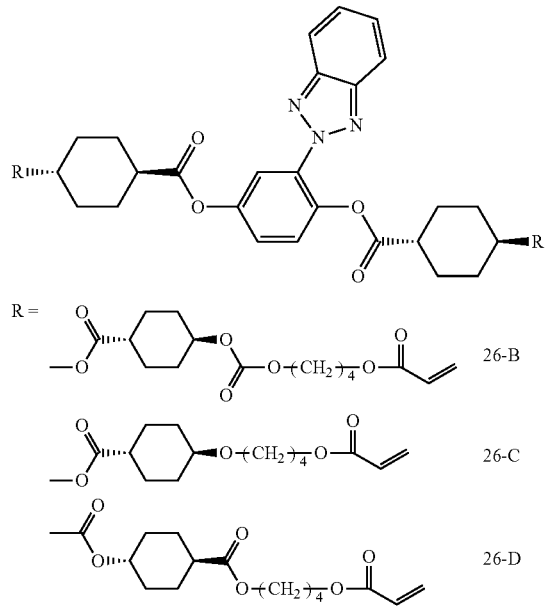
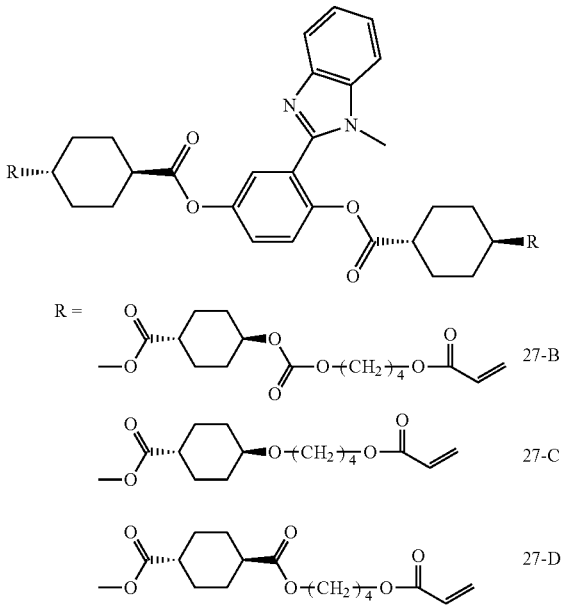

-continued
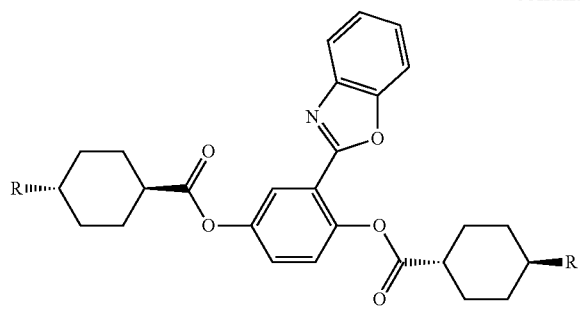
R =
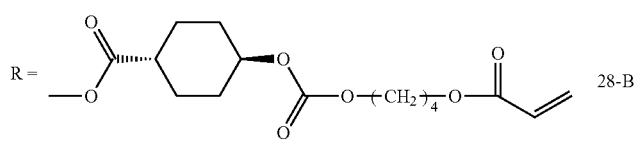 28-B
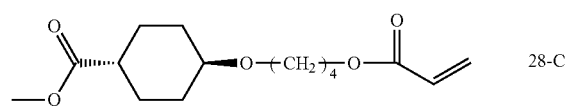 28-C
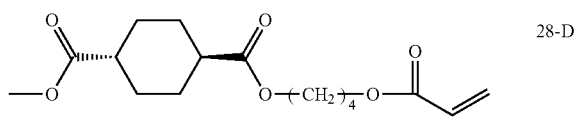 28-D
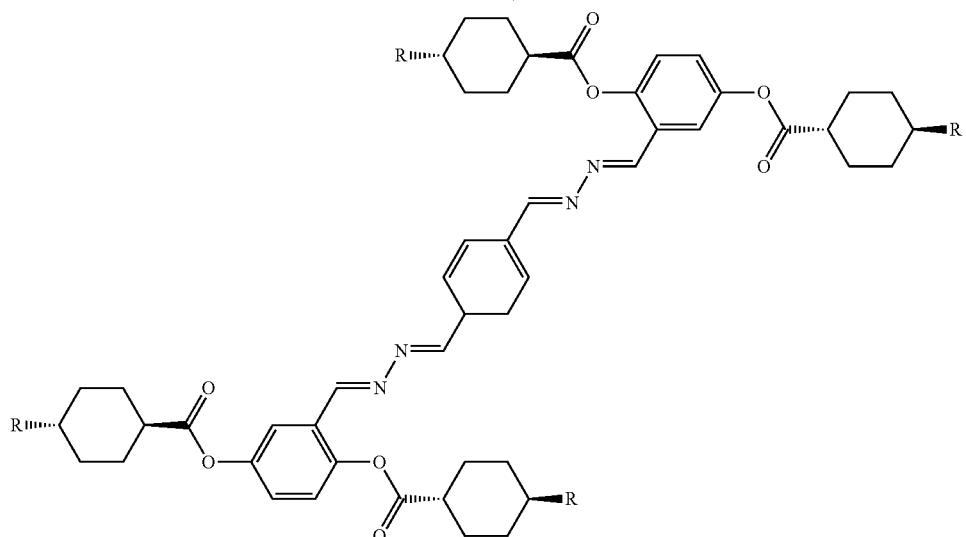
R =
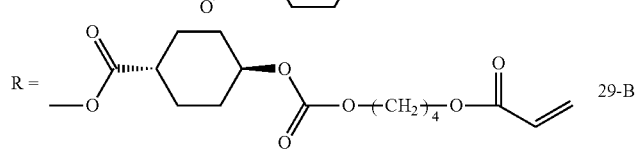 29-B
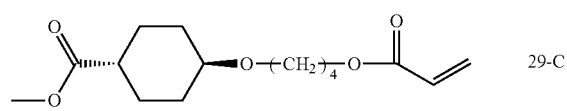 29-C
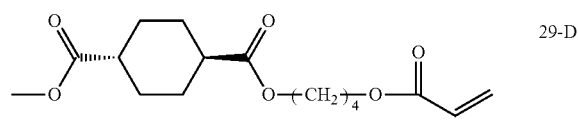 29-D -continued
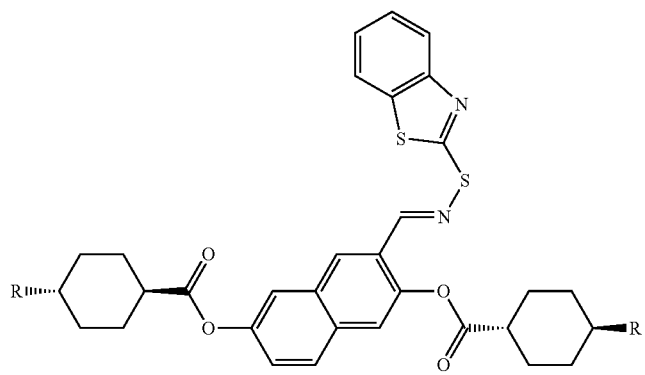
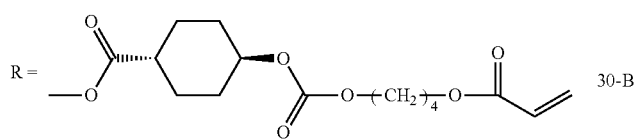
30-B
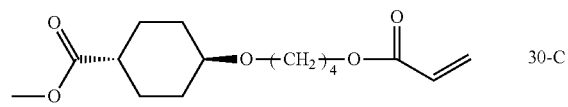
30-C
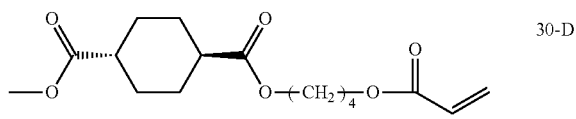
30-D
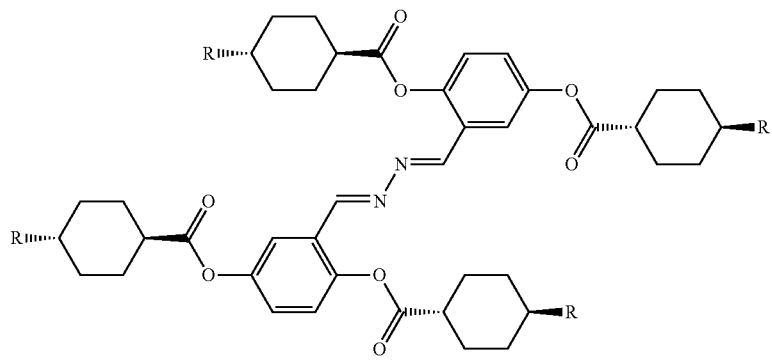
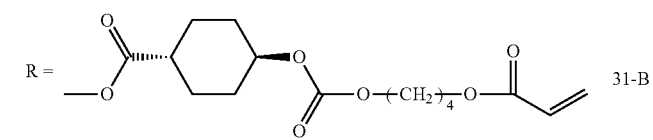
31-B
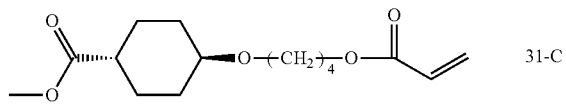
31-C
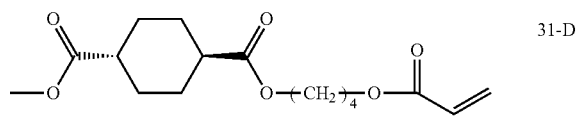
31-D -continued
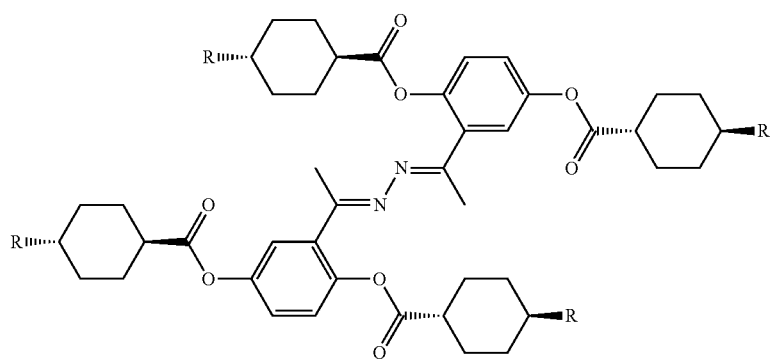
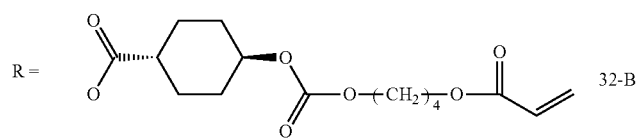 32-B
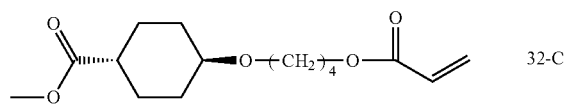 32-C
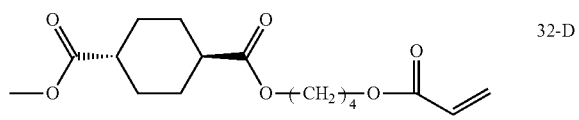 32-D
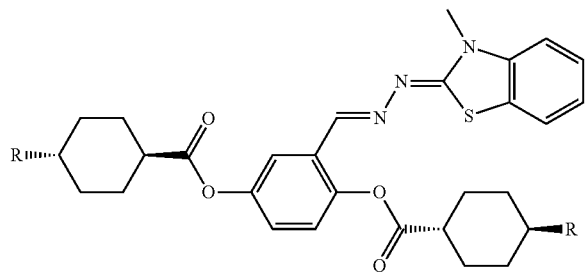
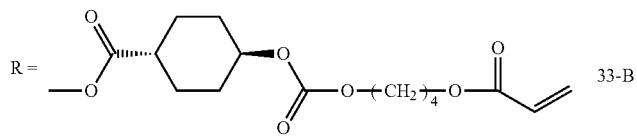 33-B
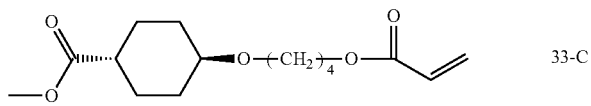 33-C
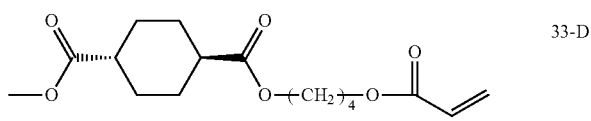 33-D -continued
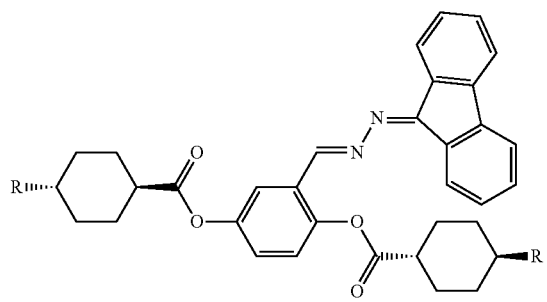
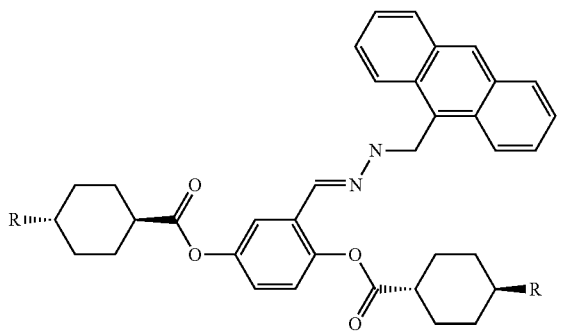
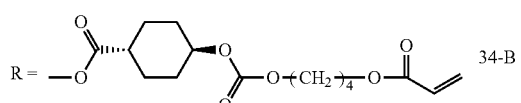 34-B
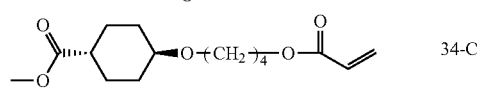 34-C
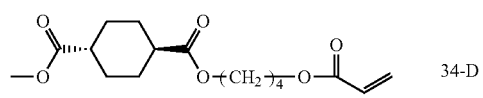 34-D
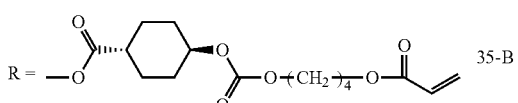 35-B
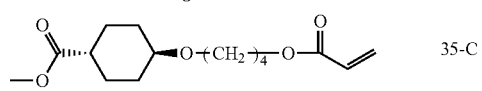 35-C
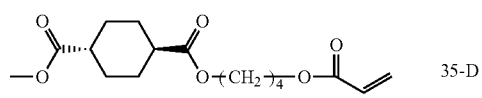 35-D
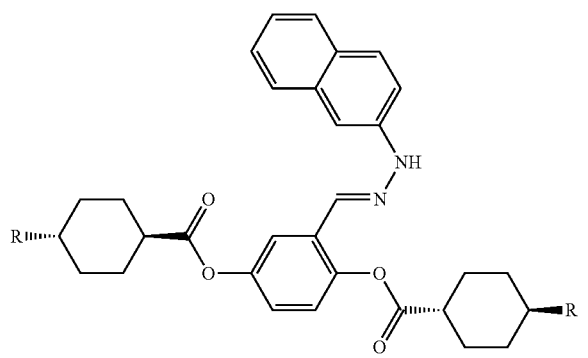
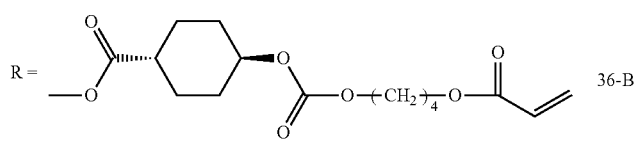 36-B
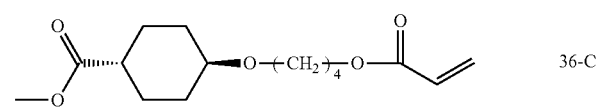 36-C
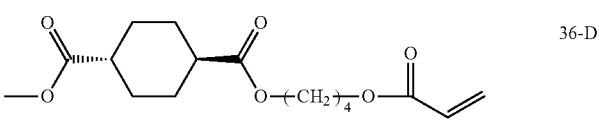 36-D
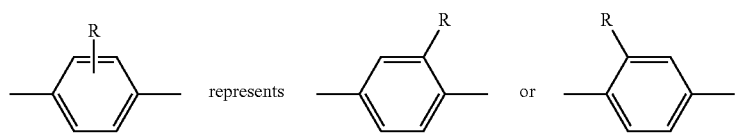

-continued
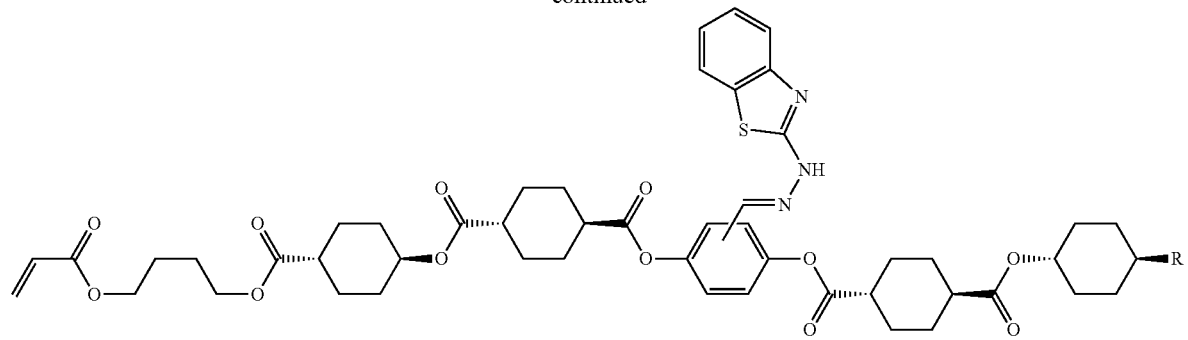
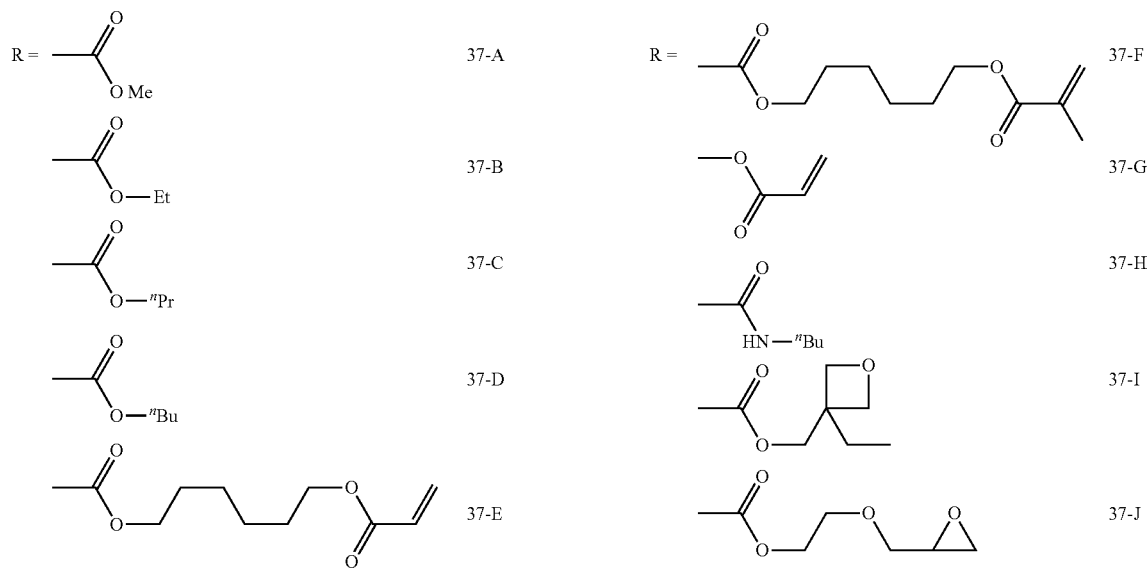
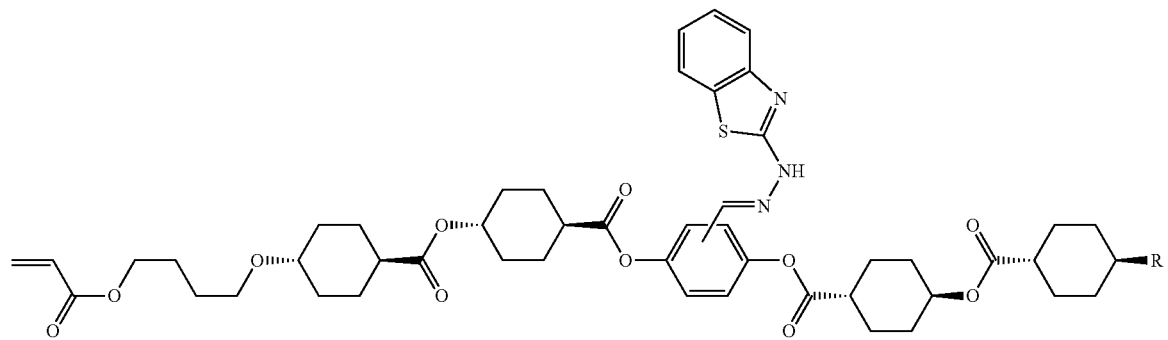

-continued
R = 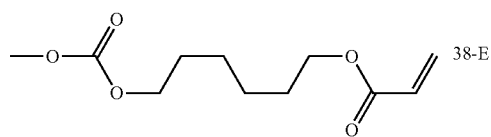 38-A
—O—Me  38-A
—O—Et  38-B
—O—$^n$Pr  38-C
—O—$^n$Bu  38-D
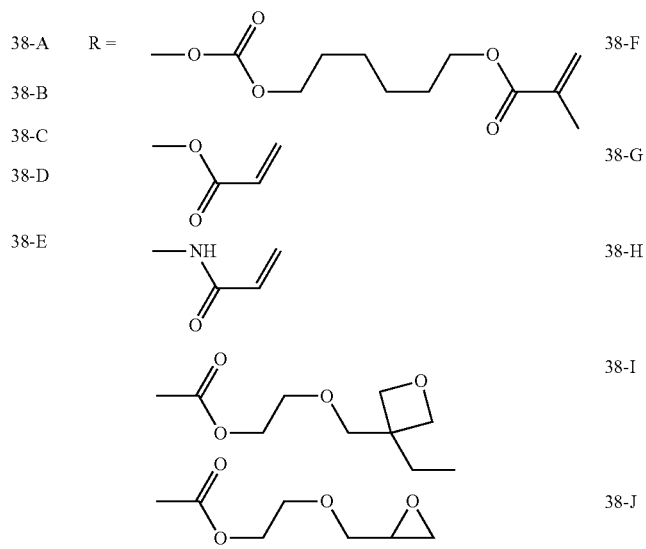
38-E, 38-F, 38-G, 38-H, 38-I, 38-J
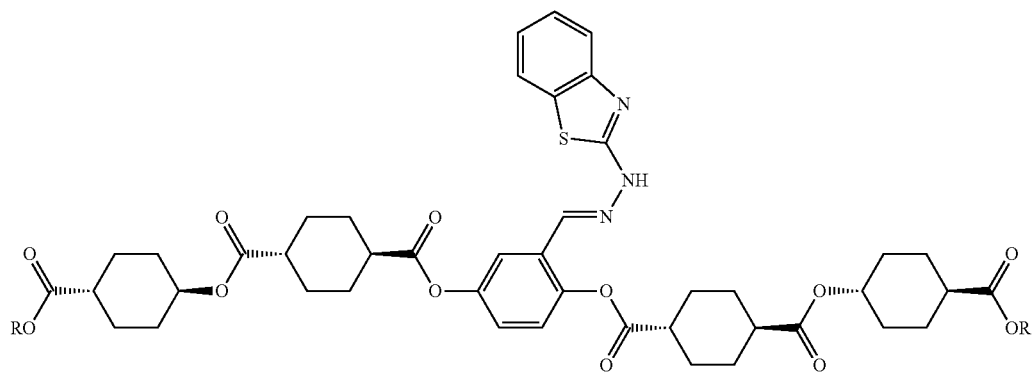
R = —(CH$_2$)$_3$—H  40-A
—(CH$_2$)$_4$—H  40-B
—(CH$_2$)$_6$—H  40-C
—(CH$_2$O)$_2$—H  40-D
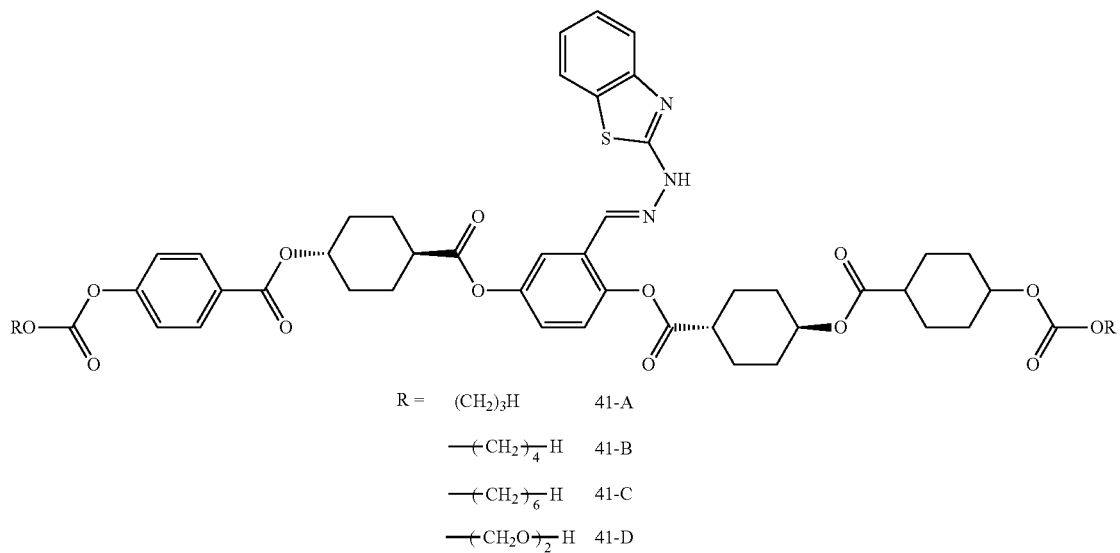
R = (CH$_2$)$_3$H  41-A
—(CH$_2$)$_4$—H  41-B
—(CH$_2$)$_6$—H  41-C
—(CH$_2$O)$_2$—H  41-D 41
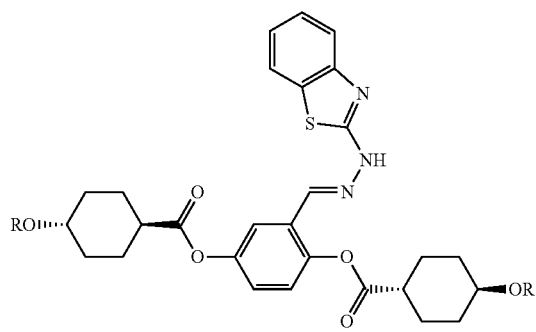
R = —(CH₂)₃—H  42-A
—(CH₂)₄—H  42-B
—(CH₂)₆—H  42-C
—(CH₂O)₂—H  42-D
42
-continued
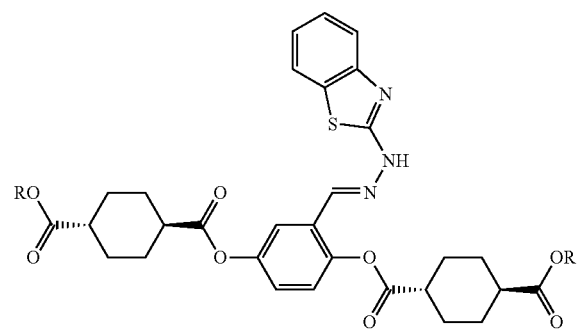
R = —(CH₂)₃—H  43-A
—(CH₂)₄—H  43-B
—(CH₂)₆—H  43-C
—(CH₂O)₂—H  43-D
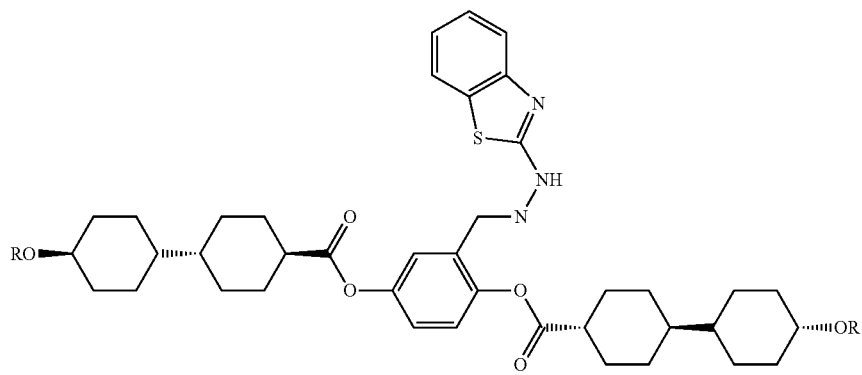
R = —(CH₂)₃—H  44-A
—(CH₂)₄—H  44-B
—(CH₂)₆—H  44-C
—(CH₂O)₂—H  44-D
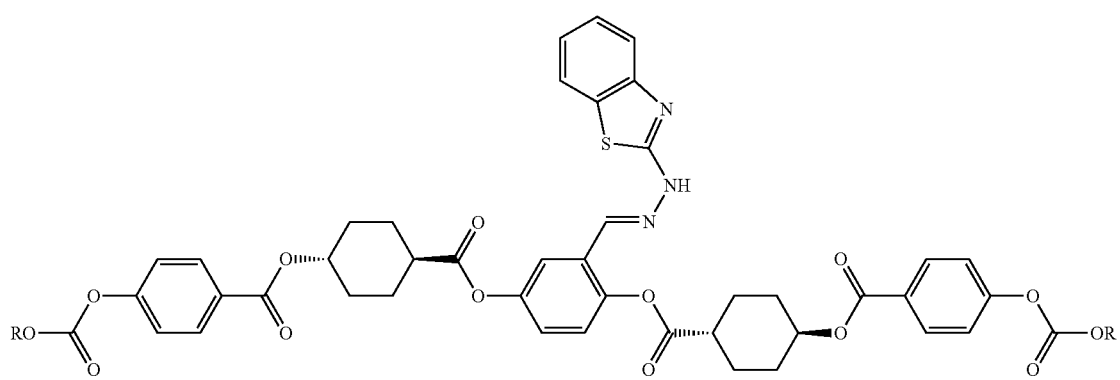

-continued
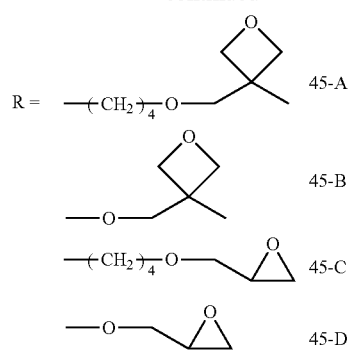
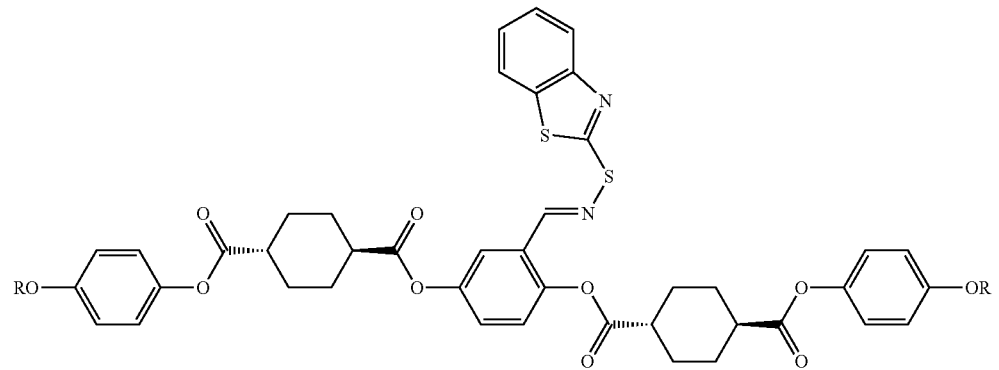
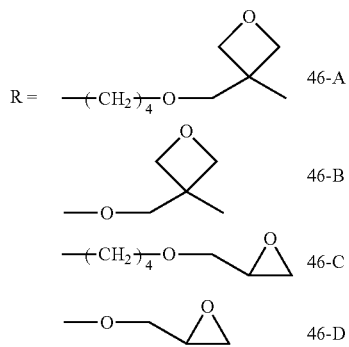
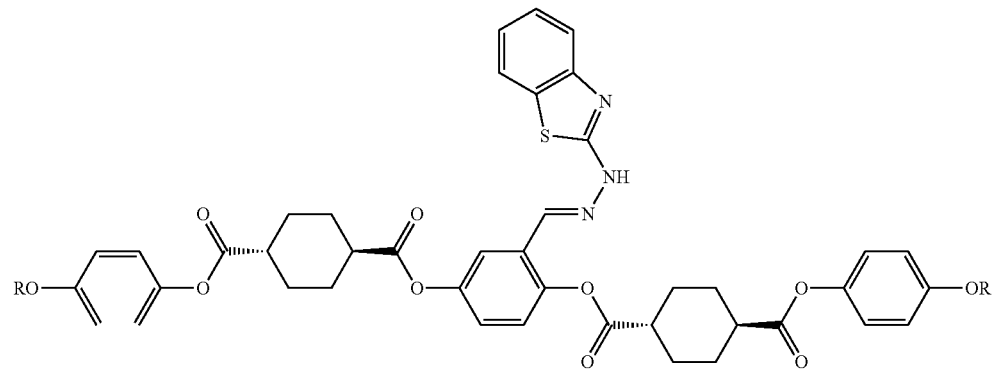

-continued
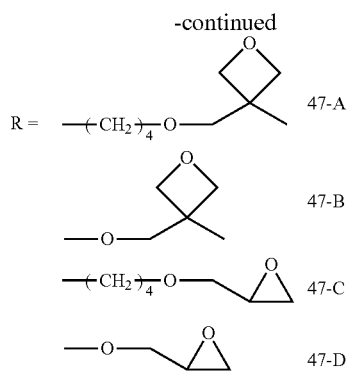
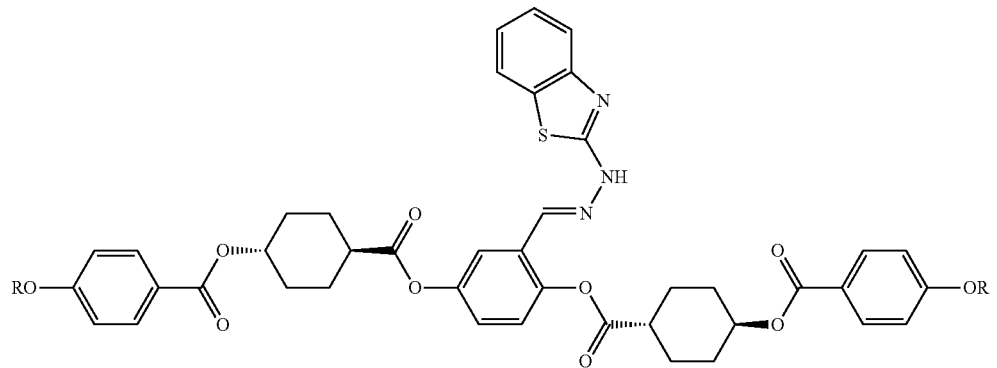
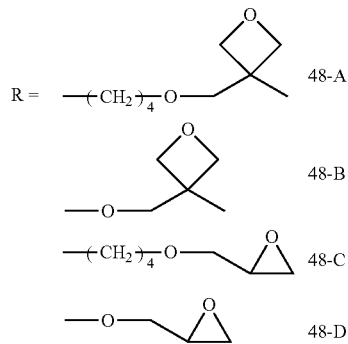
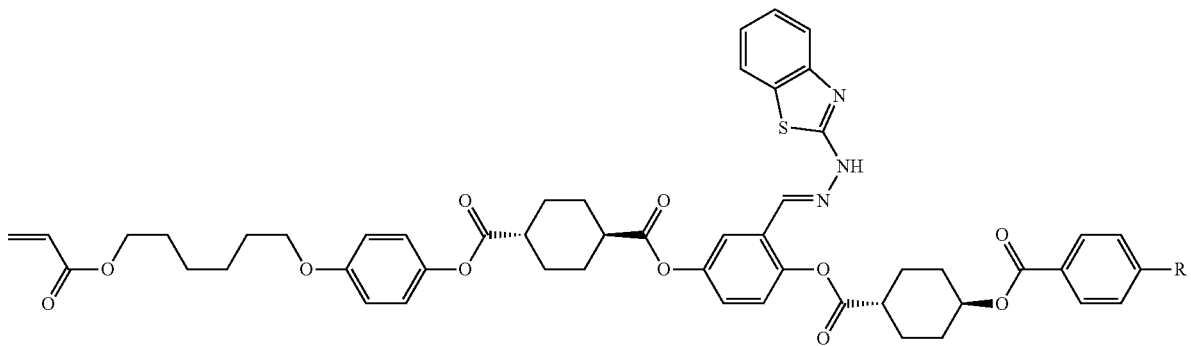

-continued
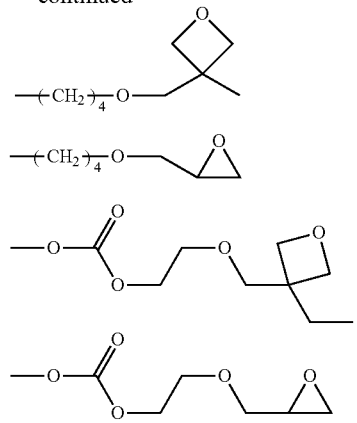
| R = | —O—Me | 49-A | R = | 49-I |
| | —O—Et | 49-B | | |
| | —O—$^n$Pr | 49-C | | |
| | —O—$^n$Bu | 49-D | | 49-J |
| | —Me | 49-E | | |
| | —Et | 49-F | | 49-K |
| | —$^n$Pr | 49-G | | |
| | —$^n$Bu | 49-H | | 49-L |
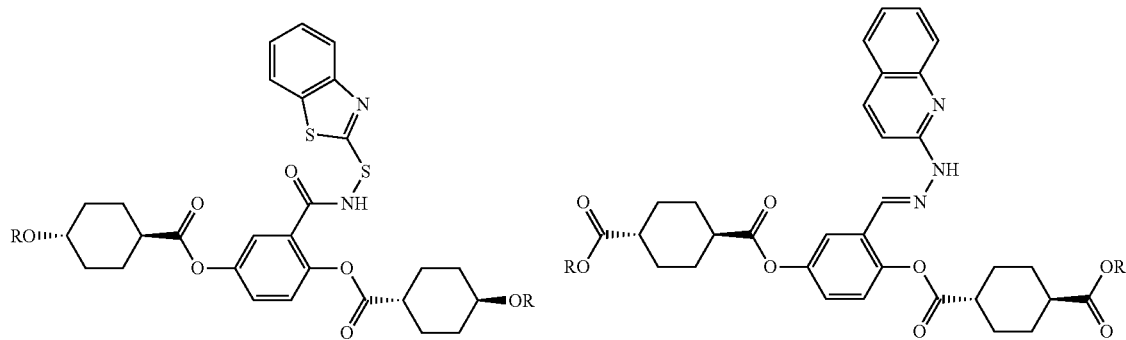
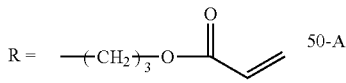
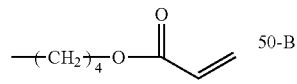
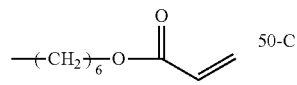
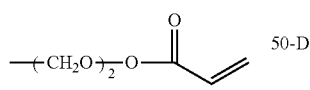
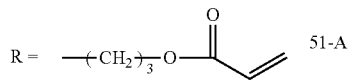
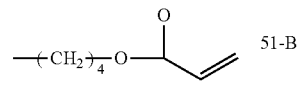
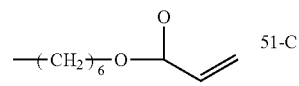
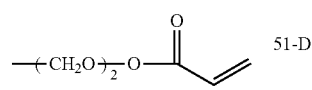
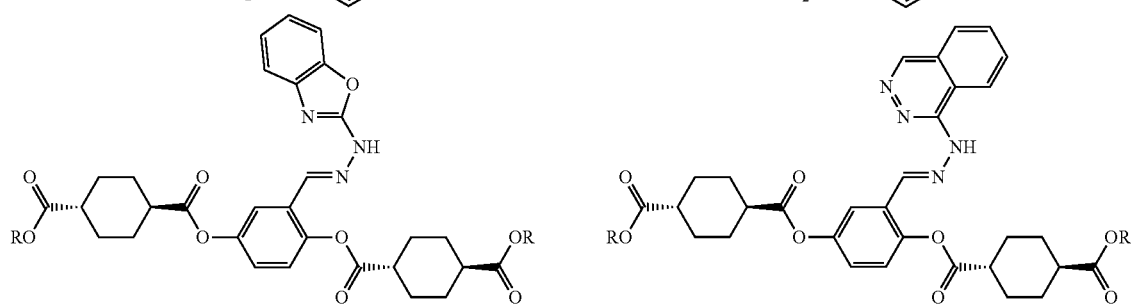

-continued
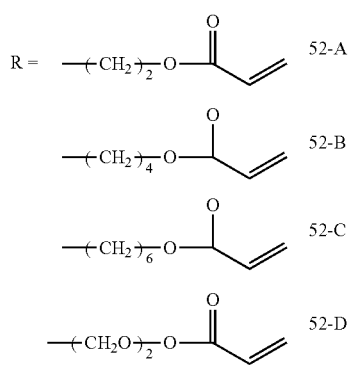
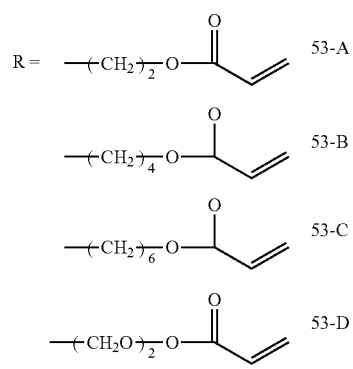
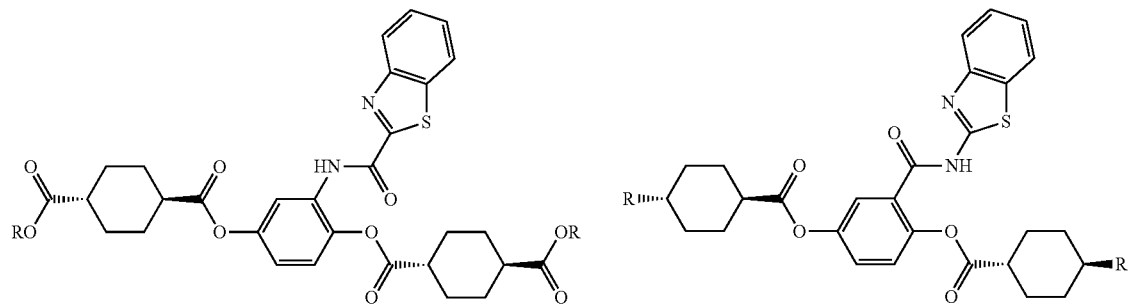
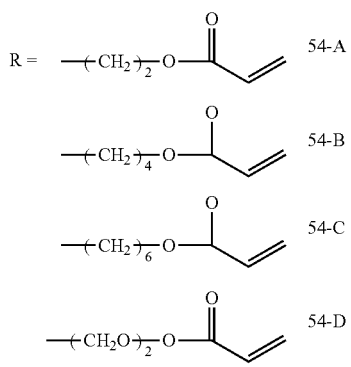
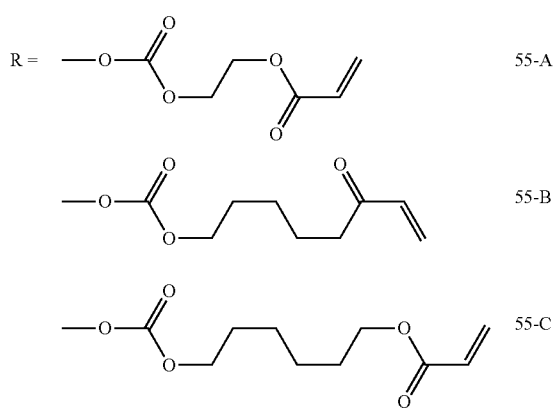
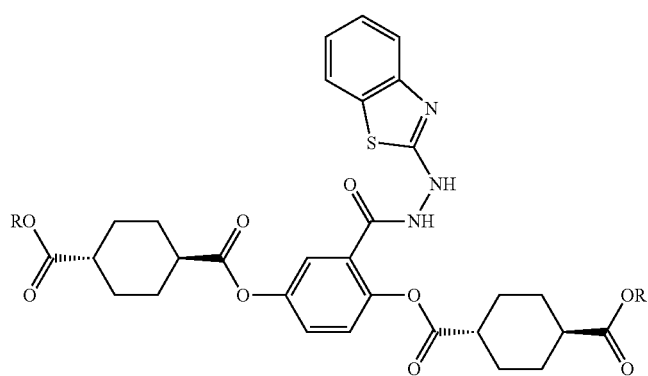

-continued

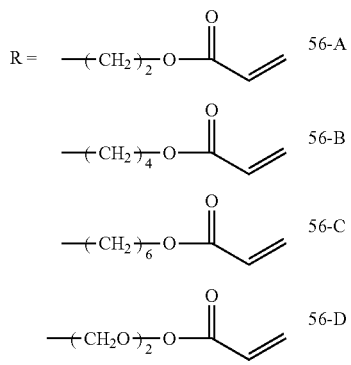

The compound represented by General Formula (1) may be used alone of in combination of two or more. That is, the optically anisotropic layer in the optical film or the polymerizable composition for forming the optically anisotropic layer may contain one or two or more of the compound represented by General Formula (1). In the case where two or more types of the compound represented by General Formula (1) are used for forming the optical film, it is preferable that a compound where $B_1$ and $B_2$ in General Formula (1) each independently represent a divalent cyclic aliphatic group which may have a substituent and a compound where $B_1$ and $B_2$ in General Formula (1) each independently represent a divalent aromatic group which may have a substituent are used in combination.

As the compound where $B_1$ and $B_2$ in General Formula (1) each independently represent a divalent aromatic group which may have a substituent, a compound represented by the following general formula (2) is especially preferable:

General Formula (2)

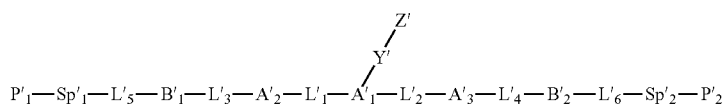

(in General Formula (2), $L'_1$ to $L'_6$ each independently represent a single bond or a linking group, $A'_1$ represents an aromatic group which may have a substituent, $A'_2$ and $A'_3$ each independently represent a cyclic aliphatic group which may have a substituent, $B'_1$ and $B'_2$ each independently represent an aromatic group which may have a substituent, $Sp'_1$ and $Sp'_2$ each independently represent a spacer group, $P'_1$ and $P'_2$ each independently represent a polymerizable group, Y' represents a single bond or a linking group, and Z' represents an aromatic group which may have a substituent).

Specific examples of $L'_1$ to $L'_6$, $A'_1$ to $A'_3$, $B'_1$, $B'_2$, $Sp'_1$, $Sp'_2$, $P'_2$, Y', and Z' in General Formula (2) each include those which is the same as the preferable examples of $L_1$ to $L_6$, $A_1$ to $A_3$, $B_1$, $B_2$, $Sp_1$, $Sp_2$, $P_1$, $P_2$, Y, and Z in General Formula (1).

The method for producing the compound represented by General Formula (1) is more preferably esterification by a mixed acid anhydride process, including an activation step of activating by inducing a carboxylic acid represented by General Formula (A) with a mixed acid anhydride, and a step of reacting the carboxylic acid represented by General Formula (A) (1,4-transcyclohexanedicarboxylic acid or the like) activated by the activation step with a compound represented by General Formula (B) in the presence of a base. It is reported that the esterification in the acid chloride process of a cycloalkanedicarboxylic acid provides a low yield (WO2011/068138A), whereas an esterification according to the aforementioned mixed acid anhydride process can provide a cycloalkanedicarboxylic monoester represented by General Formula (C) in high yield. The compound represented by General Formula (B) used for esterification is preferably a primary alcohol, a secondary alcohol, or phenol, and particularly preferably a primary alcohol.

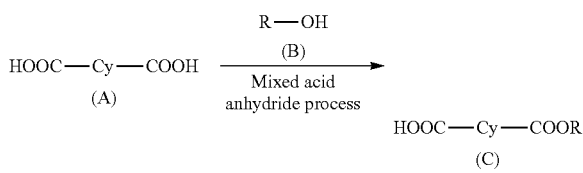

In the general formula, Cy represents an aliphatic cyclic substituent and R represents a substituent.

The activator used in the activation step is not particularly limited, but methanesulfonyl chloride, toluene sulfonyl chloride, or the like can be used as the activator. The base is not particularly limited, but a tertiary amine (for example, triethylamine and diisopropyl ethylamine), an inorganic salt, or the like can be used as the base. The reaction temperature for the activation step varies depending on the kind of the solvent, but is preferably from 0° C. to 30° C.

It is preferable to add the compound represented by General Formula (B) after the activation step, from the viewpoint of preventing the compound represented by General Formula (B) from being adversely affected by the activator. After the activation step, it is preferable to react the carboxylic acid represented by General Formula (A) activated by the activation step or the carboxylic acid represented by General Formula (A) with the compound represented by General Formula (B) in the presence of a base. The reaction temperature at a time of reacting the compound represented by General Formula (B) with the carboxylic acid represented by General Formula (A) activated is not particularly limited, but is preferably from 0° C. to 30° C., and more preferably from 10° C. to 25° C.

<<Optically Anisotropic Layer Containing Compound Represented by General Formula (1)>>

In one embodiment of the present invention, particularly, in the case where the compound represented by General Formula (1) does not contain a polymerizable group, the compound represented by General Formula (1) is one component of the polymer composition, and thereafter, an optically anisotropic layer may be formed from the polymer composition.

The material for the polymer composition is not particularly limited, and examples thereof include polymers or celluloses including, for example, esters, carbonates, olefins, acetylene, cycloolefins, and norbornene, and these may be used as a mixture of a plurality of the materials.

The polymer composition preferably contains a cellulose as a main component.

Here, the phrase "contains as a main component" means that the content of the cellulose in the entire polymer composition is preferably 50% by mass or more, and more preferably 75% by mass.

In the case of the polymer composition containing the cellulose as a main component, the content of the compound represented by General Formula (1) is preferably from 0.1 parts by mass to 50 parts by mass, more preferably from 0.1 parts by mass to 30 parts by mass, still more preferably from 0.5 parts by mass to 30 parts by mass, and most preferably from 1 part by mass to 30 parts by mass, with respect to 100 parts by mass of cellulose.

The cellulose is preferably cellulose acylate.

Hereinafter, cellulose acylate will be described.

[Cellulose Acylate]

<Cotton as Raw Material of Cellulose Acylate>

Examples of the cotton as a raw material of cellulose acylate (also referred to as a cellulose as a raw material) include cotton linters and wood pulp (broadleaf tree pulp, and conifer tree pulp). Any cellulose acylate obtained from any cellulose as a raw material may be used, and a plurality of celluloses may be used as a mixture of two or more thereof as necessary. There are detailed descriptions of these celluloses as a raw material in, for example, "Plastic Material Lectures (17) Cellulose-Based Resin" (Marusawa and Uda, The Nikkan Kogyo Shimbun, Ltd., published in 1970); and Kokai Giho (Open Technical Report) 2001-1745 (pp. 7 to 8) by Japan Institute of Invention & Innovation, and the celluloses described in these publications may be used.

The aforementioned specific cellulose acylate is preferably cellulose acylate which is a mixed fatty acid ester of a cellulose obtained by substituting a hydroxyl group of the cellulose with an acetyl group and a cellulose obtained by substituting a hydroxyl group with an acyl group having 3 or more carbon atoms, in which the degree of substitution on a hydroxyl group of the cellulose satisfies the following expressions (5) and (6).

$$2.0 \leq A+B \leq 3.0 \quad \text{Expression (5)}$$

$$0 < B \quad \text{Expression (6):}$$

In the equations, A represents the degree of substitution of an acetyl group substituting for a hydroxyl group of the cellulose, and B represents the degree of substitution of an acyl group having 3 or more carbon atoms substituting for a hydroxyl group of the cellulose.

The glucose units which constitute cellulose by bonding through a β-1,4-glycoside bond have free hydroxyl groups at the 2-, 3-, and 6-positions thereof. A cellulose acylate is a polymer obtained by esterifying a part or the whole of these hydroxyl groups with an acyl group(s). The substitution degree of acyl means the ratio of esterification at the 2-, 3-, or 6-position in the cellulose (an esterification of 100% corresponds to a substitution degree of 1).

<Degree of Polymerization of Cellulose Acylate>

The polymerization degree of cellulose acylate is preferably from 180 to 700 in terms of viscosity average polymerization degree. In the case of cellulose acetate, the polymerization degree is more preferably from 180 to 550, still more preferably from 180 to 400, and particularly preferably from 180 to 350, in terms of viscosity average polymerization degree. By adjusting the polymerization degree to 700 or less, the viscosity of a dope solution of cellulose acylate does not become excessively high and the production of a film by casting then tends to be facilitated. In addition, adjusting the polymerization degree to 180 or more is preferable because the strength of a film formed can be further increased. The average polymerization degree can be measured by a limiting viscosity method by Uda et al., (Kazuo Uda and Hideo Saito, "The Journal of the Society of Fiber Science and Technology, Japan", Vol. 18, No. 1, pp. 105 to 120, 1962). Specifically, it can be measured according to the method described in JP1997-95538A (JP-H09-95538A).

In addition, the distribution of molecular weight of cellulose acylate is evaluated by gel permeation chromatography, and further, a smaller polydispersity index Mw/Mn (in which Mw means a mass average molecular weight and Mn means a number average molecular weight) and a narrower molecular weight distribution are preferable. The specific Mw/Mn value is preferably from 1.0 to 3.0, more preferably from 1.0 to 2.0, and still more preferably from 1.0 to 1.6.

If a low molecular weight component is removed, the average molecular weight (polymerization degree) thereof becomes higher, but the viscosity thereof becomes lower than that of ordinary cellulose acylate, which means that the removal is useful. A cellulose acylate containing a small amount of a low molecular weight component can be obtained by removing the low molecular weight component(s) from a cellulose acylate synthesized in a usual manner. The removal of the low molecular weight component can be carried out by washing the cellulose acylate with an appropriate organic solvent. When the cellulose acylate containing a small amount of the low molecular weight component is to be produced, the amount of a sulfuric acid catalyst in the acetylation reaction is preferably adjusted to 0.5 parts by mass to 25 parts by mass with respect to 100 parts by mass of the cellulose. When the amount of the sulfuric acid catalyst is set within the range, a cellulose acylate having a preferable molecular weight distribution (uniform molecular weight distribution) can be synthesized. In the case that the cellulose acylate is used when the cellulose acylate film is produced, the percentage of water content in the cellulose acylate is preferably 2% by mass or less, more preferably 1% by mass or less, and still more preferably 0.7% by mass or less. It is known that ordinary cellulose acylate contains water in an amount of 2.5% by mass to 5% by mass. Thus, in order to set the percentage of water content in the cellulose acylate within the range, it is preferable to dry ordinary cellulose acylate. The method for the drying is not particularly limited as long as the target percentage of water content can be attained.

As the cotton as a raw material and the synthesis method for the cellulose acylate, those described in, for example, Kokai Giho (Open Technical Report) (Kogi No. 2001-1745, pp. 7 to 12, published on Mar. 15, 2001, and Japan Institute of Invention & Innovation) by Japan Institute of Invention & Innovation can be employed.

<Additive to Cellulose Acylate>

To a cellulose acylate solution, in addition to the compound represented by General Formula (1), any of various additives (for example, an ultraviolet absorber, a plasticizer, a deterioration preventing agent, fine particles, and an optical-characteristic controlling agent) may be added. Further, for the timing at which the compound represented by General Formula (1) and the other additives are added, they may be added in any of the dope production steps. They may be added in the last step of the dope preparation steps.

<Organic Solvent of Cellulose Acylate Solution>

In the case of preparing an optically anisotropic layer from a polymer composition, in particular, in the case of preparing an optically anisotropic layer from a composition containing cellulose acylate, a cellulose acylate film is preferably made by an solvent cast method, and more preferably prepared using a solution (dope) prepared by dissolving cellulose acylate in an organic solvent. An organic solvent that is preferably used is preferably a solvent selected from esters, ketones, or ethers having 3 to 12 carbon atoms, or halogenated hydrocarbons having 1 to 7 carbon atoms. The esters, the ketones, and the ethers may have cyclic structures. A compound having two or more out of the functional groups (that is. —O—, —CO—, and —COO—) of the esters, ketones, and the ethers can also be used as a main solvent. For example, the compound may also have other functional groups such as an alcoholic hydroxyl group. In the case of the main solvent having two or more kinds of the functional groups, the number of carbon atoms may be within a range regulated for the compound having a certain functional group.

Furthermore, a chlorine-based halogenated hydrocarbon may be used as a main solvent, and a non-chlorine-based solvent may also be used as a main solvent as disclosed, for example, in Kokai Giho (Open Technical Report) (Kogi No. 2001-1745, pp. 12 to 16, published in 2001, and Japan Institute of Invention & Innovation).

[Optical Film]

Next, a method for producing a film using the cellulose acylate solution will be described. As the method and equipment for producing the cellulose acylate film, the solution casting film-producing method and the solution casting film producing apparatus that are used in the production of the conventional cellulose triacetate film may be widely employed.

<Process for Producing Cellulose Acylate Film>

(Dissolution Step)

With regard to the preparation of the cellulose acylate solution (dope), there is no particular limitation to a method used to dissolve cellulose acylate. The dissolution may be carried out at the room temperature, or alternatively the dissolution may be carried out by a cooling dissolution method, a high-temperature dissolution method, or a combination of these methods. As to the production of the cellulose acylate solution, and each of the steps of concentration and filtration of the solution, which are associated with the dissolution step, the production steps described in detail in Kokai Giho (Open Technical Report) (Kogi No. 2001-1745, pp. 22 to 25, published on Mar. 15, 2001, and Japan Institute of Invention & Innovation) by Japan Institute of Invention & Innovation are preferably used.

The dope transparency of the cellulose acylate solution is preferably 85% or more, more preferably 88% or more, and still more preferably 90% or more. As to a specific method to calculate the dope transparency, the dope solution is injected into a glass cell which is 1 cm by 1 cm square, to measure the absorbance of the solution at a wavelength of 550 nm by using a spectrophotometer (UV-3150, trade name, manufactured by Shimadzu Corporation). The absorbance of the solvent may be measured as a control in advance, to calculate the transparency of the cellulose acylate solution from the ratio of the absorbance of the solution to that of the control.

(Casting, Drying, and Winding Steps)

A dope (cellulose acylate solution) prepared in a dissolution machine (pot) is temporarily stored in a storage pot, and after defoaming to remove the foams contained in the dope, the dope is subjected to the final preparation. The dope is discharged from a dope outlet and fed into a pressure die via, for example, a pressure constant-rate gear pump whereby the dope can be fed at a constant flow rate at a high accuracy depending on a rotational speed. From a pipe sleeve (slit) of the pressure die, the dope is uniformly cast onto a metallic support continuously running in the casting section. At the peeling point where the metallic support has almost rounded in one cycle, the half-dried dope film (also referred to as a web) is peeled from the metallic support. The obtained web is clipped at both ends and dried by transporting with a tenter while maintaining the width at a constant level. Subsequently, the thus-obtained web film is mechanically transported with rolls in a dryer, to complete the drying, followed by winding with a winder into a rolled shape in a given length. Combination of the tenter and rolls in the dryer may vary depending on the purpose. For example, in the solvent cast film-forming method in use for a functional protective film that is an optical member for electronic displays or a silver halide photographic sensitive material, a coating device is additionally employed in many cases, in addition to the solvent cast film-forming apparatus, so as to treat the film surface, for example, by providing an undercoat layer, an antistatic layer, an antihalation layer, a protective layer, or the like. These steps are described in detail in Kokai Giho (Open Technical Report) (Kogi No. 2001-1745, pp. 25 to 30, published on Mar. 15, 2001, and Japan Institute of Invention and Innovation) by Japan Institute of Invention & Innovation.

(Stretching Treatment)

The cellulose acylate film is preferably subjected to a stretching treatment to adjust the retardation value. In particular, when the in-plane retardation value of a cellulose acylate film is to be made a high value, a method of positively stretching the film in the width direction, for example, a method of stretching the produced film, as described, for example, in JP1987-115035A (JP-S62-115035A), JP1992-152125A (JP-H04-152125A), JP1992-284211A (JP-H04-284211A), JP1992-298310A (JP-H04-298310A), and JP1999-48271A (JP-H11-48271A) may be used.

Stretching of the film is carried out under the condition of the ordinary temperature or heating. The heating temperature is preferably no higher than the glass transition temperature of the film. The stretching of the film may be carried out by uniaxial stretching only in the longitudinal or transverse direction, or biaxial stretching in a simultaneous or successive manner. The film is stretched at a rate of preferably 1% to 200%, more preferably 1% to 100%, and still more preferably 1% to 50%.

For example, in the case where the optical film of the present invention is used in a polarizing plate, in order to suppress light leakage when a polarizing plate is viewed from a slant direction, it is necessary to dispose the transmission axis of a polarizing film in parallel to the in-plane slow axis (retardation axis) of the cellulose acylate film. Generally, the transmission axis of a roll film-shaped polarizing film, which is continuously produced, is parallel to the width direction of the roll film. Thus, in order to apply the roll film-shaped polarizing film continuously to a protective film composed of the roll film shaped cellulose acylate film to make lamination of them, it is preferable that the in-plane slow axis of the roll film-shaped protective film is parallel to the width direction of the film. Thus, it is preferable to further stretch the cellulose acylate film in the width direction. Further, the stretching treatment may be carried out in the course of the film-forming step, or raw film formed and wound may be stretched. In the former case, the film may be stretched in the condition that the film contains a residual solvent. The film can be preferably stretched at an amount of the residual solvent of 2% by mass to 30% by mass.

The thickness of the cellulose acylate film which is obtained after drying varies depending on the purpose of use, but is preferably in the range of 1 μm to 500 μm, more preferably 5 μm to 300 μm, and still more preferably 5 μm to 150 μm. Further, when the film is for use in an optical device, in particular, in a VA liquid crystal display apparatus, the thickness is preferably from 8 μm to 110 μm. In order to have a desired thickness of the film, the adjustment of the film thickness was carried out by adjusting, for example, concentration of the solid contents contained in the dope, the slit gap of a pipe sleeve of a die, the extrusion pressure from the die, the speed of the metallic support, and the like to attain a desired thickness.

The width of the cellulose acylate film thus obtained is preferably from 0.5 m to 3 m, more preferably from 0.6 m to 2.5 m, and still more preferably from 0.8 m to 2.2 m. The winding length per roll is preferably from 100 m to 10000 m, more preferably from 500 m to 7000 m, and still more preferably from 1000 m to 6000 m. During winding, at least one edge of the film is preferably knurled, and the knurling width is preferably from 3 mm to 50 mm, and more preferably from 5 mm to 30 mm, and the knurling height is preferably from 0.5 to 500 μm, and more preferably from 1 μm to 200 μm. The film may be knurled only on one side or on both sides.

The difference in the Re(550) values of the film in the width direction is preferably ±5 nm, and more preferably ±3 nm. Further, the variation in the Rth(550) values of the film in the width direction is preferably ±10 nm, and more preferably ±5 nm. Further, the variations of the Re value and the Rth values in the length direction are also preferably within the ranges of the variation in the width direction.

<Optically Anisotropic Layer Formed by Curing of Polymerizable Composition Containing Compound Represented by General Formula (1)>>

In one aspect of the present invention, particularly, in the case where the compound represented by General Formula (1) contains a polymerizable group or in the case of using other polymerizable compounds, in addition to the compound represented by General Formula (1), the polymerizable compound (for example, a compound represented by the following general formula (1), or the like) can be used as one component of the polymerizable composition. By curing such a polymerizable composition containing the compound represented by General Formula (1), an optically anisotropic layer may be formed.

[Polymerizable Composition]
[Liquid Crystal Compound Other Than Compound Represented by General Formula (1)]

The polymerizable composition for forming an optically anisotropic layer may contain other liquid crystal compounds, in addition to the compound represented by General Formula (1).

For example, it is also preferable that the composition contains a compound having a structure represented by the following general formula (I).

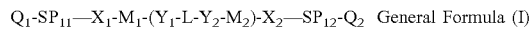
$Q_1\text{-}SP_{11}\text{—}X_1\text{-}M_1\text{-}(Y_1\text{-}L\text{-}Y_2\text{-}M_2)\text{-}X_2\text{—}SP_{12}\text{-}Q_2$  General Formula (I)

In the formula, r is an integer of 0 or more, which represents the repetition number of $(Y_1\text{-}L\text{-}Y_2\text{-}M_2)$'s, $Q_1$ and $Q_2$ are each a polymerizable group, $SP_{11}$ and $SP_{12}$ represent a spacer group, $X_1$ and $X_2$ are each a single bond or an oxygen atom, —$Y_1$-L-$Y_2$— represents a linear alkylene group, or an alkylene group containing at least one —O— or —C(=O)—, $M_1$ is a group represented by —$Ar_1$—COO—$Ar_2$—COO—$Ar_3$—COO—, —$Ar_1$—COO—$Ar_2$—COO—$Ar_3$—, or —$Ar_1$—COO—$Ar_2$—$Ar_3$—, $M_2$ is a group represented by —$Ar_3$—OCO—$Ar_2$—OCO—$Ar_1$—OCO—, —$Ar_3$—OCO—$Ar_2$—OCO—$Ar_1$—, or —$Ar_3$—OCO—$Ar_2$—$Ar_1$—, and $Ar_1$, $Ar_2$, and $Ar_3$ each independently represent a cyclic group.

$Q_1$ and $Q_2$ each independently represent a polymerizable group, and have the same definition as the polymerizable group each represented by $P_1$ and $P_2$ in General Formula (1) and the preferred range thereof is also the same.

$SP_{11}$ and $SP_{12}$ each represent a spacer group, and have the same definition as the spacer group each represented by $Sp_1$ and $Sp_2$ in General Formula (1).

The spacer group represented by each of $SP_{11}$ and $SP_{12}$ is preferably an alkylene group having 2 to 12 carbon atoms or an alkylene oxide having 2 to 12 carbon atoms, and more preferably an alkylene oxide having 2 to 12 carbon atoms.

The alkylene oxide is preferably ethyleneoxide. A case of a structure having 2 to 3 units as a repeating unit, that is, —$(CH_2)_n$—O— (in which n represents an integer of 2 to 6) is particularly preferable since it can allow control over a wide temperature band in the liquid crystal phase.

In addition, the number of carbon atoms contained in the spacer group each represented by $SP_{11}$ and $SP_{12}$ is preferably an integer of 2 to 8.

r represents an integer of 0 or more, but is preferably from 0 to 3, more preferably from 0 to 2, and particularly preferably from 0 to 1.

$Ar_1$, $Ar_2$, and $Ar_3$ each independently preferably represent a phenylene group or biphenylene group substituted with an arbitrary number of bromine atoms, methyl groups, or methoxy groups. The total number of benzene rings contained in $Ar_1$, $Ar_2$, and $Ar_3$ is preferably from 3 to 6, more preferably from 3 to 5, and particularly preferably from 3 to 4.

The compound of the present invention, represented by General Formula (I), can be synthesized by a combination of known synthesis reactions. That is, the compound can be synthesized with reference to the methods described in various literatures (for example, Methoden derOrganischen Chemie (edited by Houben-Weyl), Some Specific Methods (published by Thieme-Verlag, written by Stuttgart), Experiments Chemical Course and New Experiments Chemical Course). In addition, the descriptions of the respective specifications of U.S. Pat. No. 4,683,327A, U.S. Pat. No. 4,983,479A, U.S. Pat. No. 5,622,648A, U.S. Pat. No. 5,770,107A, WO95/22586A, WO97/00600A, WO98/47979A, and GB2297549A may be also referred for the synthesis method.

As another liquid crystal compound, a liquid crystal compound represented by the following general formula (101) is also preferable. The liquid crystal compound represented by General Formula (101) has a structure with asymmetric groups bonded to a central ring structure constituting a mesogenic group, and thus, the crystallinity is decreased. Therefore, by using the liquid crystal compound in combination with the compound represented by General Formula (1), the effect of suppressing crystal precipitation properties of the liquid crystal compounds tends to increase.

$CH_2$ or two or more non-adjacent $CH_2$'s in the aliphatic group may be substituted with —O—, —S—, —OCO—, —COO—, or —OCOO—.

[Tilt Angle Controlling Agent]

The polymerizable composition may contain a tilt angle controlling agent. With the addition of a tilt angle controlling agent, a polar angle from the support of the liquid crystal compound or from an air interface (during production) can be controlled.

As the tilt angle controlling agent, for example, a copolymer of a monomer containing a fluoroaliphatic group can be used, and among these, a copolymer with an aromatic condensed ring functional group or with a monomer containing a carboxyl group, a sulfo group, a phosphonoxy group, or a salt thereof is preferably used. Further, the use of a plurality of tilt angle controlling agents enables fine and stable control of the tilt angle. For such tilt angle controlling

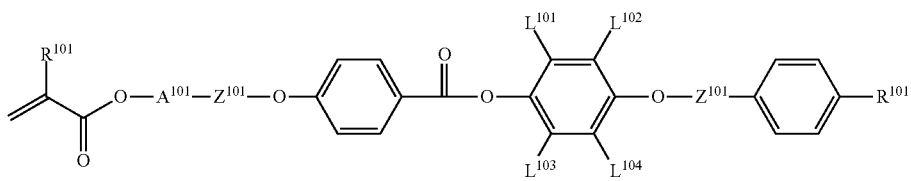

General Formula (101)

In General Formula (101), $A^{101}$ represents a methylene group having 2 to 18 carbon atoms, and one $CH_2$ or two or more non-adjacent $CH_2$'s in the methylene group may be substituted with —O—, $Z^{101}$ represents —CO—, —O—CO—, or a single bond, $Z^{102}$ represents —CO— or —CO—CH=CH—, $R^{101}$ represents a hydrogen atom or a methyl group, $R^{102}$ represents a hydrogen atom, a halogen atom, a linear alkyl group having 1 to 4 carbon atoms, methoxy group, ethoxy group, an aromatic ring which may have a substituent, a cyclohexyl group, a vinyl group, a formyl group, a nitro group, a cyano group, an acetyl group, an acetoxy group, an N-acetylamide group, an acryloylamino group, an N,N-dimethylamino group, a maleimide group, a methacryloylamino group, an allyloxy group, an allyloxycarbamoyl group, an N-alkyloxycarbamoyl group with an alkyl group having 1 to 4 carbon atoms, an N-(2-methacryloyloxyethyl)carbamoyloxy group, an N-(2-acryloyloxyethyl)carbamoyloxy group, or a structure represented by the following formula (1-2), and $L^{101}$, $L^{102}$, $L^{103}$, and $L^{104}$ each independently represent an alkyl group having 1 to 4 carbon atoms, an alkoxy group having 1 to 4 carbon atoms, an alkoxycarbonyl group having 2 to 5 carbon atoms, an acyl group having 2 to 4 carbon atoms, a halogen atom, or a hydrogen atom, and at least one of $L^{101}$, $L^{102}$, $L^{103}$, and $L^{104}$ represents a group other than a hydrogen atom.

—$Z^{105}$-T-Sp-P   Formula (1-2)

In Formula (1-2),

P represents an acryl group, a methacryl group, or a hydrogen atom, $Z^{105}$ represents a single bond, —COO—, —CONR$^1$—, or —COS—, and R$^1$ represents a hydrogen atom or a methyl group, T represents 1,4-phenylene, and Sp represents a divalent aliphatic group having 1 to 12 carbon atoms, which may have a substituent, and one agents, the descriptions in the paragraphs 0022 to 0063 of JP2008-257205A and paragraphs 0017 to 0124 of JP2006-91732A can be referred to.

Further, examples of a means of controlling the inclination angle of the liquid crystal compound, in addition to a means of using a tilt angle controlling agent in the polymerizable composition, include a method of imparting a pre-inclination angle by an alignment film with controlled rubbing conditions. An alignment film that provides a pre-inclination angle can be used in combination with the tilt controlling agent.

[Polymerization Initiator]

The polymerizable composition may contain a polymerization initiator. The polymerization initiator is preferably incorporated in the case where the liquid crystal compound has a polymerizable group or in the case where the liquid crystal compound has a polymerizable compound. Specific examples of the polymerization initiator include α-carbonyl compounds (described in the respective specifications of U.S. Pat. No. 2,367,661 A and U.S. Pat. No. 2,367,670A), acyloin ethers (described in the specification of U.S. Pat. No. 2,448,828A), α-hydrocarbon-substituted aromatic acyloin compounds (described in the specification of U.S. Pat. No. 2,722,512A), polynuclear quinone compounds (described in the respective specifications of U.S. Pat. No. 3,046,127A and U.S. Pat. No. 2,951,758A), combinations of triaryl imidazole dimer and p-aminophenyl ketone (described in the specification of U.S. Pat. No. 3,549,367A), acridine and phenazine compounds (described in the specifications of JP1985-105667A (JP-S60-105667A), and U.S. Pat. No. 4,239,850A), oxadiazole compounds (described in the specification of U.S. Pat. No. 4,212,970A), and acylphosphine oxide compounds (described in JP1988-40799B (JP-S63-40799B), JP1993-29234B (JP-H05-29234B), JP1998-95788A (JP-H10-95788A), and JP1998-29997A (JP-H10-29997A).

Specific examples of the photopolymerization initiator as a polymerization initiator include Irgacure series (for example, Irgacure 651, Irgacure 754, Irgacure 184, Irgacure 2959, Irgacure 907, Irgacure 369, Irgacure 379, and Irgacure 819) and Darocure Series (for example, Darocure TPO and Darocure 1173) commercially available from BASF Japan, Ltd., Quantacure PDO, and Ezacure Series (for example, Ezacure TZM, Ezacure TZT, and Ezacure KTO46) commercially available from Lamberti.

The amount of the photopolymerization initiator to be used is preferably from 0.01% by mass to 20% by mass and more preferably from 0.5% by mass to 5% by mass of the polymerizable liquid crystal compound.

[Non-Liquid Crystal Polymerizable Compound]

The polymerizable composition may contain a non-liquid crystal polymerizable compound.

The non-liquid crystal polymerizable compound that is used in combination with a liquid crystal compound is not particularly limited as long as it has compatibility with the liquid crystal compound and does not remarkably cause a change in the inclination angles and inhibition of the alignment of the liquid crystal compound. Among these, a compound having an ethylenically unsaturated group which is polymerizable active, such as a vinyl group, a vinyloxy group, an acryloyl group, and a methacryloyl group, is preferably used.

As the non-liquid crystal polymerizable compound, a polymerizable compound having two or more polymerizable active groups (reactive functional groups) is particularly preferably used, which is expected to promote adhesion between an alignment film and an optically anisotropic layer. The non-liquid crystal polymerizable compound may be a polymer, but is preferably a monomer (for example, a monomer having a weight average molecular weight of 2000 or less).

Specific examples of the non-liquid crystal polymerizable compound include esters of polyhydric alcohol and (meth) acrylic acid (for example, ethylene glycol di(meth)acrylate, 1,4-cyclohexane diacrylate, pentaerythritol tetra(meth)acrylate, pentaerythritol tri(meth)acrylate, trimethylol propane tri(meth)acrylate, trimethylolethane tri(meth)acrylate, dipentaerythritol tetra(meth)acrylate, dipentaerythritol penta (meth)acrylate, dipentaerythritol hexa(meth)acrylate, 1,2,3-cyclohexane tetramethacrylate, polyurethane polyacrylate, and polyester polyacrylate), vinylbenzene and derivatives thereof (for example, 1,4-divinylbenzene, 4-vinylbenzoic acid-2-acryloylethyl ester, and 1,4-divinylcyclohexanone), vinyl sulfone (for example, divinyl sulfone), acrylamide (for example, methylene-bisacrylamide), and methacrylamide.

One kind or two or more kinds of the non-liquid crystal polymerizable compound may be contained in a polymerizable composition. The content of the non-liquid crystal polymerizable compound is generally in the range of 0.5% by mass to 50% by mass, and preferably in the range of 1% by mass to 30% by mass, with respect to the liquid crystal compound.

[Other Additives]

The polymerizable composition may contain the crosslinkable polymer described in the paragraphs <0052> to <0082> of JP2004-238431A, in addition to those above. Further, the polymerizable composition may also contain a surfactant for controlling surface properties or surface shapes, an additive (plasticizer) for reducing an alignment temperature, a polymerizable monomer, an agent for imparting other functions, or the like.

[Solvent]

The polymerizable composition may contain a solvent. As the solvent of the composition, an organic solvent is preferably used. Examples of the organic solvent include amides (for example, N,N-dimethyl formamide), sulfoxides (for example, dimethyl sulfoxide), heterocyclic compounds (for example, pyridine), hydrocarbons (for example, benzene and hexane), alkyl halides (for example, chloroform and dichloromethane), esters (for example, methyl acetate and butyl acetate), ketones (for example, acetone, methyl ethyl ketone, and cyclohexanone), and ethers (for example, tetrahydrofuran and 1,2-dimethoxy ethane), with alkyl halides and ketones being preferable. As the solvent, one kind or a combination of two or more kinds of organic solvents may be used. The solvent is preferably prepared such that the solid concentration of the composition is 10% by mass to 50% by mass.

[Method for Producing Optically Anisotropic Layer by Curing Polymerizable Composition]

The optically anisotropic layer can be produced by applying the above-mentioned polymerizable composition on the surface of a support or on the surface of an alignment film formed on the support to cure the polymerizable composition. In addition, the optically anisotropic layer can also be produced by subjecting the surface of a polarizing film (for example, a polyvinyl alcohol film) to a rubbing treatment and applying a polymerizable composition to the surface to cure the polymerizable composition.

[Support]

The optical film of the present invention may contain a support. The support is preferably contained, in particular in the case where an optically anisotropic layer is formed by the curing of a polymerizable compound. The support has a function as a substrate for applying the above-mentioned polymerizable composition or a function for maintaining the layer shape of the optically anisotropic layer. The support may be a temporary support which is used as a substrate for applying the above-mentioned polymerizable composition after formation of the optically anisotropic layer and then peeled of That is, the optical film of the present invention may not contain a support, and for example, only the alignment film may also have a function as the support. In the case where the support peeled off after forming the optically anisotropic layer is used, a material having a texture with easily peelable surface properties, and glass, a polyester film that has not been subjected to easy-adhesion treatment, or the like can be used as such a temporary support for the formation.

As the support (temporary support), in addition to the plastic films, glass or the like can also be used. Examples of the plastic films include polyesters such as polyethylene terephthalate (PET), polycarbonates, acrylic resins, epoxy resins, polyurethanes, polyamides, polyolefins, cellulose, and silicone.

Moreover, if the alignment film also has a function as a support, the support can further include a material as described below.

The film thickness of the support may be any one from about 5 μm to 1000 μm, preferably from 10 μm to 250 μm, and more preferably from 15 μm to 90 μm.

It is also possible to prepare the support directly on a glass substrate such as a polarizing plate and a liquid crystal cell in the form of a thin film, in which an optically anisotropic layer is directly formed by rubbing a polarizer while not laminating on the polymer film.

[Alignment Treatment and Alignment Film]

In forming the optically anisotropic layer, a technique is necessary for aligning the molecules of the liquid crystal compound in the composition in a desired alignment state. For example, it is common to use a technique of using an alignment film for aligning liquid crystal compound in a desired direction. Examples of the alignment film includes a rubbing-treated film including an organic compound such as a polymer; an oblique deposition film of an inorganic compound; a microgrooved film; and a film (mono-molecular laminated film) formed by lamination of LB layers formed according to a Langmuir-Blodgett's method of depositing an organic compound such as ω-tricosanoic acid, dioctadecylmethylammonium chloride, and methyl stearate. Examples of the film further include an alignment film capable of exhibiting an alignment function through irradiation with light. As the alignment film, a film formed by a rubbing treatment on the surface of a polymer layer is also preferable. The rubbing treatment is carried out by rubbing the surface of a polymer layer a few times in a predetermined direction, using paper or cloth. Preferred examples of the polymer for use for the alignment layer include polyimide, polyvinyl alcohol, and a polymerizable group-having polymer described in JP1997-152509A (JP-H09-152509A). The thickness of the alignment layer is not necessarily thick as long as it can provide an alignment function, and is preferably from 0.01 μm to 5 μm, and more preferably from 0.05 μm to 2 μm. The alignment film has a rubbing-treated surface which has been subjected to a rubbing treatment. As the rubbing treatment, a general rubbing treatment method can be used, and for example, it can be carried out by rubbing the surface of an alignment film by a rubbing roll. In an embodiment in which an alignment film is continuously formed on a support including a lengthwise polymer film, from the viewpoint of production suitability, the direction of the rubbing treatment (rubbing direction) preferably coincides with the longitudinal direction of the support. This also applies to a case where an optically anisotropic layer is directly formed on the surface of a polarizing film or the like.

As the alignment film, an alignment film formed by irradiating a photo-alignment material with polarized or non-polarized light, that is, a so-called photo-alignment film, can be used. It is preferable to impart the alignment regulating force to the photo-alignment film by a step of irradiating polarized light from the vertical (normal) or oblique direction, or by a step of irradiating non-polarized light from an oblique direction.

In the photo-alignment layer, in order to align the photo-alignment material by non-contact light irradiation as described above, non-uniform physical irregular shapes, such as rubbing, are less likely to occur. Therefore, light leakage is reduced in a liquid crystal display apparatus using an optical film prepared by using the photo-alignment film, and a high contrast can be realized. Depending on the use of the photo-alignment film, for example, it is possible to prepare an alignment film having excellent symmetry with a pre-tilt angle of 0° by light irradiation from the vertical direction. Depending on the use of the obtained alignment film, it is possible to horizontally align the liquid crystal compound in the polymerizable composition with excellent symmetry. As a result, an optical film including an optically anisotropic layer formed by using a photo-alignment film is particularly useful for optical compensation in a liquid crystal display apparatus for which a pre-tilt angle of the drive liquid crystal is not required, such as an IPS mode liquid crystal display apparatus.

Examples of the photo-alignment material for use in a photo-alignment film include azo compounds described in JP2006-285197A, JP2007-76839A, JP2007-138138A, JP2007-94071A, JP2007-121721A, JP2007-140465A, JP2007-156439A, JP2007-133184A, JP2009-109831A, JP3883848B, and JP4151746B; aromatic ester compounds described in JP2002-229039A; maleimide and/or alkenyl-substituted nadimide compounds having photo-alignment units described in JP2002-265541A and JP2002-317013A; photo-cross-linkable silane derivatives described in JP4205195B and JP4205198B; photo-cross-linkable polyimides, polyamides, and esters described in JP2003-520878A, JP2004-529220A, and JP4162850B; and photo-dimerizable compounds, in particular, a cinnamate compound, a chalcone compound, and a coumarin compound, described in JP1997-118717A (JP-H09-118717A), JP1998-506420 (JP-H10-506420A), JP2003-505561A, WO2010/150748A, JP2013-177561 A, and JP2014-12823A. Particularly preferred examples thereof include azo compounds, a photo-cross-linkable polyimide, a polyamide, an ester, a cinnamate compound, and a chalcone compound.

(Coating Method)

Examples of a method for applying a polymerizable composition on the surface of an alignment film or a polarizing film include known methods such as a curtain coating method, a dip coating method, a spin coating method, a printing coating method, a spray coating method, a slot coating method, a roll coating method, a slide coating method, a blade coating method, a gravure coating method, and a wire bar method.

In addition, the descriptions of JP2008-225281A and JP2008-026730A can be referred for the details of the method for producing the optically anisotropic layer.

(Alignment of Liquid Crystal Compound)

An alignment treatment in which the liquid crystal compound of the coating layer of the polymerizable composition may be aligned, prior to curing of the polymerizable composition, can be carried out by drying at room temperature or the like or by heating. The liquid crystal phase formed by the alignment treatment can generally be transferred by a change in temperature or pressure. In the case of the liquid crystal with a lyotropic property, the liquid crystal phase can also be transferred according to the amount of a solvent.

It is common that a temperature band in which a rod-shaped liquid crystal compound expresses a nematic phase is higher than a temperature band in which the rod-shaped liquid crystal compound expresses a smectic phase. Accordingly, it is preferable that the rod-shaped liquid crystal compound is transferred from the nematic phase to the smectic phase by heating the rod-shaped liquid crystal compound to a temperature band in which the rod-shaped liquid crystal compound expresses the nematic phase, and then lowering the heating temperature to a temperature band in which the rod-shaped liquid crystal compound expresses the smectic phase.

Furthermore, the smectic phase in the present specification refers to a state in which the molecules arranged in one direction have a layer structure. Further, the nematic phase refers to a state in which the constituent molecules of the phase have the alignment order but do not have a three-dimensional positional order. Checking whether the liquid crystal compound is fixed in the state of the smectic phase can be performed by observation by an X-ray diffraction pattern. If the liquid crystal compound is fixed in the state of the smectic phases, an X-ray diffraction pattern derived from the layer order is observed, and thus, it is possible to determine the state of the liquid crystal compound fixed. For the optically anisotropic layer, a smectic liquid crystal may be fixed in a state showing the nematic phase. Checking whether the liquid crystal compound is fixed in the state of a nematic phase can also be performed by observation by an X-ray diffraction pattern. If the liquid crystal compound is fixed in the state of a nematic phase, a sharp peak on the low-angle side derived from layer formation was not observed, but only a broad halo peak is observed on the wide-angle side, and thus, it is possible to determine the state of the liquid crystal compound fixed.

In a temperature band in which the rod-shaped liquid crystal compound expresses a nematic phase, it is necessary to heat the rod-shaped liquid crystal compound for a pre-determined time until the compound forms a mono-domain. The heating time is preferably from 10 seconds to 20 minutes, more preferably from 10 seconds to 10 minutes, and most preferably from 10 seconds to 5 minutes.

In a temperature band in which the rod-shaped liquid crystal compound expresses a smectic phase, it is necessary to heat the rod-shaped liquid crystal compound for a pre-determined time until the compound expresses the smectic phase. The heating time is preferably from 10 seconds to 20 minutes, more preferably from 10 seconds to 10 minutes, and most preferably from 10 seconds to 5 minutes.

[Fixation of Alignment State]

Fixation of an alignment state can be carried out by photopolymerization through thermal polymerization or irradiation with active energy rays (ultraviolet rays), and can also be carried out by appropriately selecting a polymerizable group or a polymerization initiator that is suitable for the polymerization. Further, a polymerization reaction by irradiation with ultraviolet rays can be preferably used, taking into consideration production suitability and the like. If the irradiation amount of ultraviolet rays is small, the polymerizable rod-shaped liquid crystal compound thus unpolymerized remains, which leads to optical characteristics that indicate a temperature change or are deteriorated over time.

Therefore, it is preferable to determine the irradiation condition such that the ratio of the remaining polymerizable rod-shaped liquid crystal compounds becomes 5% or less. The irradiation condition may depend on the formulation of the polymerizable composition or the film thickness of the optically anisotropic layer, but is preferably carried out at an irradiation amount of 200 mJ/cm$^2$ or more as a standard.

<<Use of Optical Film>>

The optical film of the present invention is useful as, for example, an optically compensatory film that optically compensates a liquid crystal cell, or as a broadband λ/4 plate, or a phase difference plate of a λ/2 plate or a λ/4 plate, each of which is used in an organic EL display apparatus. The broadband λ/4 plate, or the phase difference plate of a λ/2 plate or a λ/4 plate can be used as an anti-reflection plate in combination with a polarizing film in the organic EL display apparatus.

In particular, the optical film of the present invention is an A-plate or a quasi-A-plate, having a reduced inclination angle, and therefore, it can also be preferably used as an optically compensatory film of an IPS type or FFS type liquid crystal display apparatus using a photo-alignment film with a pre-tilt angle of 0°.

The optical film of the present invention is most preferably a positive A-plate, in which the retardation values, Re(450), Re(550), and Re(650), measured at each wavelength of 450 nm, 550 nm, and 650 nm, satisfy the following expressions (A-1) to (A-3):

$$100 \leq Re(550) \leq 180 \text{ nm} \quad \text{Expression (A-1)}$$

$$0.70 \leq Re(450)/Re(550) \leq 0.90 \quad \text{Expression (A-2)}$$

$$1.00 \leq Re(650)/Re(550) \leq 1.30 \quad \text{Expression (A-3)}$$

The compound having performance (performance in the A-plate optical film) satisfying the following expressions (A-1a) to (A-3c) can express a wide range of reverse wavelength dispersion by mixing the compound with other liquid crystal compounds, leading to enhanced display performance, which is thus preferable.

$$0 \leq Re(450)/Re(550) \leq 0.8 \quad \text{Expression (A-1a)}$$

$$1.00 \leq Re(650)/Re(550) \leq 1.40 \quad \text{Expression (A-2b)}$$

$$Re(x)/Re(550)=0 \quad \text{Expression (A-3c)}$$

In Expression (A-3c), x represents a wavelength of 250 nm or more and less than 550 nm.

Examples of the compound having performance satisfying the expressions (A-1a) to (A-3c), for example, the compound represented by General Formula (1), include cases of the compound represented by General Formula (3), having a hydrogen bonding substituent in Y or Z, in which a and b are both 0, but the present invention is not limited thereto.

Further, in order to adjust the wavelength dispersion, the aforementioned other liquid crystal compounds may be appropriately mixed. Examples thereof include a compound represented by General Formula (101). As such, by mixing at least two kinds of these other liquid crystal compounds, the Re(450)/Re(550) can be adjusted to 0.10 to 1.11 and the Re(650)/Re(550) can be adjusted to 0.94 and 1.26.

[Hydrogen Bonding Substituent]

In the present specification, the hydrogen bonding substituent is formed of a hydrogen bond donating group and a hydrogen bond accepting group. It is more preferable that the hydrogen bond donating group and the hydrogen bond accepting group are positioned at positions capable of forming a hydrogen bond by mutual combination, and it is still more preferable that the hydrogen bond donating group and the hydrogen bond accepting group form a hydrogen bond.

As the hydrogen bond donating group, an amino group, an acylamino group, an alkoxycarbonylamino group, an aryloxycarbonylamino group, a sulfonylamino group, a hydroxy group, a mercapto group, a carboxyl group, a methylene group substituted with an electron withdrawing group, and a methine group substituted with an electron withdrawing group are preferable; a sulfonylamino group, an acylamino group, an amino group, a hydroxyl group, and a methine group substituted with an electron withdrawing group are more preferable; and an amino group and a methine group substituted with an electron withdrawing group are still more preferable.

The hydrogen bond accepting group means a compound or linking group, containing an electron accepting structure that accepts a hydrogen atom at a time of forming a hydrogen bond (hereinafter referred to as a hydrogen accepting structure) and the structure as a partial structure.

Examples of the group with a hydrogen bond accepting structure include a hetero atom having unshared electron pairs on a hetero ring contained inside, a hydroxy group, an aldehyde, a ketone, a carboxylic ester, a carboxylic amide, a lactone, a lactam, a sulfonic amide, a phosphoric amide, a urethane, a urea, an ether structure (particularly a polymer structure having an oxygen atom contained in the polyether structure), an aliphatic amine, an aromatic amine, and a carboxylic amide. More preferred examples of the hydrogen bond accepting group include a hetero atom having unshared electron pairs on a hetero ring contained inside.

As the hydrogen bonding substituent contained in the Y—Z site, for example, those in which the hydrogen bond donating group is an —NH— bond and the hydrogen bond accepting group is a hetero atom having unshared electron pairs on a hetero ring contained inside are preferable.

[Positive C-Plate]

Moreover, preferable is also an embodiment in which a positive C-plate with a retardation value, Rth(550), in the thickness direction, as measured at a wavelength of 550 nm, satisfies the following Expression (C-1) and is laminated on the optical film of the present invention. By adopting this embodiment, for example, problems with the anti-reflection for organic EL or the color change or light leakage in the oblique direction for an optical compensatory film of an IPS type can be significantly improved. In particular, with the anti-reflection for organic EL, the problems with a front-surface reflectivity can also be improved.

$$-180 \leq Rth(550) \leq -10 \quad \text{Expression (C-1)}$$

EXAMPLES

Hereinafter, the features of the present invention will be described in more detail with reference to Examples and Comparative Examples. The materials, amounts to be used, ratios, treatment contents, treatment procedures, and the like shown in Examples below can be appropriately modified without departing from the spirit of the present invention. Accordingly, the scope of the present invention is not intended to be restrictively interpreted by the specific examples shown below.

<Synthesis of Compound 25-D>

According to the following scheme, a compound (25-D) was synthesized.

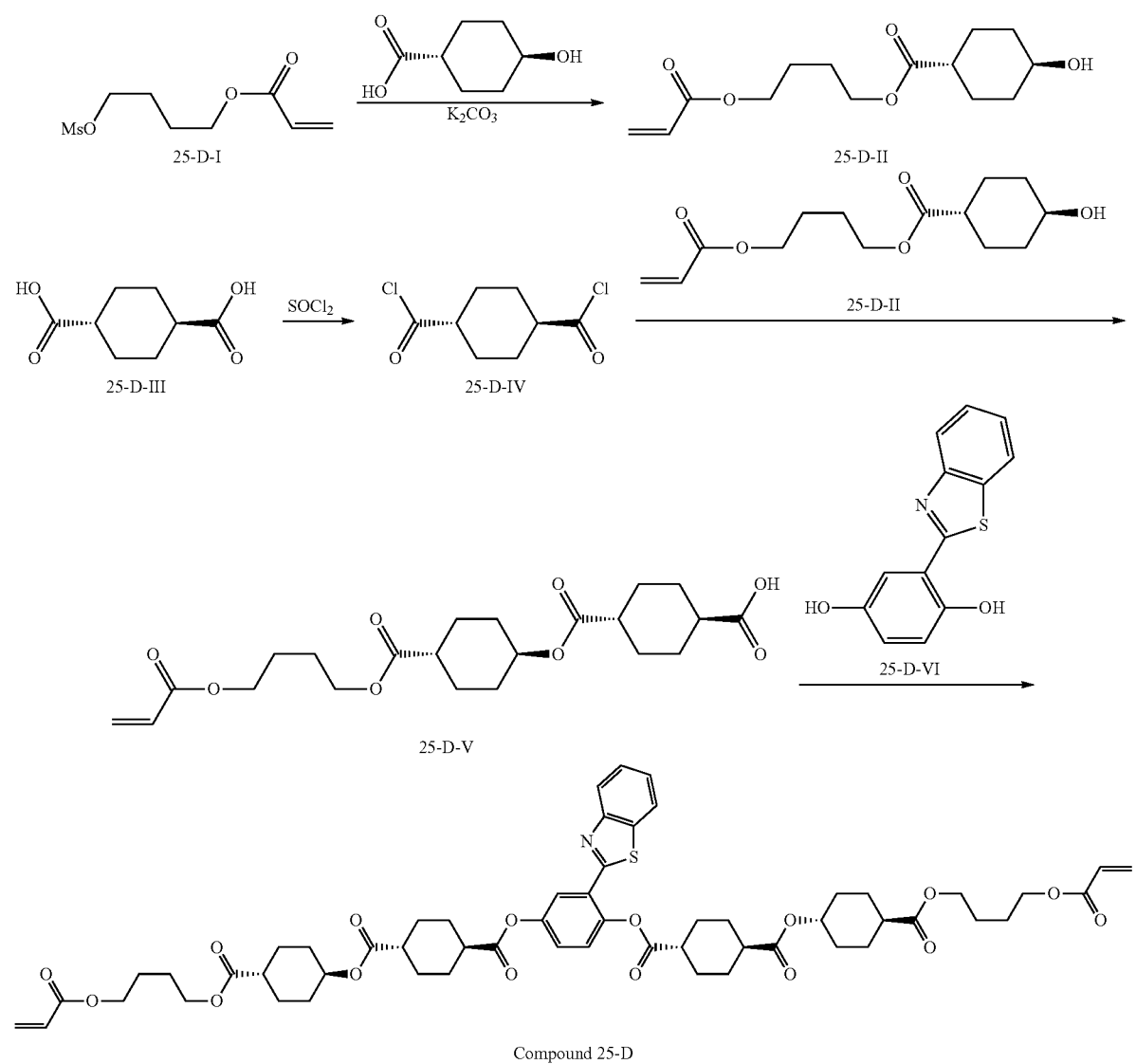

A compound 25-D-I was synthesized by the method described in the paragraph <0108> of JP4397550B and isolated by concentrating the solvent under reduced pressure.

A solution of 25-D-I (22.0 g, 91.0 mmol) in DMAc (N,N-dimethylacetamide) (18 mL) was placed in a flask, 4-hydroxy cyclohexane carboxylic acid (14.2 g, 97.2 mmol), dibutylhydroxytoluene (BHT) (356 mg), potassium iodide (1.6 g, 9.8 mmol), and triethylamine (14.8 ml, 105.4 mmol) were added thereto, and the mixture was heated to 70° C.

The mixture was stirred at 70° C. for 6 hours and then cooled to room temperature, and pure water and ethyl acetate was added thereto. The organic layer which had been extracted with ethyl acetate was washed with a saturated aqueous sodium bicarbonate solution, a 1 M aqueous hydrochloric acid solution, and saturated physiological saline, and the solvent was removed using a rotary evaporator. The residue was purified by column chromatography using silica gel to obtain 25-D-II (15.6 g, 71%).

7.4 g (0.085 mol) of 25-D-III trans-1,4-cyclohexanedicarboxylate and 25 mL of toluene were added into a flask, and 0.2 mL of N,N-dimethyl formamide and 8 mL of thionyl chloride were added thereinto at room temperature. The mixture was heated and stirred in an oil bath at an oil temperature of 70° C. for 3 hours. After evaporating the solvent, 50 mL of tetrahydrofuran was added to the mixture, and then 11.6 g (0.043 mol) of the compound 25-D-II was added thereto at room temperature. 3.5 mL (0.044 mol) of pyridine was added dropwise thereto with a syringe while cooling the mixture to 0° C. or lower. After dropwise addition, the solution was stirred at room temperature for 2 hours, and then 10 mL of pyridine, 100 mL of water, and 100 mL of ethyl acetate were added thereto to extract the product. The organic layer was dried over sodium sulfate and concentrated. The residue was purified by silica gel column chromatography to obtain 25-D-V (7.1 g, 37%).

A solution of 25-D-V (3.1 g, 7.2 mmol) in ethyl acetate (10 ml) was placed in a flask, BHT (20 mg) and DMAc (2.3 ml) were added thereto, and the internal temperature was cooled to 5° C. To the mixture was added dropwise thionyl chloride (0.53 ml, 7.3 mmol) with a syringe while not raising the internal temperature to 10° C. or higher. While keeping the internal temperature at 5° C., the mixture was stirred for 1 hour, and then diisopropylethylamine (0.98 ml, 5.6 mmol) was added dropwise thereto. Subsequently, a solution of 25-D-VI (0.8 g, 3.3 mmol) and DMAP (N,N-dimethyl-4-aminopyridine) (20 mg, 0.15 mmol) in THF (tetrahydrofuran) (5 ml) was added dropwise thereto. Thereafter, diisopropyl ethylamine (2.6 mL, 15.1 mmol) was added dropwise to the mixture while not raising the internal temperature to 10° C. or higher. The solution after dropwise addition was stirred at room temperature for 2 hours, and then methanol (1 ml) was added thereto to stop the reaction. Then, water and chloroform were added to the mixture. The solvent was removed with a rotary evaporator from the organic layer which had been extracted with chloroform, and the residue was purified by column chromatography using silica gel to obtain 25-D (1.4 g, 39%).

$^1$H-NMR (solvent: CDCl$_3$) δ (ppm): 1.3-1.7 (m, 16H), 1.7-1.8 (m, 8H), 1.9-2.2 (m, 16H), 2.2-2.4 (m, 4H), 2.5-2.8 (m, 2H), 4.1-4.3 (m, 8H), 4.7-4.8 (m, 2H), 5.8 (d, 1H), 6.1 (dd, 1H), 6.4 (d, 1H), 7.1-7.3 (m, 2H), 7.4-7.5 (m, 1H), 7.5-7.6 (m, 1H), 7.9 (d, 1H), 8.0-8.1 (m, 2H)

The phase transition temperature of the obtained exemplary compound (25-D) was determined through texture observation with a polarizing microscope, and it was found that the crystalline phase was changed to a nematic liquid crystal phase at 110° C., and when the temperature was higher than 168° C., the phase was changed to an isotropic liquid phase.

<Synthesis of Compound 2-B>

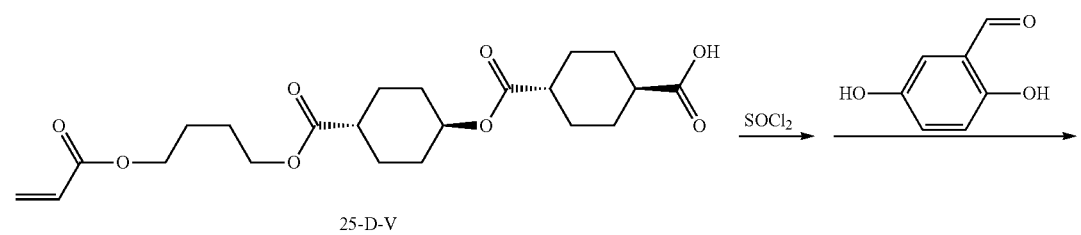

25-D-V

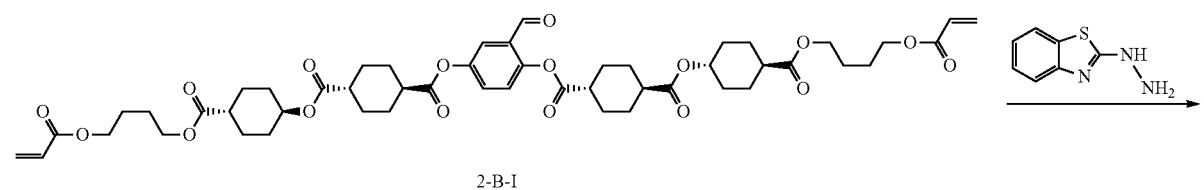

2-B-I

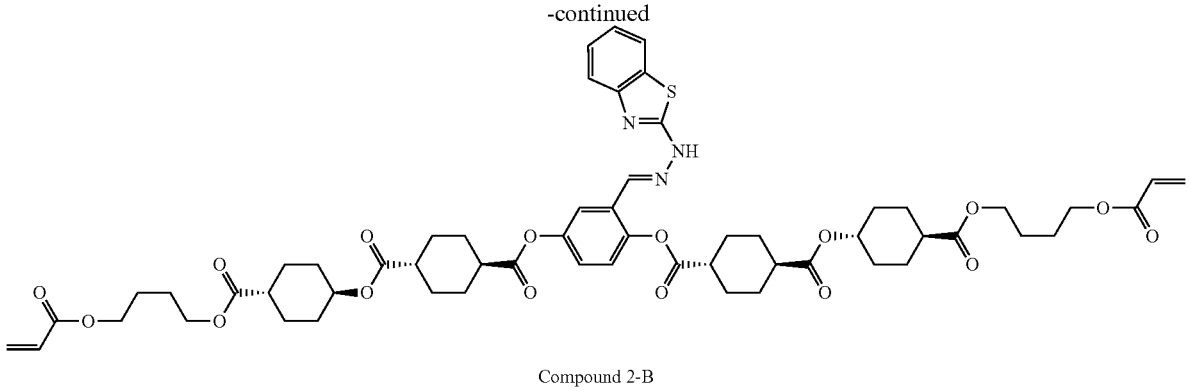

Compound 2-B

A solution of 25-D-V (3.1 g, 7.2 mmol) in ethyl acetate (10 ml) was placed in a flask, and BHT (20 mg) and DMAc (2.3 ml) were added thereinto, and the internal temperature was cooled to 5° C. To the mixture was added dropwise thionyl chloride (0.53 ml, 7.3 mmol) with a syringe while not raising the internal temperature to 10° C. or higher. After stirring the mixture at 5° C. for 1 hour, diisopropylethylamine (0.98 ml, 5.6 mmol) was added dropwise thereto, and subsequently a solution of 2,5-dihydroxybenzaldehyde (450 mg, 3.3 mmol) and DMAP (20 mg, 0.15 mmol) in THF (5 ml) were added dropwise to the mixture. Thereafter, diisopropyl ethylamine (2.6 mL, 15.1 mmol) was added dropwise thereto while not raising the internal temperature to 10° C. or higher. The solution after dropwise addition was stirred at room temperature for 2 hours, methanol (1 ml) was then added thereto to stop the reaction, and subsequently water and chloroform were added to the mixture. The solvent was removed with a rotary evaporator from the organic layer which had been extracted with chloroform, and the residue was purified by column chromatography using silica gel to obtain 2-B-I (2.0 g, 64%).

A solution of 2-B-I (0.36 g, 0.379 mmol) in THF (5 ml) was placed in a flask, BHT (10 mg), 10-camphorsulfonic acid (0.9 mg, 0.004 mmol), and 2-hydrazinobenzothiazole (75 mg, 0.454 mmol) were added thereto, and the mixture was stirred at room temperature for 3 hours. To the solution after stirring were added water and chloroform, and the organic layer was recovered. The recovered organic layer was washed with a saturated aqueous sodium bicarbonate solution and a saturated physiological saline solution. The solvent was removed with a rotary evaporator and the residue was purified by column chromatography using silica gel to obtain 2-B (0.2 g, 48%).

$^1$H-NMR (solvent: DMSO-d$_6$) δ (ppm): 1.3-1.6 (m, 16H), 1.6-1.7 (m, 8H), 1.9 (m, 8H), 2.0 (m, 4H), 2.1-2.2 (m, 4H), 2.3-2.4 (m, 4H), 2.6-2.8 (m, 2H), 4.0 (m, 4H), 4.1 (m, 4H), 4.6 (m, 2H), 5.9 (dd, 1H), 6.2 (dd, 1H), 6.3 (dd, 1H), 7.1 (m, 1H), 7.2 (m, 2H), 7.3 (m, 1H), 7.5 (d, 1H), 7.6 (d, 1H), 7.8 (d, 1H), 8.1 (s, 1H), 12.5 (s, 1H)

The phase transition temperature of the obtained exemplary compound (2-B) was determined through texture observation with a polarizing microscope, and it was found that the crystalline phase was changed to a nematic liquid crystal phase at 99° C., and when the temperature was higher than 272° C., the phase was changed to an isotropic liquid phase.

<Synthesis of Compound 5-B>

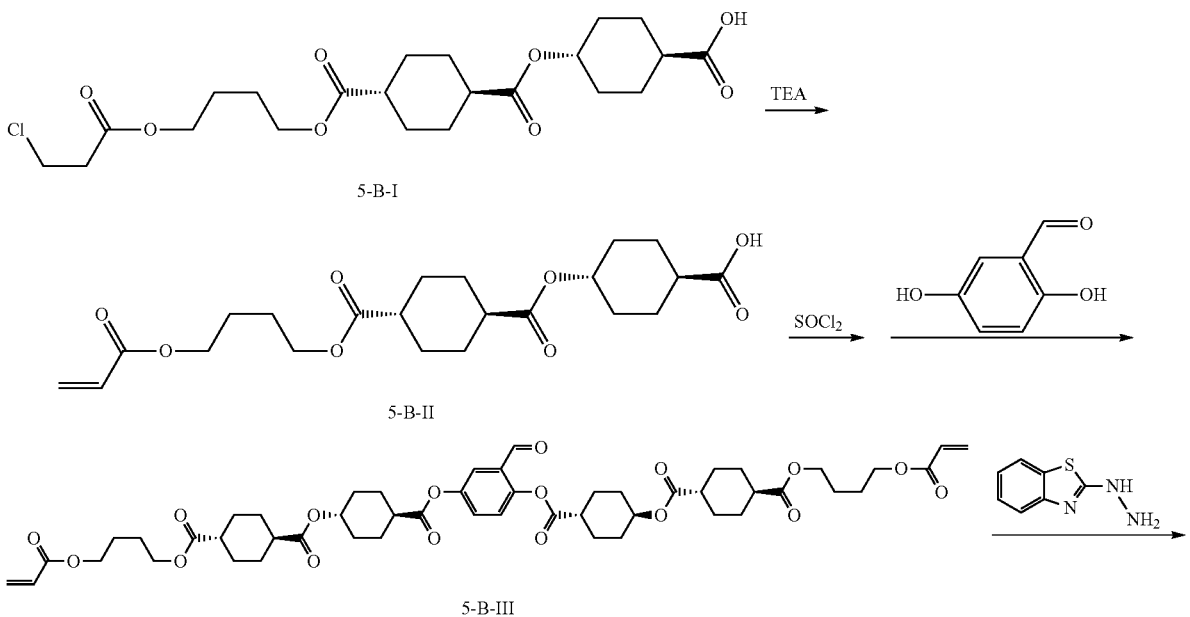

-continued

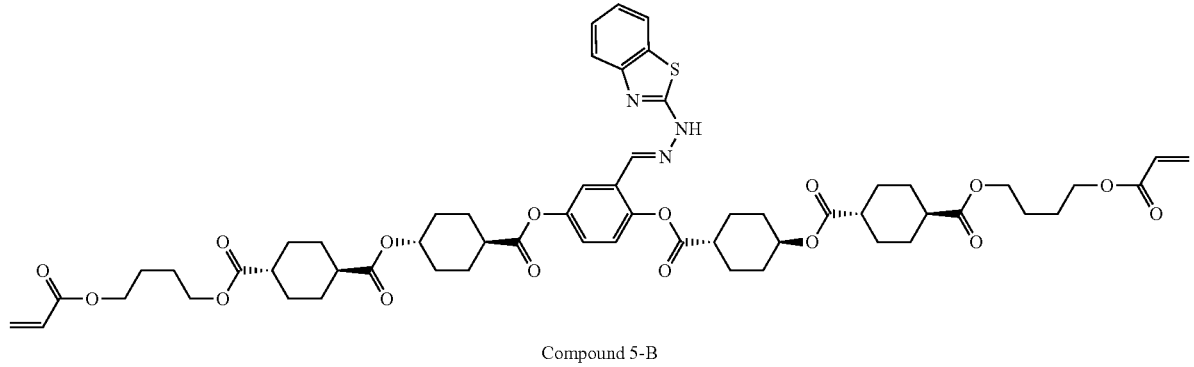

Compound 5-B

The compound 5-B-I was synthesized by the method described in the paragraphs <0124> to <0137> of JP2009-179563A.

A solution of 5-B-I (5.4 g, 12 mmol) in THF was placed in a flask, BHT (10 mg) and TEA (triethylamine) (5.0 ml) were added thereto, and the mixture was stirred at room temperature for 3 hours. Thereafter, the solvent was concentrated under reduced pressure and the concentrate was then purified by silica gel column chromatography to obtain a desired compound 5-B-II (2.0 g, 40%).

To a solution of 5-B-II (1.5 g, 3.6 mmol) in ethyl acetate (5 ml) were added BHT (10 mg) and DMAc (1.3 ml), and the internal temperature was cooled to 5° C. To the mixture was added dropwise thionyl chloride (0.27 ml, 3.7 mmol) while not raising the internal temperature to 10° C. or higher. The solution after dropwise addition was stirred at 5° C. for 1 hour, diisopropylethylamine (0.49 ml, 2.8 mmol) was then added dropwise thereto with a syringe, and subsequently, a solution of 2,5-dihydroxybenzaldehyde (225 mg, 1.7 mmol) and DMAP (10 mg, 0.08 mmol) in THF (3 ml) was added dropwise to the mixture with a syringe. Thereafter, diisopropyl ethylamine (1.3 mL, 7.6 mmol) was added dropwise thereto with a syringe while not raising the internal temperature to 10° C. or higher. After stirring the mixture at room temperature for 2 hours, methanol (1 ml) was added thereto to stop the reaction, and subsequently water and chloroform were added to the mixture. The solvent was removed from the organic layer which had been extracted with chloroform with a rotary evaporator and the residue was purified by column chromatography using silica gel to obtain 5-B-III (0.98 g, 61%).

To a solution of 5-B-III (0.9 g, 0.95 mmol) in THF (15 ml) were added BHT (5 mg), 10-camphorsulfonic acid (4.5 mg, 0.02 mmol) and 2-hydrazinobenzothiazole (190 mg, 1.15 mmol), and the mixture was stirred at room temperature for 3 hours. To the solution after stirring were added water and chloroform, and the organic layer was recovered. The recovered organic layer was washed with a saturated aqueous sodium bicarbonate solution and a saturated physiological saline solution. The solvent was removed with a rotary evaporator and the residue was purified by column chromatography using silica gel to obtain 5-B (0.5 g, 52%).

According to the following scheme, a compound (8-B) was synthesized.

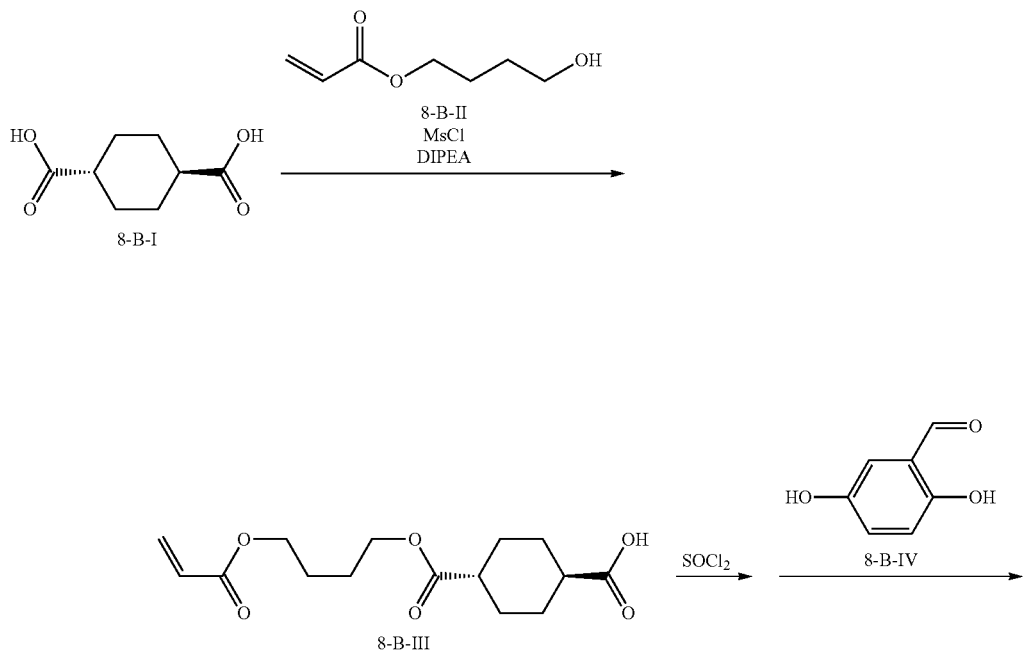

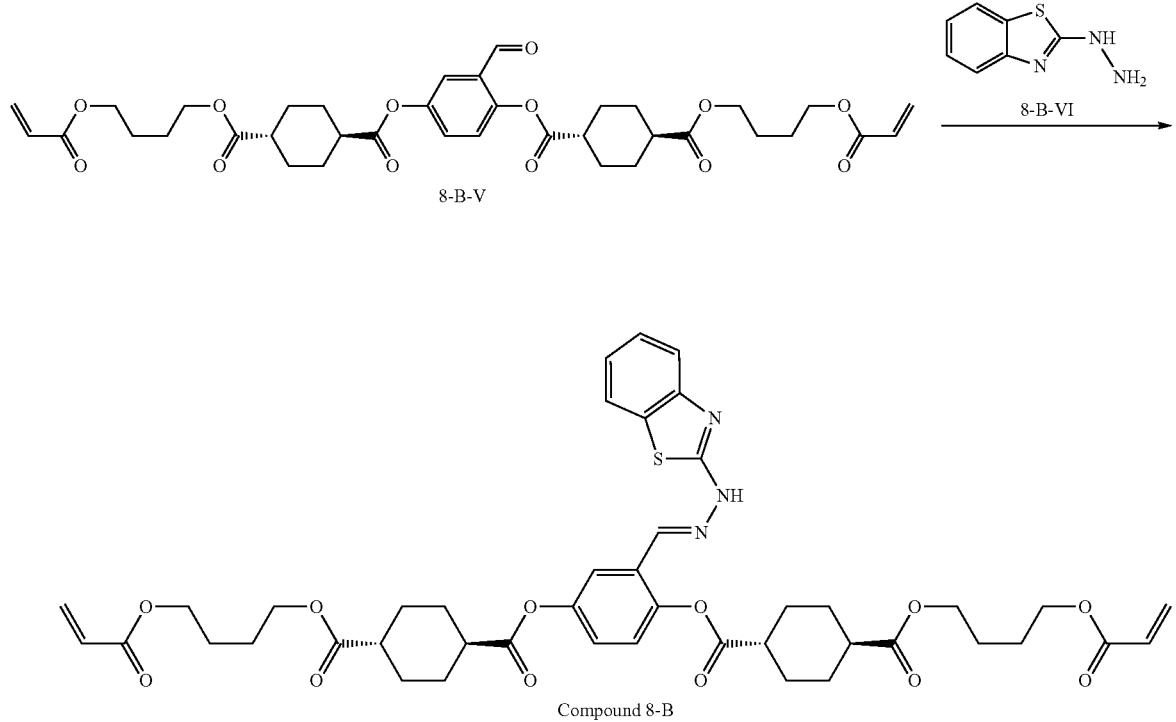

Compound 8-B

A solution of 8-B-I trans-1,4-cyclohexanedicarboxylate (5.0 g, 0.022 mol) in THF (36 ml) was placed in a flask, and BHT (120 mg) was added thereto. To the mixture was added methanesulfonic chloride (0.93 ml, 0.012 mol), and then triethylamine (1.83 ml, 0.013 mol) added dropwise thereto with a syringe while not raising the internal temperature to 25° C. or higher. The solution after dropwise addition was stirred for 2 hours, and then DMAP (0.13 g) and 8-B-II 4-hydroxybutyl acrylate (1.57 g, 0.011 mol) were added thereto. Triethylamine (1.83 ml, 0.013 mol) was added dropwise to the mixture over 10 minutes. The solution after dropwise addition was stirred at room temperature for 4 hours, and then water and ethyl acetate were added thereto to stop the reaction. The organic layer which had been extracted with ethyl acetate was washed with a 1 M aqueous hydrochloric acid solution, a saturated aqueous sodium bicarbonate solution, a 1 M aqueous hydrochloric acid solution, and saturated physiological saline, and the solvent was removed using a rotary evaporator. The residue was purified by column chromatography using silica gel to obtain 8-B-III (2.5 g, 75%).

A solution of 8-B-III (6.0 g, 20.1 mmol) in ethyl acetate (35 ml) was placed in a flask, BHT (70 mg) and DMAc (10 ml) were added thereto, and the internal temperature was cooled to 5° C. To the mixture was added dropwise thionyl chloride (2.51 g, 21.1 mmol) with a syringe while not raising the internal temperature to 10° C. or higher. The solution after dropwise addition was stirred at 5° C. for 1 hour, diisopropylethylamine (19.8 g, 15.3 mmol) was then added dropwise, and subsequently, a solution of 2,5-dihydroxy-benzaldehyde (1.32 g, 9.6 mmol) and DMAP (60 mg, 0.49 mmol) in THF (20 ml) was added dropwise to the mixture with a syringe. Thereafter, diisopropyl ethylamine (5.6 g, 43.1 mmol) was added dropwise thereto while not raising the internal temperature to 10° C. or higher. The solution after dropwise addition was stirred at room temperature for 2 hours, methanol (1 ml) was then added thereto to stop the reaction, and subsequently water and chloroform were added to the mixture. The solvent was removed with a rotary evaporator from the organic layer which had been extracted with chloroform, and the residue was purified by column chromatography using silica gel to obtain 8-B-V (3.5 g, 52%).

To a solution of 8-B-V (2.0 g, 2.86 mmol) in THF (30 ml) were added BHT (15 mg), 10-camphorsulfonic acid (6.6 mg, 0.03 mmol) and 2-hydrazinobenzothiazole (0.57 g, 3.43 mmol), and the mixture was stirred at room temperature for 3 hours. To the solution after stirring were added water and chloroform, and the organic layer was recovered. The recovered organic layer was washed with a saturated aqueous sodium bicarbonate solution and a saturated physiological saline solution. The solvent was removed with a rotary evaporator and the residue was purified by column chromatography using silica gel to obtain 8-B (1.5 g, 62%).

$^1$H-NMR (solvent: DMSO-$d_6$) δ (ppm): 1.4-1.6 (m, 8H), 1.6-1.7 (m, 8H), 2.0 (m, 4H), 2.1-2.2 (m, 4H), 2.3-2.5 (m, 2H), 2.6-2.8 (m, 2H), 4.1 (m, 4H), 4.1 (m, 4H), 6.0 (dd, 1H), 6.2 (dd, 1H), 6.3 (dd, 1H), 7.1 (m, 1H), 7.2 (m, 2H), 7.3 (m, 1H), 7.5 (br, 1H), 7.6 (d, 1H), 7.8 (d, 1H), 8.1 (s, 1H), 12.5 (s, 1H)

The phase transition temperature of the obtained exemplary compound (8-B) was determined through texture observation with a polarizing microscope, and it was found that the compound showed a nematic liquid crystal phase at a temperature from room temperature to 125° C., and when the temperature was higher than 125° C., the phase was changed to an isotropic liquid phase.

According to the following scheme, a compound (44-A) was synthesized.

<Synthesis of Compound 44-A> and chloroform, and the organic layer was recovered. The recovered organic layer was washed with a saturated aqueous sodium bicarbonate solution and a saturated physiological saline solution. The solvent was removed with a rotary evaporator and the residue was purified by column chromatography using silica gel to obtain 44-A (0.28 g, 40%).

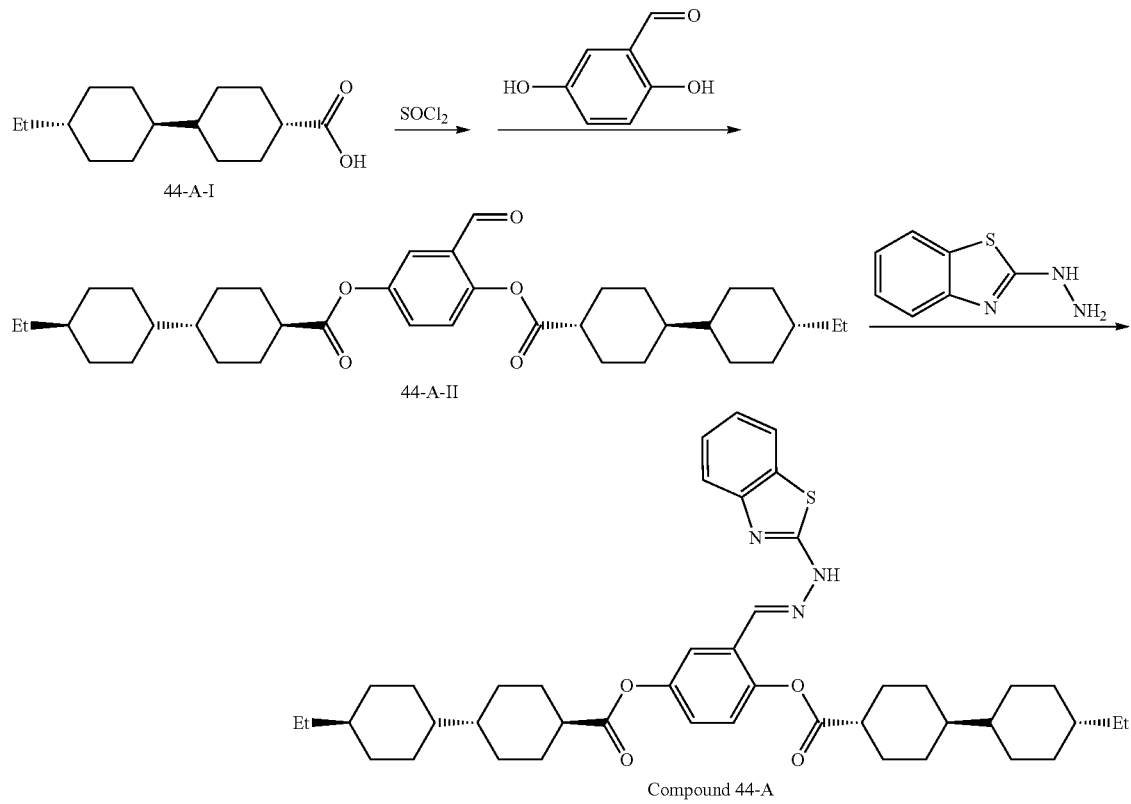

Compound 44-A

To a solution of 44-A-I (0.86 g, 3.6 mmol) (manufactured by Yantai valliant Fine Chem.) in ethyl acetate (5 ml) were added BHT (10 mg) and DMAc (1.3 ml), and the internal temperature was cooled to 5° C. To the mixture was added dropwise thionyl chloride (0.27 ml, 3.7 mmol) while not raising the internal temperature to 10° C. or higher. The solution after dropwise addition was stirred at 5° C. for 1 hour, diisopropylethylamine (0.49 ml, 2.8 mmol) was then added dropwise, and subsequently, a solution of 2,5-dihydroxybenzaldehyde (225 mg, 1.7 mmol) and DMAP (10 mg, 0.08 mmol) in THF (3 ml) was added dropwise to the mixture. Thereafter, diisopropyl ethylamine (1.3 mL, 7.6 mmol) was added dropwise thereto while not raising the internal temperature to 10° C. or higher. The solution after dropwise addition was stirred at room temperature for 2 hours, methanol (1 ml) was then added thereto to stop the reaction, and subsequently water and chloroform were added to the mixture. The solvent was removed with a rotary evaporator from the organic layer which had been extracted with chloroform and the residue was purified by column chromatography using silica gel to obtain 44-A-II (0.69 g, 70%).

To a solution of 4-A-II (0.55 g, 0.95 mmol) in THF (15 ml) were added BHT (5 mg), 10-camphorsulfonic acid (4.5 mg, 0.02 mmol) and 2-hydrazinobenzothiazole (190 mg, 1.15 mmol), and the mixture was stirred at room temperature for 3 hours. To the solution after stirring were added water (Preparation of Optical Film 1)
<Saponification of Support>

A commercially available triacetyl cellulose film "Z-TAC" (manufactured by Fujifilm Corporation) was used as a support. The support was allowed to pass through dielectric heating rolls at a temperature adjusted to 60° C. to elevate the temperature of the film surface of the support to 40° C., and then an alkali solution having the composition shown below was applied onto one surface of the film in a coating amount of 14 ml/m$^2$, using a bar coater. Thereafter, the support was heated to 110° C. and transported below a steam-type far infrared ray heater manufactured by Noritake Co., Ltd. for 10 seconds. Subsequently, using the same bar coater, pure water was applied onto the surface which had been coated with the alkali solution in an amount of 3 ml/m$^2$. Then, washing with water using a fountain coater and then dehydration using an air knife were repeated three times, respectively. Subsequently, the film was transported into a drying zone at 70° C. for 10 seconds, and dried therein to prepare an alkali saponification-treated transparent support.

| Composition of Alkali Solution (Part by Mass) | |
|---|---|
| Potassium hydroxide | 4.7 parts by mass |
| Water | 15.8 parts by mass |
| Isopropanol | 63.7 parts by mass |

| Composition of Alkali Solution (Part by Mass) | |
|---|---|
| Surfactant SF-1: $C_{14}H_{29}O(CH_2CH_2O)_{20}H$ | 1.0 part by mass |
| Propylene glycol | 14.8 parts by mass |

<Preparation of Alignment Film 1>

Using the obtained transparent support, a coating liquid for forming an alignment film 1 having the following composition was applied onto the alkali saponification-treated surface with a wire bar. The coated surface was dried with hot air at 60° C. for 60 seconds and then with hot air at 100° C. for 120 seconds to form an alignment film 1.

| Composition of Coating Liquid for Forming Alignment Film 1 | |
|---|---|
| Material 1 for photo-alignment below | 1.0 part by mass |
| Butoxyethanol | 33 parts by mass |

| Composition of Coating Liquid for Forming Alignment Film 1 | |
|---|---|
| Propylene glycol monomethyl ether | 33 parts by mass |
| Water | 33 parts by mass |

Material 1 for photo-alignment

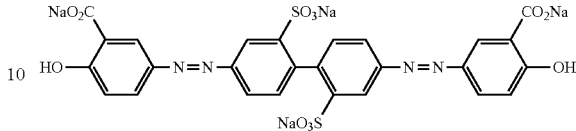

Example 1

Preparation of Optically Anisotropic Layer 1

Subsequently, the following coating liquid 1 for an optically anisotropic layer was prepared.

| Composition of coating liquid 1 for optically anistropic layer | |
|---|---|
| Liquid crystal compound 2-B | 15 parts by mass |
| Photopolymerization initiator (Irgacure 819, manufactured by Ciba Specialty Chemicals Inc.) | 0.45 parts by mass |
| Fluorine-containing compound A | 0.12 parts by mass |
| Chloroform | 140 parts by mass |

Liquid crystal compound 2-B

Compound 2-B

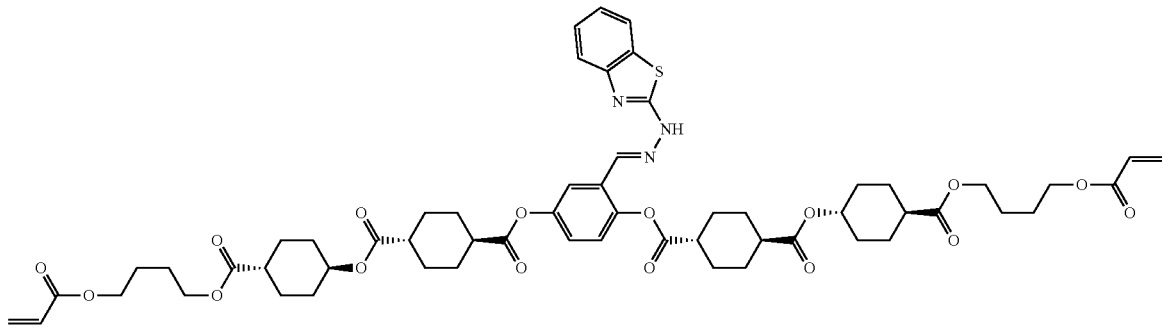 [SMILES: C=CC(=O)OCCCCOC(=O)[C@H]1CC[C@H](OC(=O)[C@H]2CC[C@H](C(=O)Oc3ccc(OC(=O)[C@H]4CC[C@H](C(=O)O[C@H]5CC[C@H](C(=O)OCCCCOC(=O)C=C)CC5)CC4)c(/C=N/Nc4nc5ccccc5s4)c3)CC2)CC1]

Fluorine-containing compound A

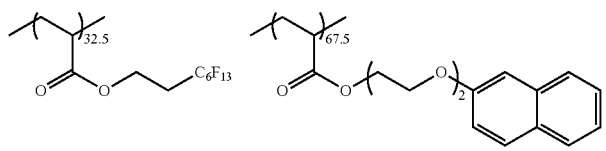

The prepared alignment film 1 was irradiated with ultraviolet rays using an air-cooled metal halide lamp (manufactured by Eye Graphics Co, Ltd.) at 160 W/cm² under an atmosphere of room temperature. At this time, a wire grid polarizer (ProFlux PPL02, manufactured by Moxtek Inc.) was set to be in parallel to the surface of the alignment film 1 to perform exposure. The irradiation intensity of the ultraviolet rays used herein was set to 100 mW/cm² in a UV-A region (cumulatively calculated at a wavelength of 380 nm to 320 nm) and the irradiation dose was set to 1000 mJ/cm² in the UV-A region.

Subsequently, the coating liquid 1 for an optically anisotropic layer was applied onto the photo-alignment treated surface which had been irradiated with ultraviolet rays, using a bar coater. The coated surface was heated and aged at a temperature of the film surface of 190° C. for 30 seconds and cooled to 150° C., and then irradiated with ultraviolet rays at 1000 mJ/cm² using an air-cooled metal halide lamp (manufactured by Eye Graphics Co., Ltd.) at 70 mW/cm² under an atmospheric air to fix the alignment state, thereby forming an optically anisotropic layer 1 and obtaining an optical film 1. In the optically anisotropic layer 1 thus formed, a liquid crystal compound 2-B was aligned orthogonal to the polarization irradiation direction and thus the slow axis direction was also orthogonal to the polarization irradiation direction. The optical characteristics of the optical film 1 were confirmed by using an automatic birefringence meter (KOBRA-21ADH, manufactured by Oji Scientific Instruments), and it was found that at a wavelength of 550 nm, the Re was 125 nm, the Rth was 65 nm, the Re(450)/Re(550) was 0.70, and the Re(650)/Re(550) was 1.07.

Example 2

Preparation of Optical Film 2

Preparation of Optically Anisotropic Layer 2

By changing the liquid crystal compound 2-B of the coating liquid 1 for an optically anisotropic layer used in Example 1 to 5-B, a coating liquid 2 for an optically anisotropic layer was prepared. In the same manner as in Example 1 except that the coating liquid 1 for an optically anisotropic layer used in Example 1 was changed to the coating liquid 2 for an optically anisotropic layer, an optically anisotropic layer 2 was formed and an optical film 2 was obtained. The optical characteristics of the optical film 2 were confirmed by using an automatic birefringence meter (KOBRA-21 ADH, manufactured by Oji Scientific Instruments), and it was found that at a wavelength of 550 nm, the Re was 130 nm, the Rth was 65 nm, the Re(450)/Re(550) was 0.74, and the Re(650)/Re(550) was 1.06.

compound 5-B

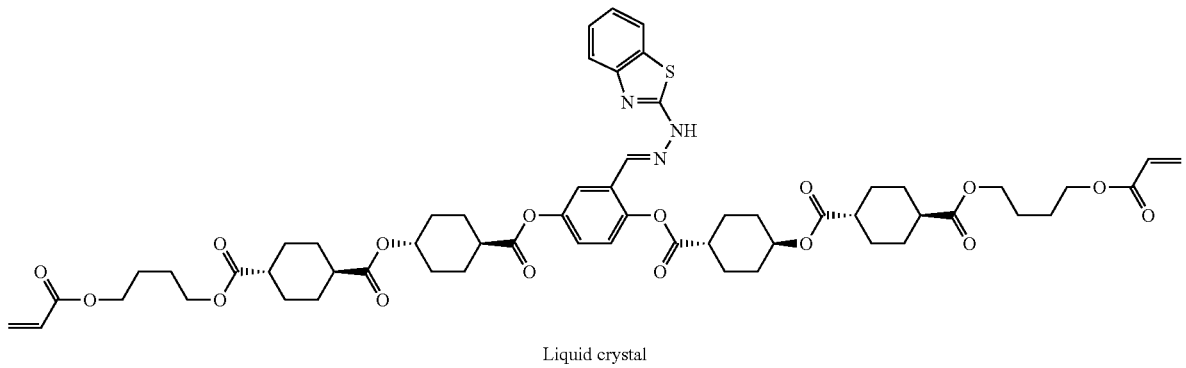

Liquid crystal

Example 3

Preparation of Optical Film 3

Preparation of Optically Anisotropic Layer 3

By changing the liquid crystal compound 2-B of the coating liquid 1 for an optically anisotropic layer used in Example 1 to a liquid crystal mixture formed by mixing the compound 8-B and the compound B at a ratio of 80 to 20 (mass ratio), a coating liquid 3 for an optically anisotropic layer was prepared. In the same manner as in Example 1 except that the coating liquid 1 for an optically anisotropic layer used in Example 1 was changed to the coating liquid 3 for an optically anisotropic layer, an optically anisotropic layer 3 was formed and an optical film 3 was obtained. The optical characteristics of the optical film 3 were confirmed by using an automatic birefringence meter (KOBRA-21ADH, manufactured by Oji Scientific Instruments), and it was found that at a wavelength of 550 nm, the Re was 140 nm, the Rth was 70 nm, the Re(450)/Re(550) was 0.78, and the Re(650)/Re(550) was 1.05.

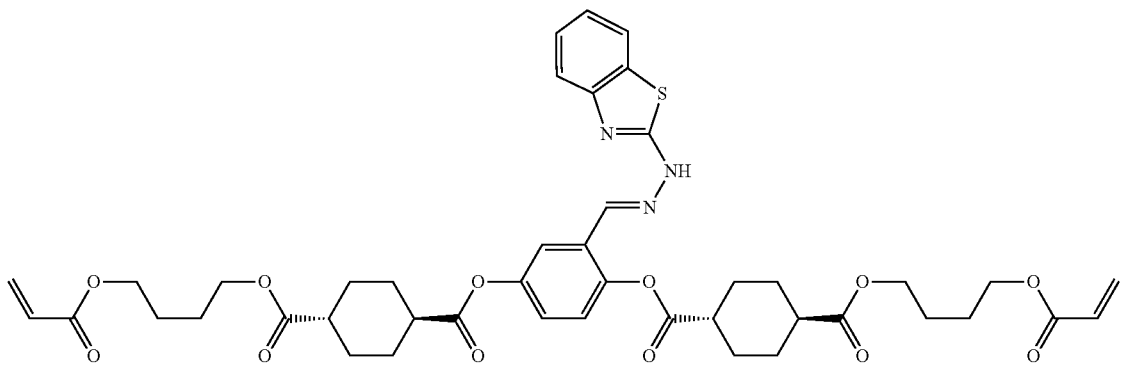

Compound 8-B

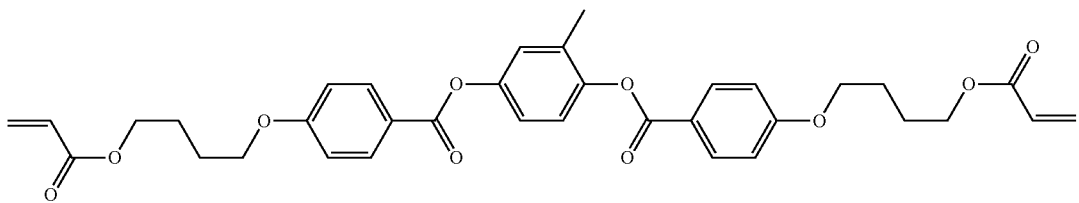

Compound B

Comparative Example 1

Preparation of Optical Film 11

Preparation of Optically Anisotropic Layer 11

By changing the liquid crystal compound 2-B of the coating liquid 1 for an optically anisotropic layer used in Example 1 to the compound A, a coating liquid 11 for an optically anisotropic layer was prepared. In the same manner as in Example 1 except that the coating liquid 1 for an optically anisotropic layer used in Example 1 was changed to the coating liquid 11 for an optically anisotropic layer, an optically anisotropic layer 11 was formed and an optical film 11 was obtained. The optical characteristics of the optical film 11 were confirmed by using an automatic birefringence meter (KOBRA-21ADH, manufactured by Oji Scientific Instruments), and it was found that at a wavelength of 550 nm, the Re was 130 nm, the Rth was 65 nm, the Re(450)/Re(550) was 0.90, and the Re(650)/Re(550) was 1.01.

Comparative Example 2

Preparation of Optical Film 12

Preparation of Optically Anisotropic Layer 12

By changing the liquid crystal compound 2-B of the coating liquid 1 for an optically anisotropic layer used in Example 1 to the compound B used in Example 3, a coating liquid 12 for an optically anisotropic layer was prepared. In the same manner as in Example 1 except that the coating liquid 1 for an optically anisotropic layer used in Example 1 was changed to the coating liquid 12 for an optically anisotropic layer, the coating liquid was coated and aligned in a nematic liquid crystal state, and alignment fixation by irradiation with ultraviolet rays was carried out, thereby forming an optically anisotropic layer 12 and obtaining an optical film 12. The optical characteristics of the optical film 12 were confirmed by using an automatic birefringence meter (KOBRA-21ADH, manufactured by Oji Scientific Instruments), and it was found that at a wavelength of 550 nm, the Re was 135 nm, the Rth was 67 nm, the Re(450)/Re(550) was 1.10, and the Re(650)/Re(550) was 0.95.

Example 4

Preparation of Anti-Reflection Plate for Organic EL (Preparation of Alignment Film 1-1)

Using a commercially available triacetyl cellulose film "Z-TAC" (manufactured by Fujifilm Corporation) as a support, a coating solution for forming an alignment film 1 having the following composition was continuously applied with a #8 wire bar. Then, the coated surface was dried with hot air at 60° C. for 60 seconds and then with hot air at 100° C. for 120 seconds to form an alignment film 1-1.

| Composition of Coating Solution for Forming Alignment Film 1 | |
|---|---|
| Non-modified Polyvinyl Alcohol PVA103 (manufactured by Kuraray Co., Ltd.) | 2.4 parts by mass |

Compound A

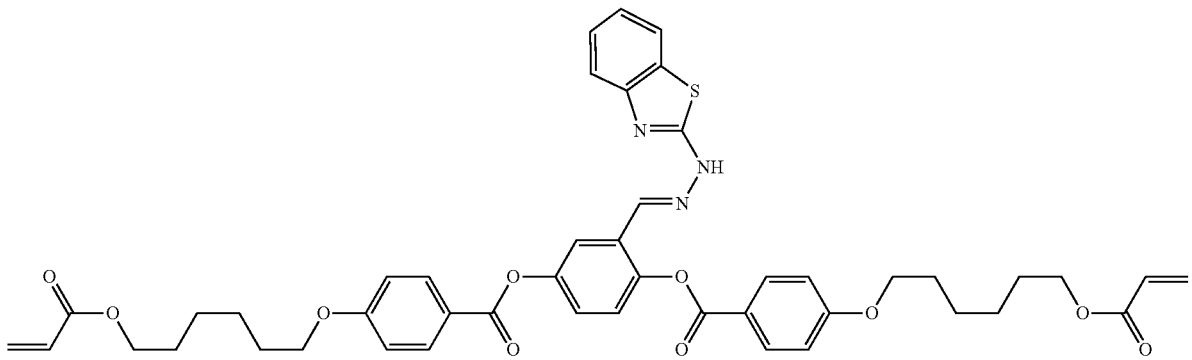

-continued

| Composition of Coating Solution for Forming Alignment Film 1 | |
|---|---|
| Isopropyl alcohol | 1.6 parts by mass |
| Methanol | 36 parts by mass |
| Water | 60 parts by mass |

(Preparation of Positive C-Plate 1-1)

The following coating liquid 1-1 for forming a positive C-plate was applied onto the obtained alignment film 1-1, and heated and aged at a temperature of the film surface of 60° C. for 60 seconds, and then irradiated with ultraviolet rays at 1000 mJ/cm$^2$ using an air-cooled metal halide lamp (manufactured by Eye Graphics Co., Ltd.) at 70 mW/cm$^2$ under an atmospheric air to fix the alignment state. The polymerizable liquid crystal compounds B01 and B02 were vertically aligned to prepare a positive C-plate 1-1. The optical characteristics thereof were confirmed by using an automatic birefringence meter (KOBRA-21ADH, manufactured by Oji Scientific Instruments), and it was found that the polymerizable rod-shaped liquid crystal compound was homeotropically aligned with an Re of 0 nm, an Rth of 110 nm, and a tilt angle of the optical axis of 90° at a wavelength of 550 nm.

| Composition of Coating Liquid 1-1 for Forming Positive C-Plate | |
|---|---|
| Liquid crystal compound B01 | 80 parts by mass |
| Liquid crystal compound B02 | 20 parts by mass |
| Vertical alignment agent (S01) | 1 part by mass |
| Vertical alignment agent (S02) | 0.5 parts by mass |
| Ethylene oxide-modified trimethylol propane triacrylate (V#360, manufactured by Osaka Organic Chemical Industry Ltd.) | 8 parts by mass |
| Irgacure 907 (manufactured by BASF Japan, Ltd.) | 3 parts by mass |
| Kayacure-DETX (manufactured by Nippon Kayaku Co., Ltd.) | 1 part by mass |
| B03 | 0.4 parts by mass |
| Methyl ethyl ketone | 170 parts by mass |
| Cyclohexanone | 30 parts by mass |

B01
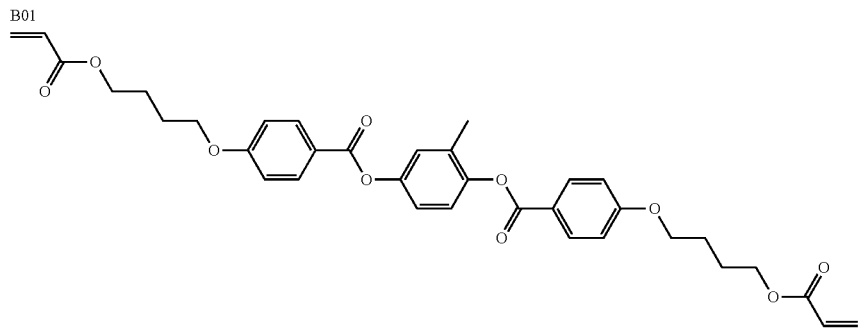

B02
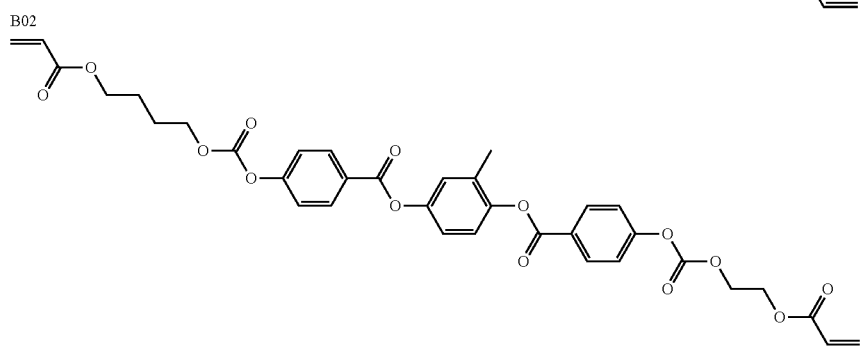

B03
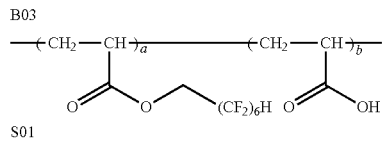

S01
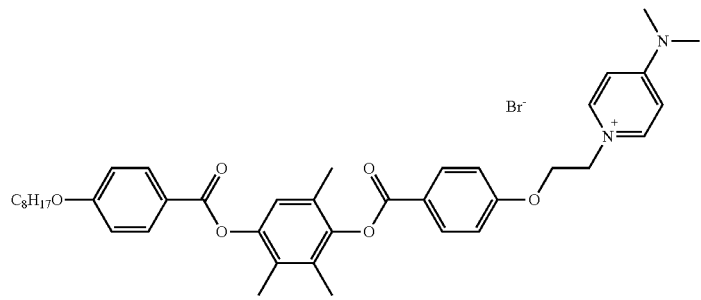

S02
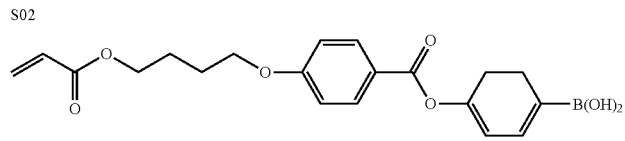

(Preparation of Anti-Reflection Plate)

A laminate having a polarizer (thickness of 20 μm) formed from a stretched polyvinyl alcohol, only one surface of which was protected with triacetyl cellulose (thickness of 40 μm), was used. An optically anisotropic layer, in which the optical film 1 (positive A-plate) and the positive C-plate 1-1 (provided that the thickness of the positive C-plate is controlled so as to have an Rth of −65 nm at 550 nm) were laminated in this order on the surface of the film on the polarizer of the laminate (surface not protected with triacetyl cellulose), was bonded by an optically isotropic adhesive (SK2057, manufactured by Soken Chemical & Engineering Co., Ltd.) to prepare an anti-reflection plate for an organic EL (circularly polarizing plate). Here, the angle between the transmission axis of the polarizer and the slow axis of the optically anisotropic layer of the positive A-plate was set to 45°.

Examples 5 to 6

In the same procedure as in Example 4, except that in the preparation of the anti-reflection plate for an organic EL of Example 4, the optical film 1 was changed to each of optical films 2 and 3, each of anti-reflection plates for an organic EL of Examples 5 and 6 was prepared.

Comparative Examples 3 to 5

In the same procedure as in Example 4, except that in the preparation of the anti-reflection plate for an organic EL of Example 4, the optical film 1 was changed to each of optical films 11 and 12, each of anti-reflection plates for an organic EL of Comparative Examples 3 and 4 was prepared.

Further, in the same procedure as in Example 4, except that in the preparation of the anti-reflection plate for an organic EL of Example 4, the optical film 1 was changed to optical film 11 and bonding of the positive C-plate was not carried out, an anti-reflection plate for an organic EL of Comparative Example 5 was prepared.

<Mounting into Organic EL Element and Evaluation of Display Performance>

(Mounting into Display Apparatus)

GALAXY SII manufactured by SAMSUNG having an organic EL panel mounted therein was decomposed to delaminate a circularly polarizing plate, and the anti-reflection plates of Examples 4 to 6, and Comparative Examples 3 to 5 were bonded thereto to prepare display apparatuses.

(Evaluation of Display Performance)

The visibility under bright light and the display quality of the organic EL display apparatuses prepared were evaluated.

The display apparatuses were allowed to perform white display, black display, and image display, and reflected light was observed when fluorescent light and the like were reflected at a front surface and a polar angle of 60 degrees. The display qualities at the front surface and the polar angle of 60 degrees were evaluated in accordance with the following criteria. The results are shown in Table 1.

4: The color shift is not visually recognized at all (acceptable).

3: The color difference is visually recognized, but is negligible (acceptable).

2: The color difference is visually recognized, but the amount of reflected light is small, which is not a problem for use (acceptable).

1: The color difference is visually recognized and the amount of reflected light is large, which is thus unacceptable.

TABLE 1

| | | Positive A-plate | | | | Positive C | Total | Display performance | |
|---|---|---|---|---|---|---|---|---|---|
| | Compound | Re (nm) | Re (450/550) | Re (650/550) | Rth (nm) | Rth (nm) | Rth (nm) | Front surface | Polar angle of 60° |
| Example 4 | 2-B | 125 | 0.70 | 1.07 | 63 | −63 | 0 | 4 | 4 |
| Example 5 | 5-B | 130 | 0.74 | 1.06 | 65 | −65 | 0 | 4 | 4 |
| Example 6 | 8-B (80% by weight) B (20% by weight) | 130 | 0.78 | 1.05 | 65 | −65 | 1 | 4 | 4 |
| Comparative Example 3 | A | 135 | 0.90 | 1.01 | 67 | −65 | 2 | 2 | 2 |
| Comparative Example 4 | B | 140 | 1.10 | 0.95 | 70 | −65 | 5 | 1 | 1 |
| Comparative Example 5 | A | 135 | 0.90 | 1.01 | 67 | None | 67 | 1 | 1 |

(Preparation of Optical Film 21)

The following coating liquid 21 for an optically anisotropic layer was prepared.

| Composition of coating liquid 21 for optically anisotropic layer | |
|---|---|
| Liquid crystal compound 8-B | 15 parts by mass |
| Photopolymerization initiator (Irgacure 819, manufactured by Ciba Specialty Chemicals Inc.) | 0.45 part by mass |
| Fluorine-containing compound A | 0.12 parts by mass |
| Chloroform | 35 parts by mass |

Compound 8-B

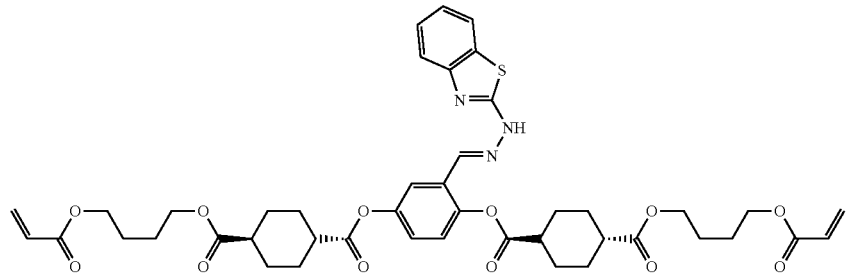

By the same method as in Example 1 except that the coating liquid 1 for an optically anisotropic layer used in Example 1 was changed to a coating liquid 21 for an optically anisotropic layer, the coating liquid was coated, and alignment in a nematic liquid crystal state and alignment fixation by irradiation with ultraviolet rays were carried out, thereby forming an optically anisotropic layer 21 and obtaining an optical film 21. The optical characteristics of the optical film 21 were confirmed by using an automatic birefringence meter (KOBRA-21ADH, manufactured by Oji Scientific Instruments), and it was found that at a wavelength of 550 nm, the Re was 130 nm, the Rth was 65 nm, the Re(450)/Re(550) was 0.10, and the Re(650)/Re(550) was 1.26. The changes in Re($\lambda$)/Re(550) of the optical film 21 due to the wavelength $\lambda$ were shown in FIG. 1, together with the changes in the Re($\lambda$)/Re(550) of the optical films 1, 3, and 12 due to the wavelength $\lambda$.

An A-plate film could be obtained, which had a wavelength $\lambda$1 with a value of Re($\lambda$)/Re(550) showing a change from the decrease to the increase when the Re($\lambda$) in the wavelength $\lambda$ range of 400 nm to 650 nm was measured.

(Preparation 1 of Cellulose Acetate Film)

The respective components in the composition of the following cellulose acetate solution were charged into a mixing tank, and stirred under heating to dissolve the respective components, thereby preparing a cellulose acetate solution.

| (Composition of Cellulose Acetate Solution) | |
|---|---|
| Cellulose acetate with an acetylation degree of 60.9% | 100 parts by mass |
| Triphenyl phosphate (plasticizer) | 7.8 parts by mass |
| Biphenyldiphenyl phosphate (plasticizer) | 3.9 parts by mass |

-continued

| (Composition of Cellulose Acetate Solution) | |
|---|---|
| Methylene chloride (first solvent) | 318 parts by mass |
| Methanol (Second solvent) | 47 parts by mass |

The following exemplary compound (44-A) or the following comparative compound (1), 87 parts by mass of methylene chloride, and 13 parts by mass of methanol were charged into another mixing tank, and stirred under heating, thereby preparing the respective retardation controlling agent solutions. Further, the amounts of the respective compounds to be added are set as described in Table 2.

474 parts by mass of the cellulose acetate solution was mixed with 36 parts by mass of each of the retardation controlling agent solutions prepared above, and the mixture was sufficiently stirred to prepare a dope. The amount of the exemplary compound or the comparative compound was adjusted such that the amount to be added (in parts by mass) with respect to 100 parts by mass of cellulose acetate was as described in Table 2.

The obtained dope was cast using a band casting machine. A film having an amount of the residual solvent of 15% by mass was laterally stretched by free-end uniaxial stretching under a stretch temperature of 150° C. at a stretching ratio of 15% to produce a cellulose acetate film (thickness: 92 μm).

With respect to the cellulose acetate film thus prepared, the Re values at wavelengths of each of 450 nm, 550 nm, and 630 nm were measured by making light at each wavelength incident to the film in the normal direction, using KOBRA 21ADH (manufactured by Oji Scientific Instruments). The results are shown in Table 2. In addition, it should be noted that No. 1 in Table 2 corresponds to a cellulose acetate film produced in the same manner as the others except that no retardation controlling agent solution was added.

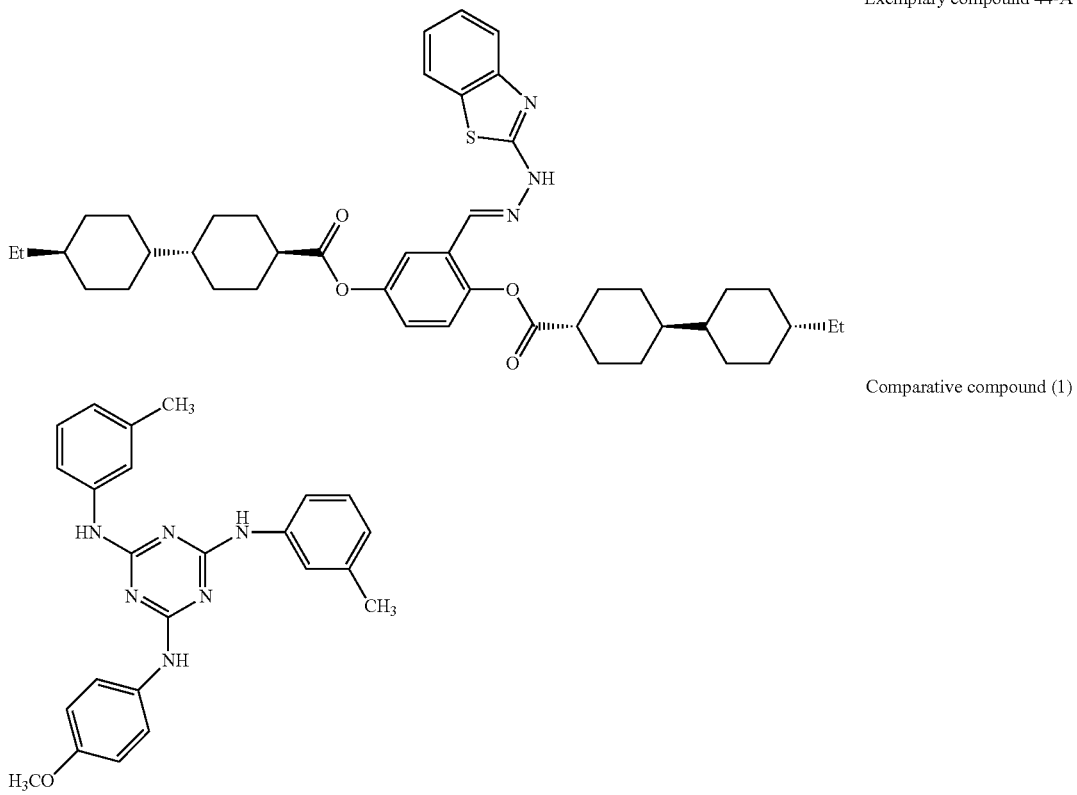

Exemplary compound 44-A

Comparative compound (1)

TABLE 2

| | Compound | Amount to be added (parts by mass) | Δn (450)/ Δn (550) | Δn (630)/ Δn (550) |
|---|---|---|---|---|
| No. 1 | None | 0 | 0.10 | 1.52 |
| No. 2 | Comparative compound (1) | 3.5 | 1.01 | 1.02 |
| No. 3 | Comparative compound (1) | 5.0 | 1.08 | 0.97 |
| No. 4 | 44-A | 3.5 | 0.62 | 1.16 |
| No. 5 | 44-A | 5.0 | 0.65 | 1.14 |

From the results shown in Table 2, it was found that the sample No. 1 in which the retardation controlling agent solution was not used had an extremely small Re value at a wavelength of 450 nm, and thus there was no expression of Re by stretching of the film. It was also found that the sample Nos. 2 and 3 to which the comparative compound (1) was added did not provide reverse wavelength dispersion of birefringence Δn.

To the contrary, it was found that the samples of the present invention (Nos. 4 and 5) provided excellent wavelength dispersion of birefringence Δn.

What is claimed is:

1. An optical film comprising:
an optically anisotropic layer containing a compound represented by the following general formula (1) or an optically anisotropic layer formed by the curing of a polymerizable composition containing a compound represented by the following general formula (1):

General Formula (1)

$$P_1-Sp_1-L_5-(B_1-L_3)_{\overline{a}}A_2-L_1-\overset{\overset{\displaystyle Z}{\|}}{\underset{\displaystyle Y}{A_1}}-L_2-A_3-(L_4-B_2)_{\overline{b}}L_6-Sp_2-P_2$$

wherein:
$L_1$ to $L_6$ each independently represent a single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, —NR$^{25}$—CO—NR$^{26}$—, —R$^1$C=CR$^{11}$—, —R$^2$C=N—, —N=N—, —CO—NR$^3$—, —NR$^4$—CO—, —R$^5$C=N—NR$^6$—, —CO—NR$^7$—NR$^8$—, —R$^9$C=N—S—, —CO—NR$^{10}$—S—, —CO—S—, R$^{11}$C=N—N=, or —R$^{12}$C=C—NR$^{13}$—,
$A_1$ represents an aromatic group which may have a substituent,
$A_2$ and $A_3$ each independently represent a cyclic aliphatic group which may have a substituent,
$B_1$ and $B_2$ each independently represent a cyclic aliphatic group which may have a substituent,
$Sp_1$ and $Sp_2$ each independently represent —(CH$_2$)$_n$—, —(CH$_2$)$_n$—O—, —(CH$_2$—O—)$_n$—, or —(CH$_2$CH$_2$—O—)$_m$,
n represents an integer of 2 to 12,
m represents an integer of 2 to 6,
$P_1$ and $P_2$ each independently represent a polymerizable group, an alkyl group, or a hydrogen atom,
Y represents —R$^1$C=CR$^{11}$—, —R$^2$C=N—, —N=N—, —CO—NR$^3$—, —NR$^4$—CO—, —R$^5$C=N—NR$^6$—, —CO—NR$^7$—NR$^8$—, —R$^9$C=N—S—, —CO—NR$^{10}$—S—, —CO—S—, —R$^{11}$C=N—N=, or —R$^{12}$C=C—NR$^{13}$—, $R^1$ to $R^{10}$, and $R^{12}$ and $R^{13}$ each independently represent a hydrogen atom or an alkyl group having 1 to 6 carbon atoms, $R^{11}$ represents a hydrogen atom, an ester group, an acyl group, or a cyano group, $R^{21}$ to $R^{26}$ each represent a hydrogen atom or an alkyl group having 1 to 6 carbon atoms, Z represents an aromatic group which may have a substituent, and a and b each independently represent any one integer of 0 to 2.

2. The optical film according to claim 1, wherein the aromatic group represented by Z is an aromatic group obtained by removing one or two hydrogen atoms from an aromatic cyclic compound represented by any one of the following Z-1 to Z-7, and Q represents —O—, —S—, or —NR$^{17}$—, and $R^{17}$ represents a hydrogen atom or an alkyl group having 1 to 6 carbon atoms.

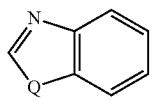
Z-1

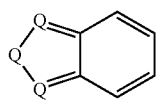
Z-2

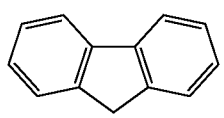
Z-3

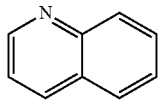
Z-4

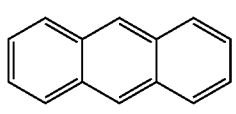
Z-5

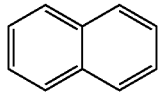
Z-6

Z-7

3. The optical film according to claim 1, wherein the aromatic group represented by A$_1$ is a trivalent aromatic group represented by the following A1-1, A1-2, or A1-3, and *1, *2, and *Y each represent a bonding position with L$_1$, L$_2$, and Y.

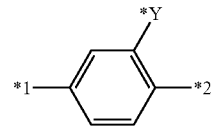
A1-1

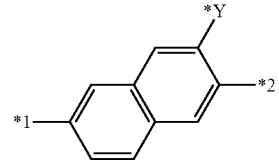
A1-2

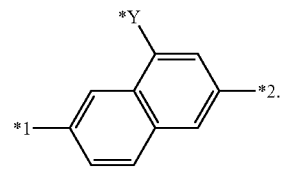
A1-3

4. The optical film according to claim 1, wherein A$_2$, A$_3$, B$_1$, and B$_2$ are each a trans-1,4-cyclohexylene group.

5. The optical film according to claim 1, wherein Sp$_1$ and Sp$_2$ are each independently an alkylene group having 2 to 12 carbon atoms or an alkylene oxide group having 2 to 12 carbon atoms.

6. The optical film according to claim 1, wherein L$_1$ and L$_2$ are each independently a single bond, —CO—, —CO—O—, or —O—CO—.

7. The optical film according to claim 1, wherein L$_3$ and L$_4$ are each independently a single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$—, or —NR$^{25}$—CO—NR$^{26}$—, and $R^{21}$ to $R^{26}$ each represent a hydrogen atom or an alkyl group having 1 to 6 carbon atoms.

8. The optical film according to claim 1, comprising an optically anisotropic layer formed by the curing of a polymerizable composition containing the compound represented by General Formula (1), wherein the polymerizable composition contains at least one or more asymmetric polymerizable compounds.

9. The optical film according to claim 1, comprising an optically anisotropic layer formed by the curing of a polymerizable composition containing the compound represented by General Formula (1), and further comprising:

a photo-alignment film, wherein the optically anisotropic layer is directly in contact with the photo-alignment film.

10. A polarizing plate comprising the optical film according to claim 1.

11. A circularly polarizing plate comprising the optical film according to claim 1.

12. A display apparatus comprising the optical film according to claim 1.

13. The optical film according to claim 1, wherein the Y—Z site has a hydrogen bonding substituent.

14. The optical film according to claim 13, wherein the hydrogen bonding substituent is formed of a hydrogen bond donating group and a hydrogen bond accepting group, the hydrogen bond donating group represents a group selected from the group consisting of an amino group, an acylamino group, an alkoxycarbonylamino group, an aryloxycarbonylamino group, a sulfonylamino group, a hydroxy group, a mercapto group, a carboxyl group, a methylene group substituted with an electron withdrawing group, and a methine group substituted with an electron withdrawing group, and the hydrogen bond accepting group represents a group selected from the group consisting of a hetero atom having unshared electron pairs on a hetero ring contained inside, a hydroxy group, an aldehyde, a ketone, a carboxylic ester, a carboxylic amide, a lactone, a lactam, a sulfonic amide, a phosphoric amide, a urethane, a urea, an ether structure, an aliphatic amine, an aromatic amine, and a carboxylic amide.

\* \* \* \* \*